United States Patent
Cerundolo et al.

(10) Patent No.: US 10,314,796 B2
(45) Date of Patent: *Jun. 11, 2019

(54) INKT CELL MODULATORS AND METHODS OF USING THE SAME

(71) Applicant: LUDWIG INSTITUTE FOR CANCER RESEARCH, Zurich (CH)

(72) Inventors: Vincenzo Cerundolo, Oxford (GB); Gurdyal S. Besra, Birmingham (GB); Liam R. Cox, Birmingham (GB)

(73) Assignee: LUDWIG INSTITUTE FOR CANCER RESEARCH, Zurich (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/616,672

(22) Filed: Jun. 7, 2017

(65) Prior Publication Data

US 2017/0368002 A1 Dec. 28, 2017

Related U.S. Application Data

(63) Continuation of application No. 15/153,425, filed on May 12, 2016, now Pat. No. 9,700,532, which is a continuation of application No. 14/361,434, filed as application No. PCT/EP2012/074140 on Nov. 30, 2012, now Pat. No. 9,365,496.

(60) Provisional application No. 61/565,287, filed on Nov. 30, 2011.

(51) Int. Cl.

| | |
|---|---|
| *A61J 1/14* | (2006.01) |
| *A61K 31/16* | (2006.01) |
| *A61K 39/00* | (2006.01) |
| *A61K 45/06* | (2006.01) |
| *C07K 16/28* | (2006.01) |
| *C07K 16/30* | (2006.01) |
| *A61K 31/165* | (2006.01) |
| *C07C 233/18* | (2006.01) |

(52) U.S. Cl.
CPC ............... *A61K 31/16* (2013.01); *A61J 1/14* (2013.01); *A61K 31/165* (2013.01); *A61K 39/0011* (2013.01); *A61K 45/06* (2013.01); *C07C 233/18* (2013.01); *C07K 16/2818* (2013.01); *C07K 16/30* (2013.01); *C07C 2601/14* (2017.05); *C07C 2601/18* (2017.05); *C07K 2317/21* (2013.01); *C07K 2317/24* (2013.01)

(58) Field of Classification Search
CPC ......... A61J 1/14; A61K 31/16; A61K 31/165; A61K 39/0011; A61K 45/06; C07C 233/18; C07C 2601/14; C07C 2601/18; C07K 16/2818; C07K 16/30; C07K 2317/21; C07K 2317/24
See application file for complete search history.

(56) References Cited

U.S. PATENT DOCUMENTS

| | | |
|---|---|---|
| 5,139,941 A | 8/1992 | Muzyczka et al. |
| 5,252,479 A | 10/1993 | Srivastava |
| 5,328,688 A | 7/1994 | Roizman |
| 5,474,935 A | 12/1995 | Chatterjee et al. |
| 5,585,362 A | 12/1996 | Wilson et al. |
| 5,622,856 A | 4/1997 | Natsoulis |
| 5,631,237 A | 5/1997 | Dzau et al. |
| 5,658,776 A | 8/1997 | Flotte et al. |
| 5,661,033 A | 8/1997 | Ho et al. |
| 5,670,488 A | 9/1997 | Gregory et al. |
| 5,693,509 A | 12/1997 | Cotten et al. |
| 5,707,618 A | 1/1998 | Armentano et al. |
| 5,773,289 A | 6/1998 | Samulski et al. |
| 5,789,390 A | 8/1998 | Descamps et al. |
| 5,792,453 A | 8/1998 | Hammond et al. |
| 5,824,544 A | 10/1998 | Armentano et al. |
| 5,830,727 A | 11/1998 | Wang et al. |
| 5,834,441 A | 11/1998 | Philip et al. |
| 5,849,571 A | 12/1998 | Glorioso et al. |
| 5,851,521 A | 12/1998 | Branellec et al. |
| 5,856,152 A | 1/1999 | Wilson et al. |
| 5,863,541 A | 1/1999 | Samulski et al. |
| 5,879,934 A | 3/1999 | DeLuca |
| 8,299,223 B2 | 10/2012 | Tashiro et al. |
| 8,835,613 B2 | 9/2014 | Berzofsky et al. |
| 9,365,496 B2* | 6/2016 | Cerundolo ............ C07C 233/18 |
| 9,700,532 B2* | 7/2017 | Cerundolo ............ C07C 233/18 |
| 2010/0284965 A1 | 11/2010 | Fahmy et al. |
| 2011/0293658 A1 | 12/2011 | Cerundolo et al. |

(Continued)

FOREIGN PATENT DOCUMENTS

| | | |
|---|---|---|
| WO | WO-9633739 A1 | 10/1996 |
| WO | WO-00/20581 A1 | 4/2000 |

(Continued)

OTHER PUBLICATIONS

Gjerstorff et al., "An overview of the GAGE caner/testis antigen family with the inclusion of newly identified members," Tissue Antigens, 71, 187-192, 2008.*
Alessandri et al., "ETV6 (TEL)-AML1 pre-B acute lymphoblastic leukaemia cells are associated with a distinct antigen-presenting phenotype," British Journal of Haematology, 2002, 116, 266-727.*
McEwen-Smith et al., "The regulatory role of invariant NKT cells in tumor immunity," Cancer Immunol Res. May 2015; 3(5); 425-435 (Year: 2015).*
Rossignol et al., "Evidence for BCR-ABL-dependent dysfunctions of iNKT celss from chronic myeloid leukemia patients," Eur. J. Immunol. 2012. 42: 1870-1875. (Year: 2012).*

(Continued)

*Primary Examiner* — Pancham Bakshi
*Assistant Examiner* — Mark R Luderer
(74) *Attorney, Agent, or Firm* — Marshall, Gerstein & Borun LLP

(57) ABSTRACT

Disclosed herein are α-galactosylceramide (α-GalCer) analogs and compositions thereof, methods of activating invariant Natural Killer T (iNKT) cells using said analogs, methods of treating diseases by activating iNKT cells using said analogs, and combination therapy of said analogs.

26 Claims, 18 Drawing Sheets

(56) References Cited

U.S. PATENT DOCUMENTS

| | | |
|---|---|---|
| 2012/0093875 A1 | 4/2012 | Llebaria Soldevilla et al. |
| 2014/0050780 A1 | 2/2014 | Cerundolo et al. |

FOREIGN PATENT DOCUMENTS

| | | |
|---|---|---|
| WO | WO-2007/050668 A1 | 5/2007 |
| WO | WO-2010/055340 A1 | 5/2010 |
| WO | WO-2010/106215 A1 | 9/2010 |
| WO | WO-2012/088414 A1 | 6/2012 |

OTHER PUBLICATIONS

Crough et al., "Modulation of human Va24+VBII+NKT cells by age, malignancy and conventional anticancer therapies," British Journal of Cancer, 2004, 91, 1880-1886 (Year: 2004).*

Yoshioka et al., "Role of Natural Killer T Cells in the Mouse Colitis-Associated Colon Cancer Model," Scandinavian Journal of Immunology, 2011, 75, 16-26. (Year: 2011).*

Andrade et al., Prognostic impact of cancer/testis antigen expression in advanced stage multiple myeloma patients, Cancer Immun., 8:2 (2008).

Atanackovic et al., Booster vaccination of cancer patients with MAGE-A3 protein reveals long-term immunological memory or tolerance depending on priming, Proc. Natl. Acad. Sci. USA, 105(5):1650-5 (2008).

Bender et al., LUD 00-009: Phase I study of intensive course immunization with NY-ESO-1 peptides in HLA-A2 positive patients with NY-ESO-1-expressing cancer, Cancer Immunol., 7:16 (2007).

Borg et al., CD1d-lipid-antigen recognition by the semi-invariant NKT T-cell receptor, Nature, 448:44-9 (2007).

Carrasco et al., Vaccination of a melanoma patient with mature dendritic cells pulsed with MAGE-3 peptides triggers the activity of nonvaccine anti-tumor cells, J. Immunol., 180(5):3585-93 (2008).

Chen et al., Immunodominant CD4+ responses identified in a patient vaccinated with full-length NY-ESO-1 formulated with ISCOMATRIX adjuvant, Proc. Natl. Acad. Sci. USA, 101(25):9363-8 (2004).

Davis et al., Recombinant NY-ESO-1 protein with ISCOMATRIX adjuvant induces broad integrated antibody and CD4(+) and CD8(+) T cell responses in humans, Proc. Natl. Acad. Sci. USA, 101(29):10697-702 (2004).

Declaration under 37 CFR 1.132 of Dr. Robert A. Volkmann (with biographical sketch), U.S. Appl. No. 14/361,434, dated Dec. 9, 2015.

Diefenbach et al., Safety and immunogenicity study of NY-ESO-1b peptide and montanide ISA-51 vaccination of patients with epithelial ovarian cancer in high-risk first remission, Clin. Cancer Res., 14(9):2740-8 (2008).

Gnjatic et al., NY-ESO-1 DNA vaccine induces T-cell responses that are suppressed by regulatory T cells, Clin. Cancer Res., 15(6):2130-9 (2009).

Gunzer et al., Systemic administration of a TLR7 ligand leads to transient immune incompetence due to peripheral-blood leukocyte depletion, Blood, 106(7):2424-32 (2005).

Gure et al., Cancer-testis genes are coordinately expressed and are markers of poor outcome in non-small cell lung cancer, Clin. Cancer Res., 11(22):8055-62 (2005).

Harrak et al., Aminocyclitol-substituted phytoceramides and their effects on iNKT cell stimulation, ChemMedChem., 4:1608-13 (2009).

International Preliminary Report on Patentability, corresponding International Application No. PCT/EP2012/074140, dated Jun. 3, 2014.

International Search Report and Written Opinion, corresponding International Application No. PCT/EP2012/074140, dated Feb. 21, 2013.

Jager et al., Induction of primary NY-ESO-1 immunity: CD8+ T lymphocyte and antibody responses in peptide-vaccinated patients with NY-ESO-1+ cancers, Proc. Natl. Acad. Sci. USA, 97(22):12198-203 (2000).

Jager et al., Recombinant vaccinia/fowlpox NY-ESO-1 vaccines induce both humoral and cellular NY-ESO-1-specific immune responses in cancer patients, Proc. Natl. Acad. Sci. USA, 103(39):14453-8 (2006).

Jukes et al., Non-glycosidic compounds can stimulate both human and mouse iNKT cells, Eur. J. Immunol., pp. 1-11 (2016).

Kakimi et al., A phase I study of vaccination with NY-ESO-1f peptide mixed with Picibanil OK-432 and Montanide ISA-51 in patients with cancers expressing the NY-ESO-1 antigen, Int. J. Cancer, 129(12):2836-46 (2011).

Kawabata et al., Antibody response against NY-ESO-1 in CHP-NY-ESO-1 vaccinated patients, Int. J. Cancer, 120(10:2178-84 (2007).

Kawada et al., Heteroclitic serological response in esophageal and prostate cancer patients after NY-ESO-1 protein vaccination, Int. J. Cancer, 130(3):584-92 (2012).

Kim et al., Minimal requirement for a lentivirus vector based on human immunodeficiency virus type 1, J. Virol., 72(1):811-6 (1998).

Krieg et al., CpG motifs in bacterial DNA trigger direct B-cell activation, Nature, 374(6522):546-9 (1995).

Kruit et al., Phase 1/2 study of subcutaneous and intradermal immunization with a recombinant MAGE-3 protein in patients with detectable metastatic melanoma, Int. J. Cancer, 117(4):596-604 (2005).

Lipinski et al., Experimental and computational approaches to estimate solubility and permeability in drug discovery and development settings, Adv. Drug Deliv. Rev., 46:3-26 (2001).

Maraskovsky et al., NY-ESO-1 protein formulated in ISCOMATRIX adjuvant is a potent anticancer vaccine inducing both humoral and CD8+ t-cell-mediated immunity and protection against NY-ESO-1+ tumors, Clin. Cancer Res., 10(8):2879-90 (2004).

Marchand et al., Immunisation of metastatic cancer patients with MAGE-3 protein combined with adjuvant SBAS-2: a clinical report, Eur. J. Cancer, 39(1):70-7 (2003).

Marchand et al., Tumor regressions observed in patients with metastatic melanoma treated with an antigenic peptide encoded by gene MAGE-3 and presented by HLA-A1, Int. J. Cancer, 80(2):219-30 (1999).

Napoletano et al., MAGE-A and NY-ESO-1 expression in cervical cancer: prognostic factors and effects of chemotherapy, Am. J. Obstet. Gynecol., 198(1):99.e1-7 (2008).

Odunsi et al., Vaccination with an NY-ESO-1 peptide of HLA class I/II specificities induces integrated humoral and T cell responses in ovarian cancer, Proc. Natl. Acad. Sci. USA, 104(31):12837-42 (2007).

Quantin et al., Adenovirus as an expression vector in muscle cells in vivo, Proc. Natl. Acad. Sci. USA, 89(7):2581-4 (1992).

Rosenfeld et al., In vivo transfer of the human cystic fibrosis transmembrane conductance regulator gene to the airway epithelium, Cell, 68(1):143-55 (1992).

Scanlan et al., Cancer/testis antigens: an expanding family of targets for cancer immunotherapy, Immunol. Rev., 188:22-32 (2002).

Sharma et al., Immune responses detected in urothelial carcinoma patients after vaccination with NY-ESO-1 protein plus BCG and GM-CSF, J. Immunother., 31(9):849-57 (2008).

Simpson et al., Cancer/testis antigens, gametogenesis and cancer, Nat. Rev. Cancer, 5(8):615-25 (2005).

So et al., Effect of a novel saponin adjuvant derived from Quillaja saponaria on the immune response to recombinant hepatitis B surface antigen, Mol. Cells, 7(2):178-86 (1997).

Stratford-Perricaudet et al., Widespread long-term gene transfer to mouse skeletal muscles and heart, J. Clin. Invest., 90(2):626-30 (1992).

Tashiro et al., RCAI-37, 56, 59, 60, 92, 101, and 102, cyclitol and carbasugar analogs of KRN7000: their synthesis and bioactivity for mouse lymphocytes to produce Th1-biased cytokines, Bioorg. Med. Chem., 17)17):6360-73 (2009).

Tashiro et al., RCAI-56, a carbocyclic analogue of KRN7000:its synthesis and potent activity for natural killer (NK) T cells to preferentially produce interferon-gamma, Tetrahedron Lett., 48:3343-7 (2007).

Tinguely et al., MAGE-C1/CT-7 expression in plasma cell myeloma: sub-cellular localization impacts on clinical outcome, Cancer Sci., 99(4):720-5 (2008).

(56) References Cited

OTHER PUBLICATIONS

Trappeniers et al., 6'-derivatised alpha-GalCer analogues capable of inducing strong CD1d-mediated Th1-biased NKT cell responses in mice, J. Am. Chem. Soc., 130(49):16468-9 (2008).

Uenaka et al., T cell immunomonitoring and tumor responses in patients immunized with a complex of cholesterol-bearing hydrophobized pullulan (CHP) and NY-ESO-1 protein, Cancer Immun., 7:9 (2007).

Vabulas et al., CpG-DNA activates in vivo T cell epitope presenting dendritic cells to trigger protective antiviral cytotoxic T cell responses, J. Immunol., 164(5):2372-8 (2000).

Valmori et al., Vaccination with NY-ESO-1 protein and CpG in Montanide induces integrated antibody/Th1 responses and CD8 T cells through cross-priming, Proc. Natl. Acad. Sci. USA, 104(21):8947-52 (2007).

Van Baren et al., Tumoral and immunologic response after vaccination of melanoma patients with an ALVAC virus encoding MAGE antigens recognized by T cells, J. Clin. Oncol., 23(35):9008-21 (2005).

Velazquez et al., Expression of the cancer/testis antigen NY-ESO-1 in primary and metastatic malignant melanoma (MM)—correlation with prognostic factors, Cancer Immun., 7:11 (2007).

Wada et al., Analysis of peripheral and local anti-tumor immune response in esophageal cancer patients after NY-ESO-1 protein vaccination, Int. J. Cancer, 123(10):2362-9 (2008).

Weiner et al., Immunostimulatory oligodeoxynucleotides containing the CpG motif are effective as immune adjuvants in tumor antigen immunization, Proc. Natl. Acad. Sci. USA, 94(20):10833-7 (1997).

West, "Solid State Chemistry and its Applications", pp. 358 and 365, New York: Wiley (1988).

Yuan et al., CTLA-4 blockade enhances polyfunctional NY-ESO-1 specific T cell responses in metastatic melanoma patients with clinical benefit, Proc. Natl. Acad. Sci. USA, 105(51):20410-5 (2008).

\* cited by examiner

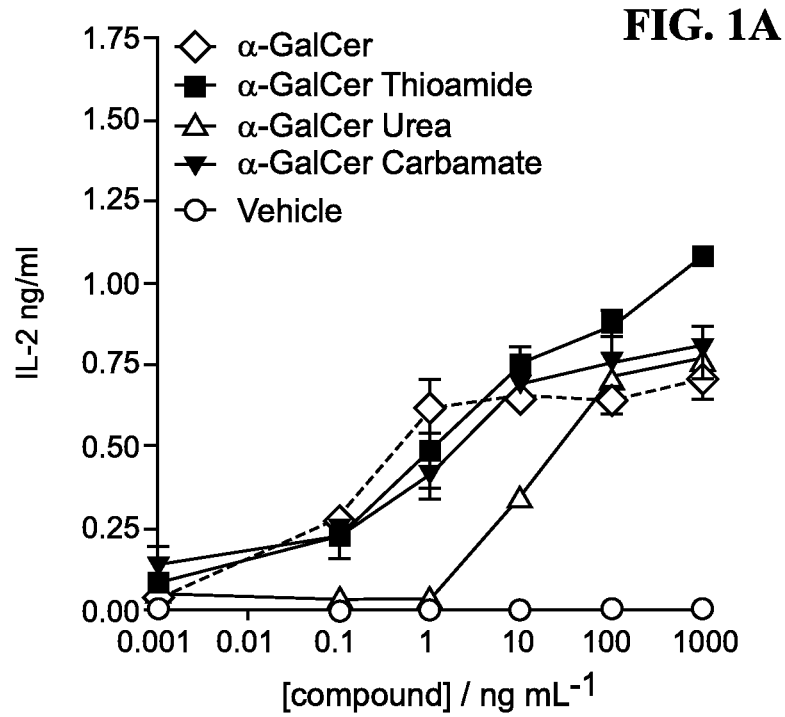
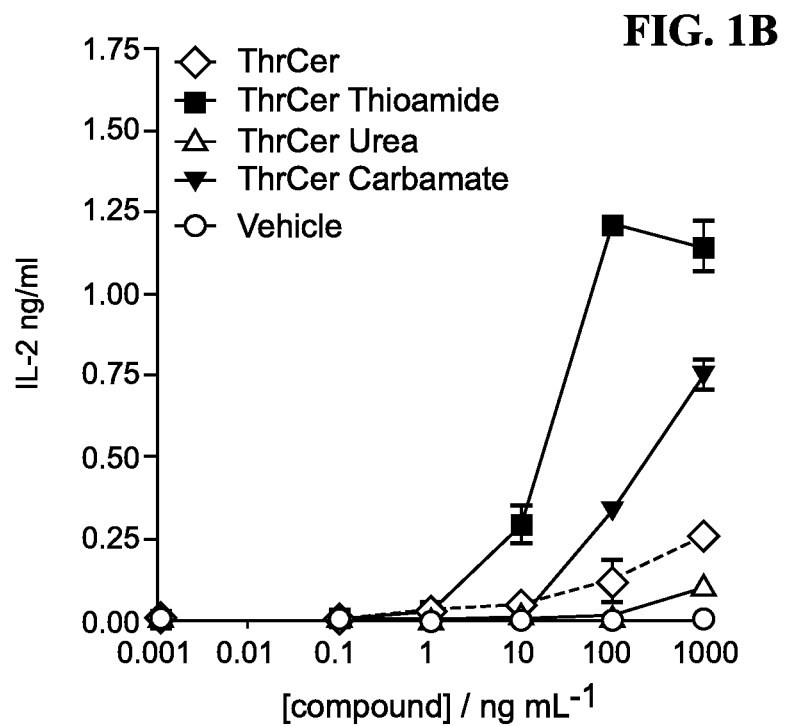

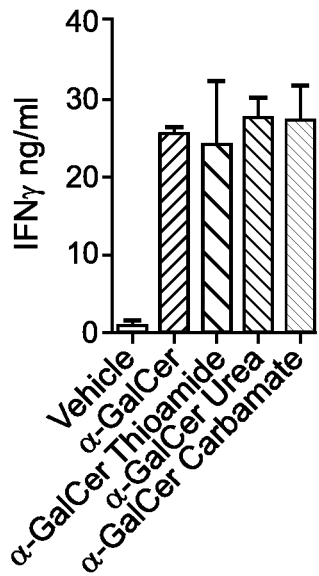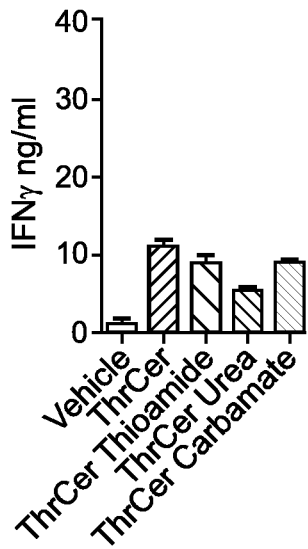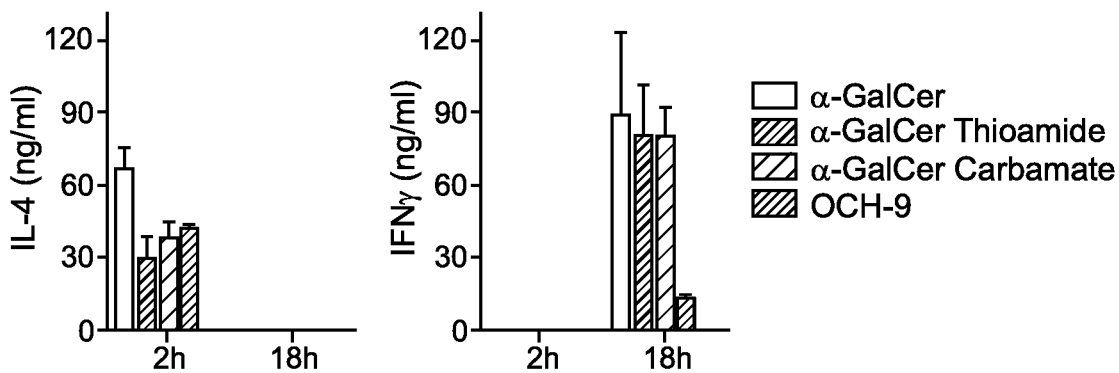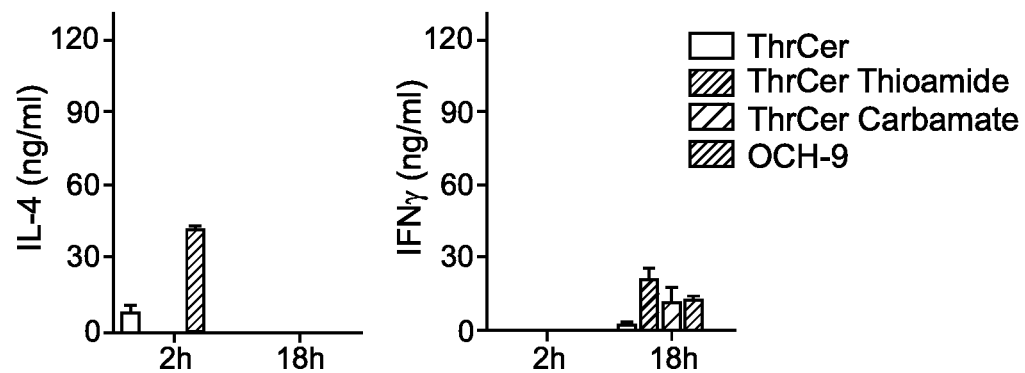

INKT CELL MODULATORS AND METHODS OF USING THE SAME

CROSS-REFERENCE TO RELATED APPLICATIONS

This Application is a continuation of U.S. patent application Ser. No. 15/153,425, filed on May 12, 2016, which is a continuation of U.S. patent application Ser. No. 14/361,434, filed on May 29, 2014 (§ 371(c) date), which is the US national phase of International Application No. PCT/EP2012/074140, filed Nov. 30, 2012, which claims priority benefit of U.S. Provisional Application 61/565,287, filed on Nov. 30, 2011. The entire contents of these applications are incorporated herein by reference in their entirety.

BACKGROUND

Natural killer T (NKT) cells have been implicated in a range of important immune surveillance mechanisms, such as host defense against external pathogens, immune tolerance and malignancy. NKT cells can be further divided into two subsets, so-named Type I and Type II. Type I NKT cells have received the most attention. These cells are also known as invariant NKT (iNKT) cells owing to their expression of an invariant α chain T cell receptor (TCR; Vα14-Jα18 chain in mice and Vα24-Jα18 chain in humans), which is paired with a more variable β chain. In contrast, Type II NKT cells have a diverse TCR repertoire and are less well defined, although a subset has been shown to be reactive to sulfatide. The iNKT cell TCR recognizes lipid antigens presented in the context of the non-polymorphic MHC class I-like protein, CD1d. The CD1d molecule has been shown to bind a range of dialkyl lipids and glycolipids and the ensuing iNKT cell TCR recognition of the CD1d-lipid complex leads to the rapid proliferation and release of a plethora of cytokines (both pro-inflammatory and regulatory). The activation of iNKT cells is an important step in 'boosting' adaptive immune responses through the activation and maturation of dendritic cells (DC) and B cells through CD40-CD40L interactions, and the activation of natural killer (NK) cells following interferon gamma (IFNγ) release. Since the structure of CD1d ligands has been shown to govern the released cytokine profile, the development of lipid molecules that promote the specific activation of iNKT cells, could find very useful application in the treatment of a wide range of disorders.

Of the range of lipids that bind to CD1d, the glycolipid α-galactosylceramide (α-GalCer) is one of the most potent. α-GalCer is a derivative of the agelasphins, which are naturally occurring glycolipids that were isolated from the marine sponge *Agelas mauritianus*. Recognition of the α-GalCer-CD1d complex by the iNKT cell TCR results in the secretion of a range of cytokines, and the initiation of a powerful immune response.

While α-GalCer remains one of the most potent iNKT cell agonists and has shown potential in the treatment of various conditions, it may prove difficult to use this molecule widely as a useful therapeutic agent, at least as a direct activator of iNKT cells: not only does α-GalCer-mediated iNKT cell activation lead to the secretion of both T helper Type 1 (Th1) (e.g. IFN-γ) and T helper Type 2 (Th2) (e.g. interleukin-4 (IL-4)) cytokines, and therefore a mixed immune response, but more importantly over-stimulation of iNKT cells, which can result in their entering a long-term anergic state, i.e. unresponsiveness to subsequent α-GalCer stimulation and preferential IL-4 production, which would be deleterious for long-term therapy. Loss of circulating levels of iNKT cells could represent a therapeutically significant limitation with iNKT-cell-based therapies if multi-dosing regimens are required. Thus, a need exists for other iNKT cell activators.

SUMMARY

This invention provides compounds, compositions of matter, and methods of making and using the compounds and compositions that are useful in relation to iNKT activation and all of the applications (including therapeutic or prophylactic medical applications) relating to iNKT activation.

By way of example, compounds are disclosed having a structure of formula (I):

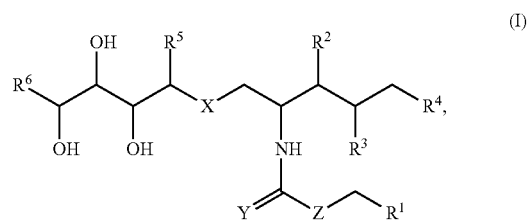

wherein $R^1$ is $C_5$-$C_{25}$ alkyl, $C_5$-$C_{25}$ alkenyl, $C_5$-$C_{25}$ alkynyl, $C_5$-$C_{25}$ heteroalkyl, $C_5$-$C_{25}$ heteroalkenyl, or $C_5$-$C_{25}$ heteroalkynyl; $R^2$ and $R^3$ are each independently selected from H, OH, SH, amino or substituted amino; $R^4$ is $C_5$-$C_{20}$ alkyl, $C_5$-$C_{20}$ alkenyl, $C_5$-$C_{20}$ alkynyl, $C_5$-$C_{20}$ heteroalkyl, $C_5$-$C_{20}$ heteroalkenyl, or $C_5$-$C_{20}$ heteroalkynyl; $R^6$ and $R^5$ are each independently selected from H, alkyl, and alkenyl, or $R^6$ and $R^5$ together form a 6-, 7-, or 8-membered cycloalkyl or cycloalkenyl ring; X is O, S, $SO_2$, SO(NH), SO(N(alkyl)), NH, N(alkyl), or $CH_2$; Y is O, NH, N(alkyl), or S; Z is O, S, NH, N(alkyl), or $CH_2$; with the proviso that with the proviso that (a) when Y and X are each O and $R^5$ and $R^6$ are each H, Z is not $CH_2$; and (b) when Y is O, $R^6$ and $R^5$ together form a 6-membered cycloalkyl ring, and Z is $CH_2$, the cycloalkyl ring is not substituted with —$CH_2OH$, —OH, —$CH_3$, or —$CH_2OCH_3$, or a salt, ester, solvate, or hydrate thereof. In some embodiments, the compounds disclosed herein having a structure (IA), (IB), (IC), or (ID):

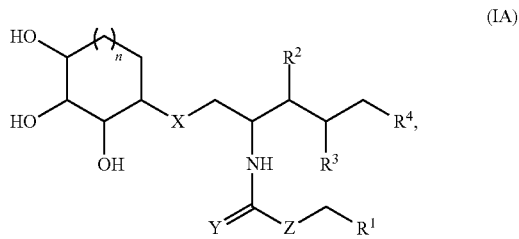

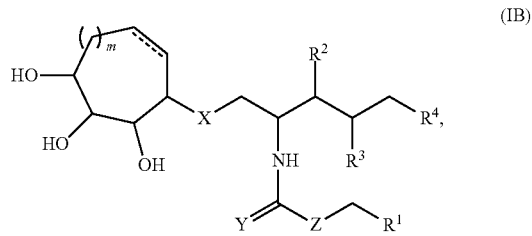

-continued

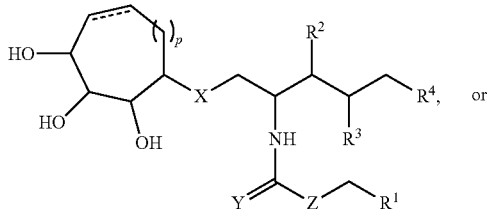
(IC)

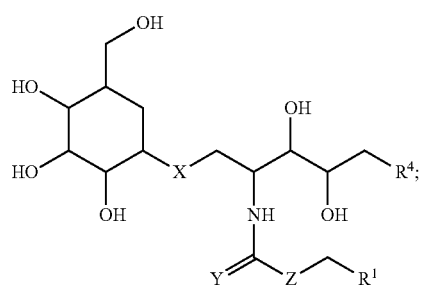
(ID)

wherein n is 1, 2, or 3; m is 0, 1, or 2; p is 1 or 2; and the dashed line is an optional double bond. In some specific sets of embodiments, the dashed line is a double bond, while in other sets of embodiments, the dashed line is a single bond.

In various cases, the compounds disclosed herein have stereochemistry as noted in the structure (IE):

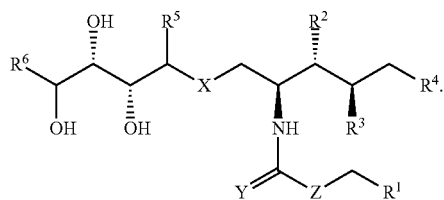
(IE)

In various cases, the compound has a structure of:

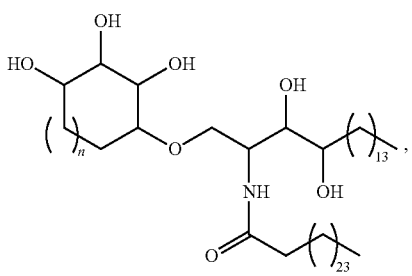

wherein n is 1, 2, or 3, or a salt, ester, solvate, or hydrate thereof, or more specically a structure of:

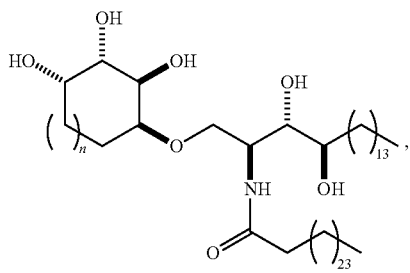

wherein n is 1 (IMM60), 2 (IMM70), or 3 (IMM80), or a salt, ester, solvate, or hydrate thereof.

In some variations, the compound is purified and/or isolated.

Further disclosed herein are compositions that comprise a compound as disclosed herein and one or more pharmaceutically acceptable diluents, excipients, or carriers (pharmaceutical compositions). In some variations, the composition is formulated and/or packaged as a unit dose for administration to a subject. In some variations, a syringe or other administration device is provided that contains the compound or composition.

Also disclosed herein are methods of activating an NKT cell by contacting the cell with a compound or composition as disclosed herein. The activating of the NKT cell can comprise one or more of inducing secretion of a cytokine from the NKT cell, stimulating proliferation of the NKT cell, and upregulating expression of a cell surface marker on the NKT cell. The cytokine can be one or more of IL-1, IL-2, IL-4, IL-5, IL-6, IL-10, IL-13, IL-15, TNF-α, TNF-β, and IFN-γ. The activating can comprise upregulating at least one cell surface marker selected from CD69, CD25, an IL-12 receptor and CD40L.

In some variations, the activating is performed ex vivo, e.g., using a biological sample that contains an NKT cell that has been removed from an organism. In other variations, the activating is performed in vivo, e.g., by administering the compound or composition to the organism by a route through which the compound or composition or metabolite thereof contacts the NKT cell.

The methods disclosed herein can comprise administering a compound or composition as disclosed herein to a subject in need of NKT cell activation. Exemplary subjects are mammalian subjects, which includes human subjects. In some cases, the subject suffers from cancer.

The methods disclosed herein can comprise administering a compound or composition as disclosed herein to a subject suffering from a cancer selected from basal cell carcinoma, breast cancer, leukemia, Burkitt's Lymphoma, colon cancer, esophageal cancer, bladder cancer, gastric cancer, head and neck cancer, hepatocellular cancer, Hodgkin's Lymphoma, hairy cell leukemia, Wilms' Tumor, thyroid cancer, thymoma, thymic carcinoma, testicular cancer, T-cell lymphoma, prostate cancer, non-small cell lung cancer, liver cancer, renal cell cancer, and melanoma.

The methods disclosed herein can further comprise administering a second therapeutic agent to the subject. For example, the methods can comprise administering a chemotherapeutic or an immunotherapeutic agent, a cancer vaccine, a tumor antigen, or a polynucleotide encoding a tumor antigen. The second therapeutic can be administered simultaneously with the compound or composition as disclosed herein, and in some specific cases, the two are co-formulated. The second therapeutic can be administered sequentially with the compound or composition as disclosed herein, e.g., before or after the compound or composition. Repeated administration of one or both of the agents is contemplated.

Methods disclosed herein also can be characterized as methods of treatment or prophylaxis. For example, disclosed herein are methods of treatment or prophylaxis of a subject suffering from any of the conditions described herein, such method comprising administering to the subject a compound or composition described herein. In some variations, the compound or composition is administered in an amount effective to stimulate NKT activation. In some variations, other therapeutic benchmarks are utilized. For example, the compound or composition is administered in an amount effective to slow the growth, or reduce the size, or eliminate a tumor or other cancer. In some variations, the administering is repeated multiple times.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations specifically mentioned above. With respect to aspects of the invention described or claimed with "a" or "an," it should be understood that these terms mean "one or more" unless context unambiguously requires a more restricted meaning. With respect to elements described as one or more within a set, it should be understood that all combinations within the set are contemplated. If aspects of the invention are described as "comprising" a feature, embodiments also are contemplated "consisting of" or "consisting essentially of" the feature.

Aspects of the invention described as methods of treatment should also be understood to include first or subsequent "medical use" aspects of the invention or "Swiss use" of compositions for the manufacture of a medicament for treatment of the same disease or condition.

Multiple embodiments are contemplated for combination inventions described herein. For example, some aspects of the invention that are described as a method of treatment (or medical use) combining two or more compounds or agents, whether administered separately (sequentially or simultaneously) or in combination (co-formulated or mixed). For each aspect described in this manner, the invention further includes a composition comprising the two or more compounds or agents co-formulated or in admixture with each other; and the invention further includes a kit or unit dose containing the two or more compounds/agents packaged together, but not in admixture. Optionally, such compositions, kits or doses further include one or more carriers in admixture with one or both agents or co-packaged for formulation prior to administration to a subject. The reverse also is true: some aspects of the invention are described herein as compositions useful for therapy and containing two or more therapeutic agents. Equivalent methods and uses are specifically contemplated.

Although the applicant(s) invented the full scope of the claims appended hereto, the claims appended hereto are not intended to encompass within their scope the prior art work of others. Therefore, in the event that statutory or judicially-recognized prior art within the scope of a claim is brought to the attention of the applicants by a Patent Office or other entity or individual, the applicant(s) reserve the right to exercise amendment rights under applicable patent laws to redefine the subject matter of such a claim to specifically exclude such prior art or obvious variations of statutory prior art from the scope of such a claim. Variations of the invention defined by such amended claims also are intended as aspects of the invention. Additional features and variations of the invention will be apparent to those skilled in the art from the entirety of this application, and all such features are intended as aspects of the invention.

BRIEF DESCRIPTION OF THE DRAWINGS

FIG. 1 shows the biological activity of six compounds as disclosed herein, α-GalCer, and ThrCer as determined by their ability to stimulate iNKT cell hybridoma DN32, following pulsing of C1R-mCD1d cells with each compound, as measured by the resulting IL-2 released in the supernatant.

FIG. 2 shows the biological activity of the same compounds as FIG. 1, but this time in a human cell model, with human iNKT cells co-cultured with C1R-hCD1d cells and pulsed with 100 ng/mL compound or vehicle, and the resulting IL-2 released in the supernatant measured.

FIG. 3 shows results of an experiment of 1 µg lipid injected into wildtype C57 BL/6 or C57 BL/6 CD1d−/− (NKT cell-deficient) mice, and IL-4 and IFNγ levels measured.

DETAILED DESCRIPTION

Figure 4A:
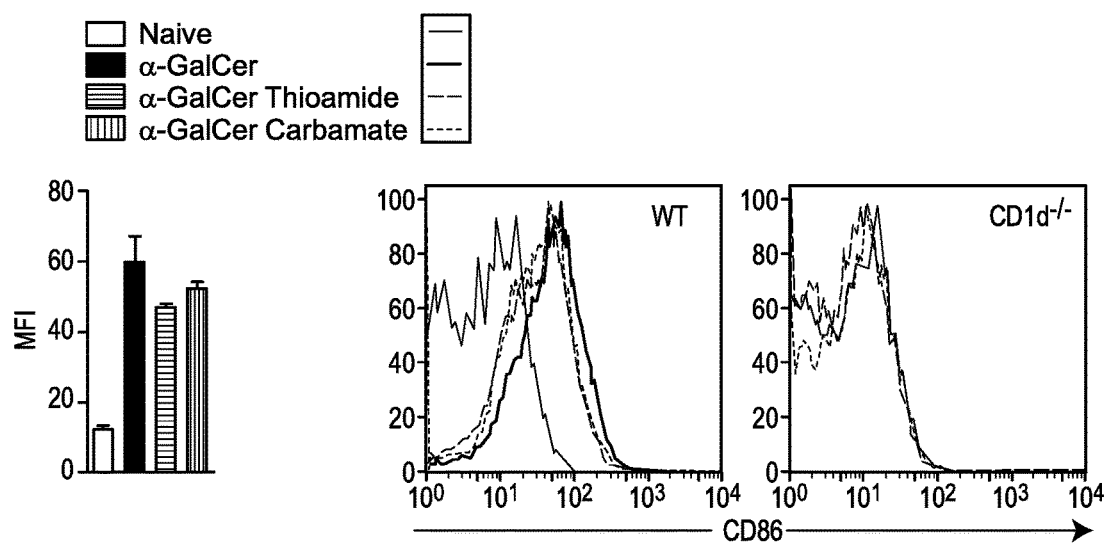
FIG. 4 shows fluorescence-activated cell sorting (FACS) analysis of cells harvested from the spleens of the mice in the experiment of FIG. 3, to determine the extent of dendritic cell (DC) maturation.

Disclosed herein are compounds having a general structure of formula (I):

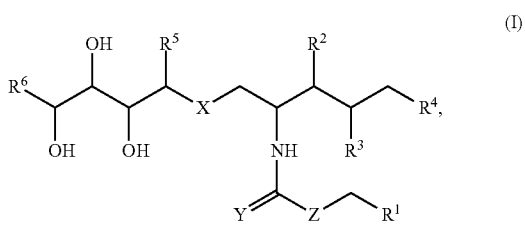

(I)

wherein $R^1$ is $C_5$-$C_{25}$ alkyl, $C_5$-$C_{25}$ alkenyl, $C_5$-$C_{25}$ alkynyl, $C_5$-$C_{25}$ heteroalkyl, $C_5$-$C_{25}$ heteroalkenyl, or $C_5$-$C_{25}$ heteroalkynyl; $R^2$ and $R^3$ are each independently selected from H, OH, SH, amino or substituted amino; $R^4$ is $C_5$-$C_{20}$ alkyl, $C_5$-$C_{20}$ alkenyl, $C_5$-$C_{20}$ alkynyl, $C_5$-$C_{20}$ heteroalkyl, $C_5$-$C_{20}$ heteroalkenyl, or $C_5$-$C_{20}$ heteroalkynyl; $R^6$ and $R^5$ are each independently selected from H, alkyl, and alkenyl, or $R^6$ and $R^5$ together form a 6-, 7-, or 8-membered cycloalkyl or cycloalkenyl ring; X is O, S, $SO_2$, SO(NH), SO(N(alkyl)), NH, N(alkyl), or $CH_2$; Y is O, NH, N(alkyl), or S; Z is O, S, NH, N(alkyl), or $CH_2$; with the proviso that (a) when Y and X are each O and $R^5$ and $R^6$ are each H, Z is not $CH_2$; and (b) when Y is O, $R^6$ and $R^5$ together form a 6-membered cycloalkyl ring, and Z is $CH_2$, the cycloalkyl ring is not substituted with $-CH_2OH$, $-OH$, $-CH_3$, or $-CH_2OCH_3$, or a salt, ester, solvate, or hydrate thereof.

The compounds disclosed herein can stimulate iNKT cells. In various cases, the compounds stimulate iNKT cells, as measured by an in vitro assay using hydridoma DN32 cells. In various cases, the compounds stimulate iNKT cells, as measured by an in vitro assay using human iNKT cells co-cultured with C1R-hCD1d cells. In various cases, the compounds stimulate iNKT cells in vivo.

In some embodiments, the compounds disclosed herein have a structure (IA), (IB), (IC), or (ID):

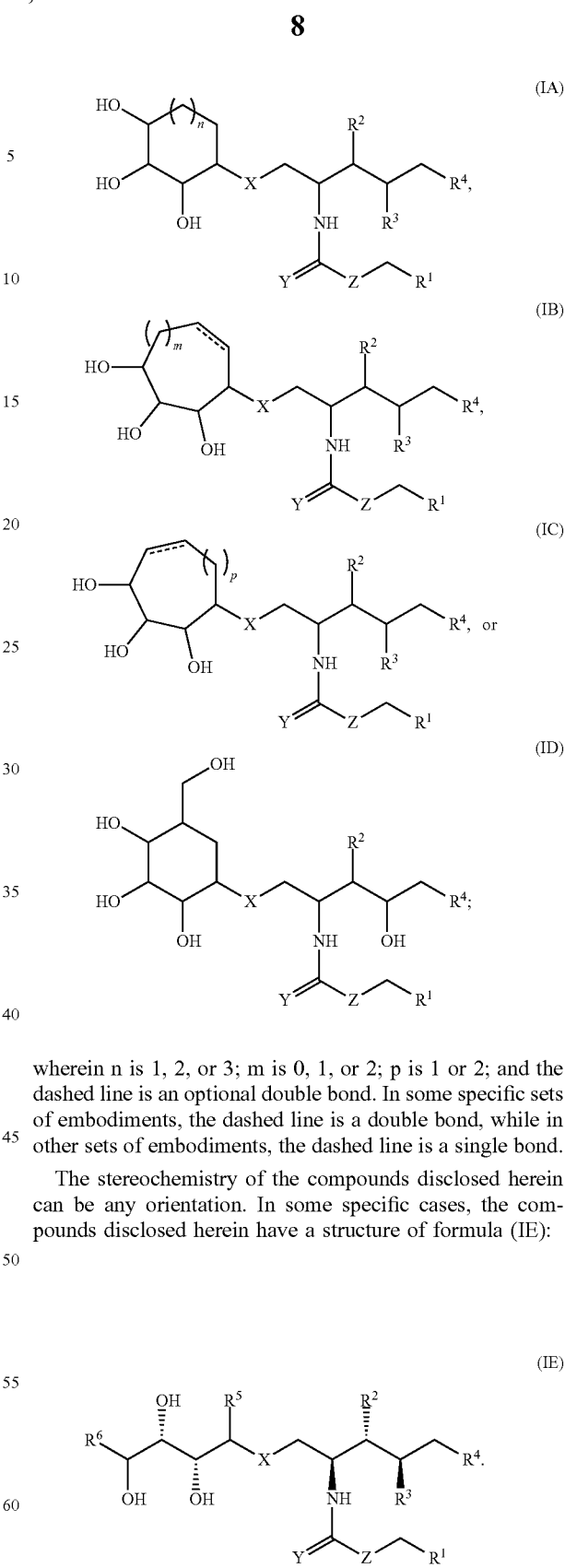

wherein n is 1, 2, or 3; m is 0, 1, or 2; p is 1 or 2; and the dashed line is an optional double bond. In some specific sets of embodiments, the dashed line is a double bond, while in other sets of embodiments, the dashed line is a single bond.

The stereochemistry of the compounds disclosed herein can be any orientation. In some specific cases, the compounds disclosed herein have a structure of formula (IE):

(IE)

Specifically excluded from the compounds of formula (I) disclosed herein are compounds having the following structures:

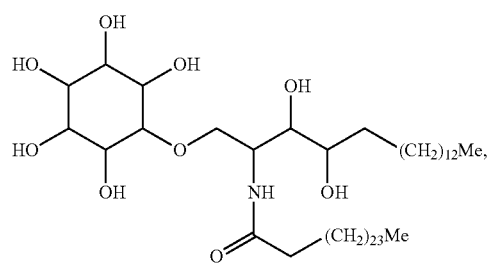
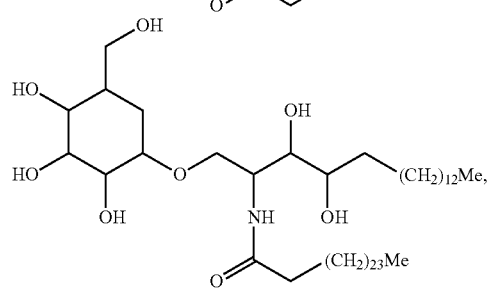
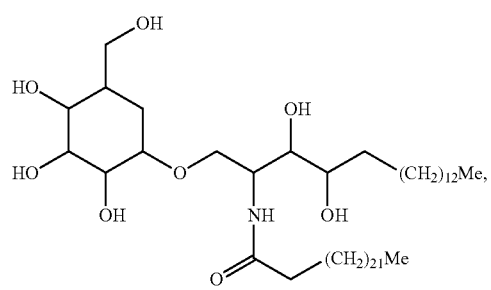
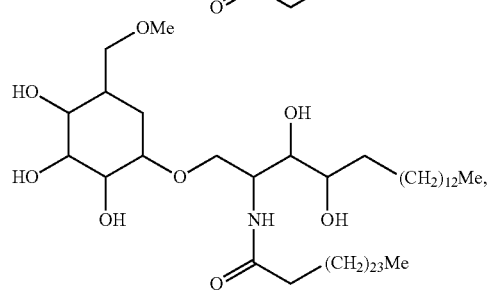
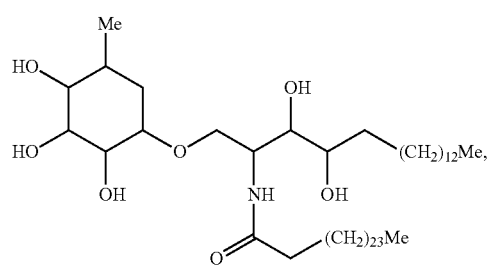
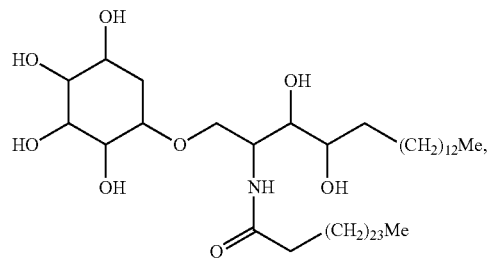
-continued
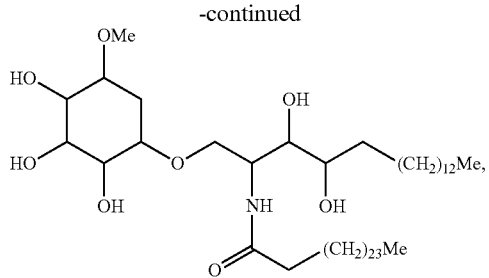
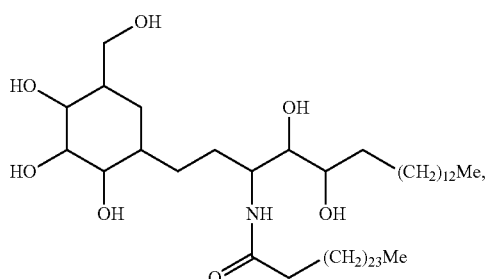
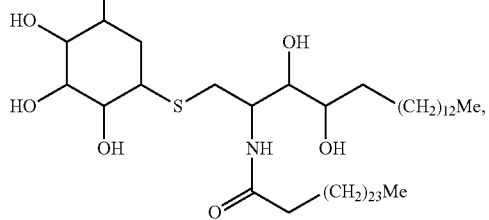
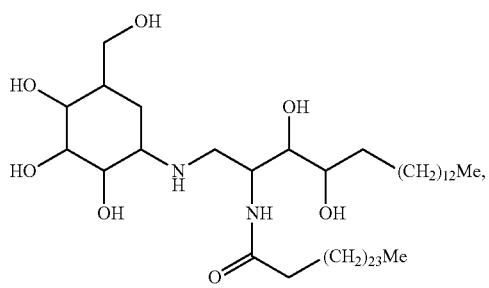
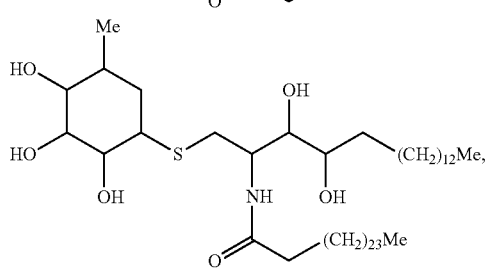
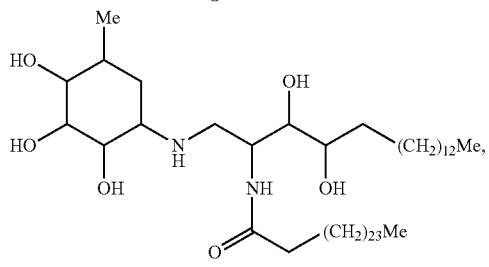

-continued
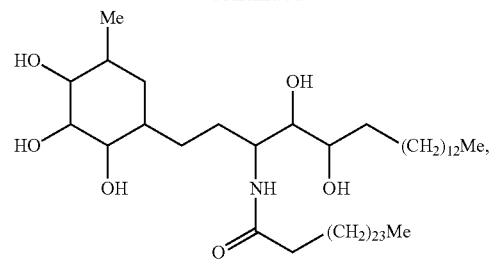
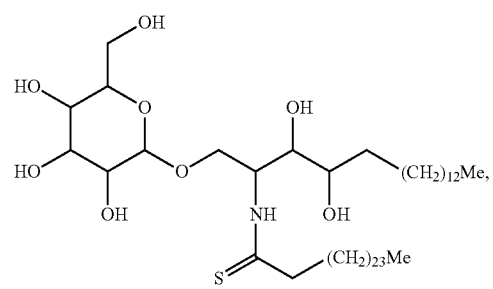
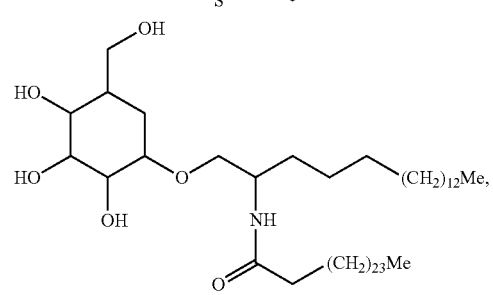
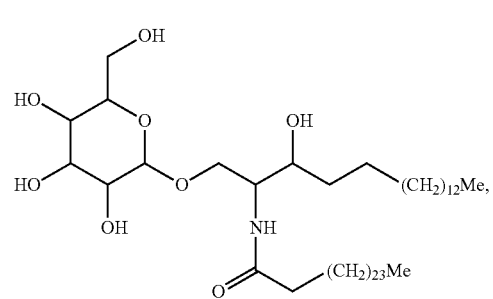
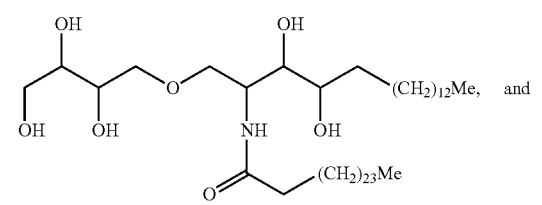 and
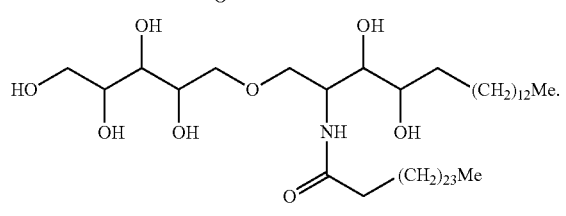
Specific compounds disclosed herein include
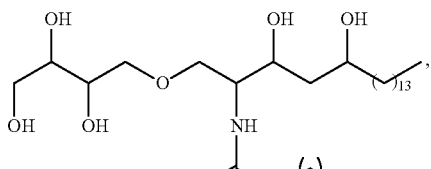
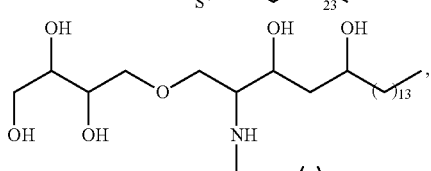
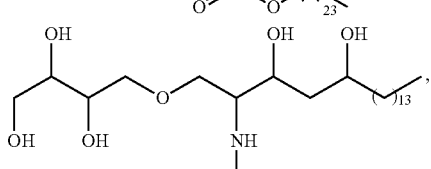
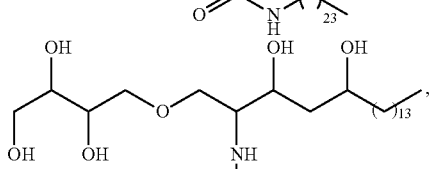
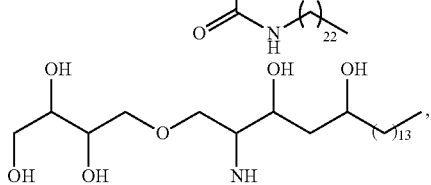
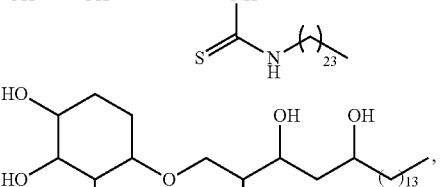
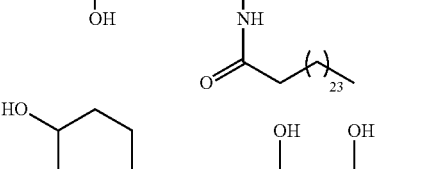
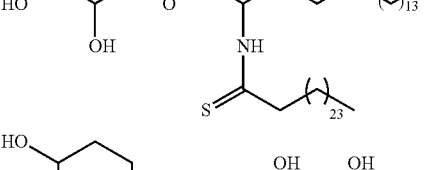
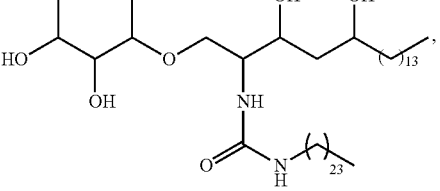

13
-continued
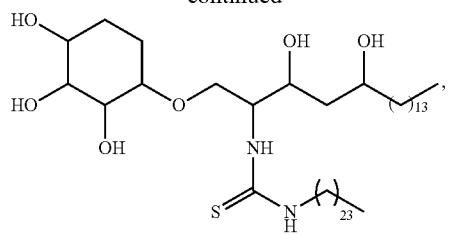
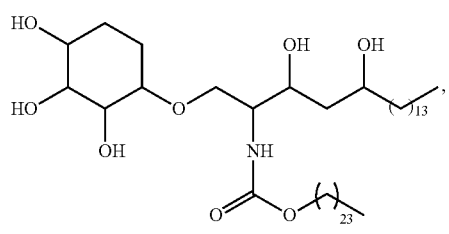
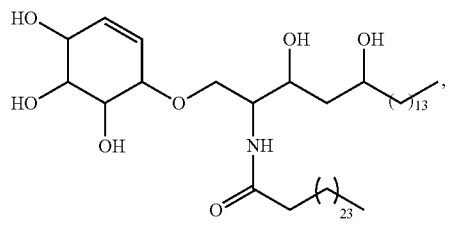
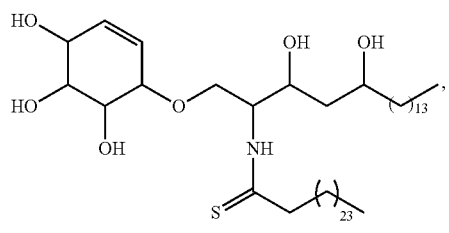
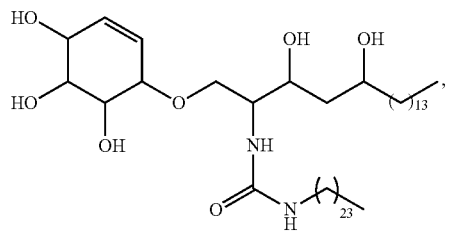
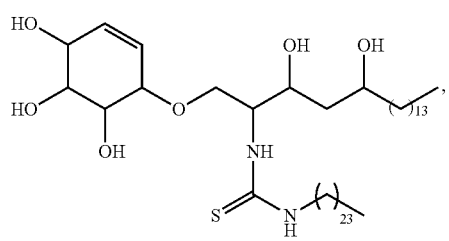
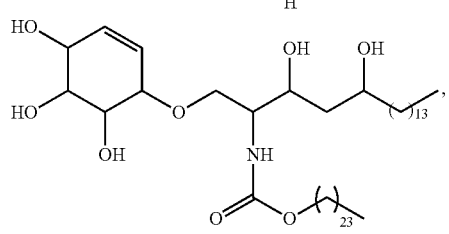
14
-continued
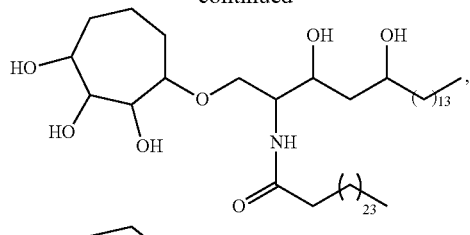
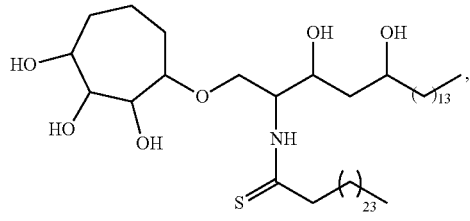
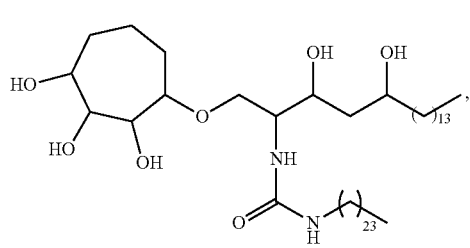
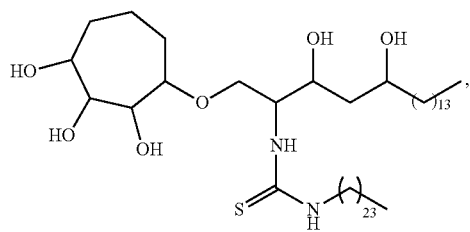
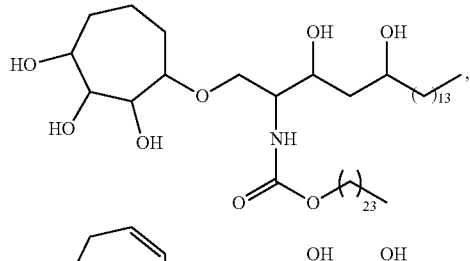
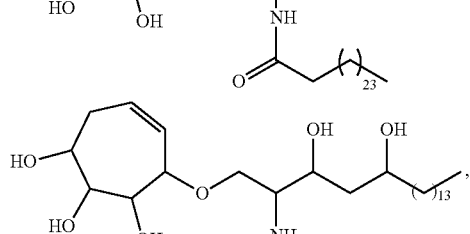

-continued

-continued

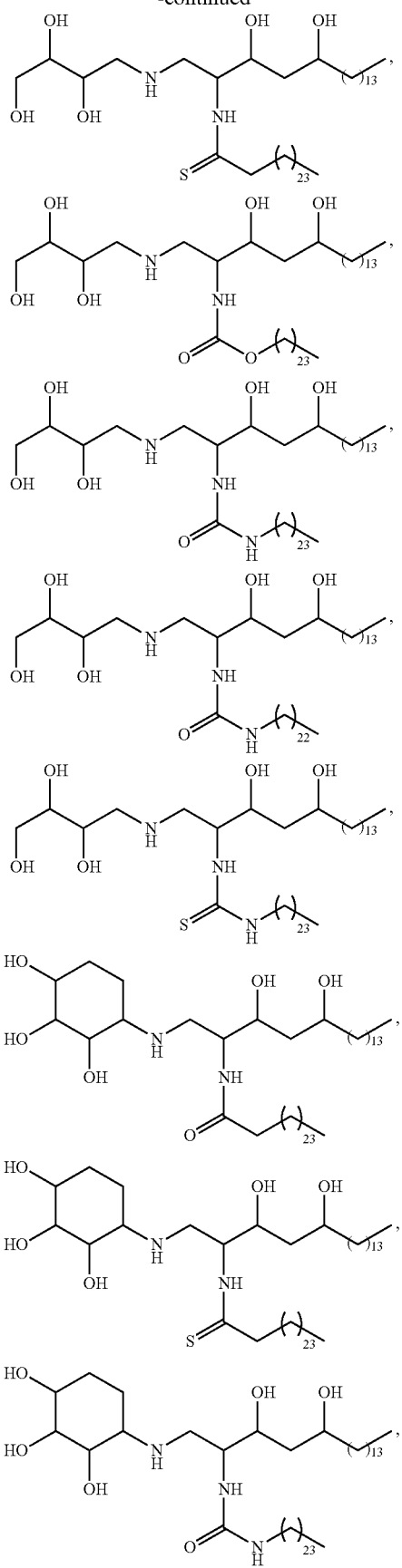
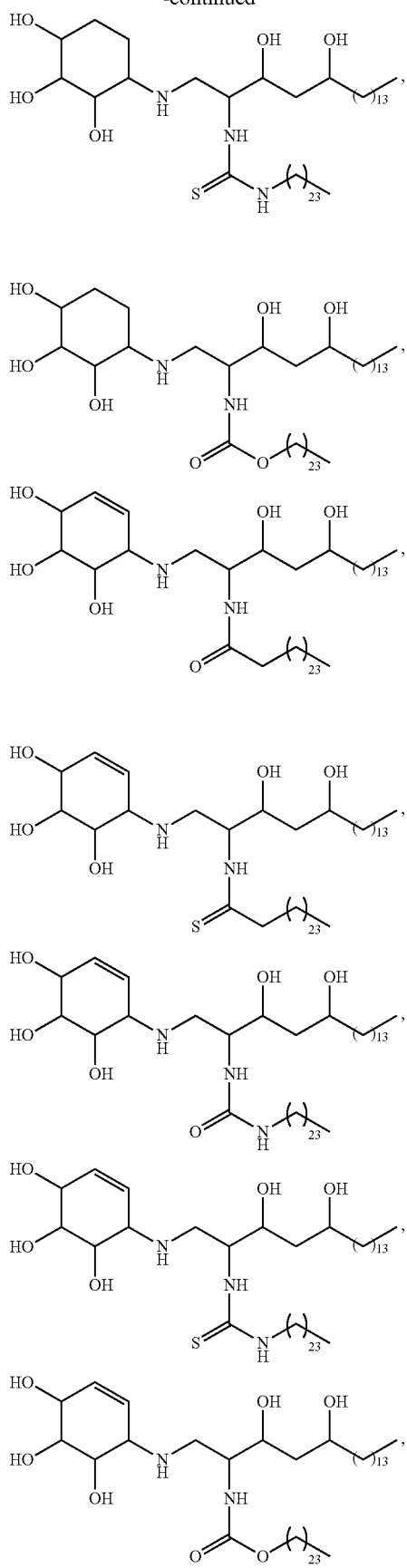

-continued

23
-continued
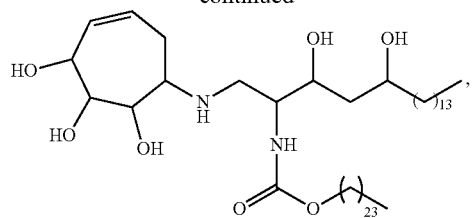
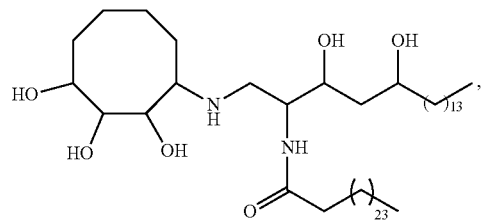
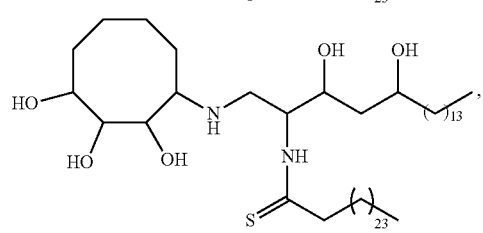
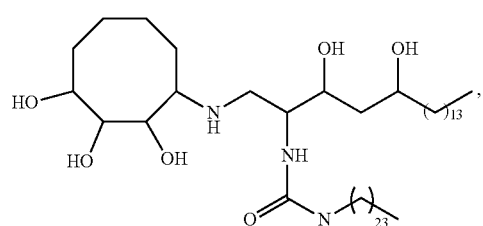
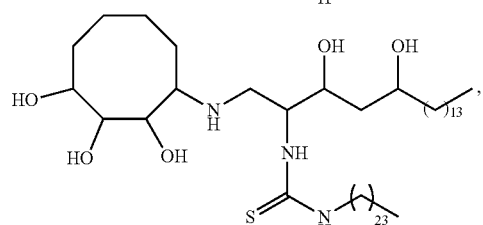
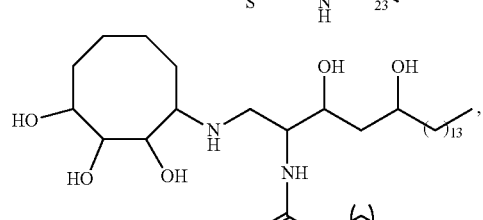
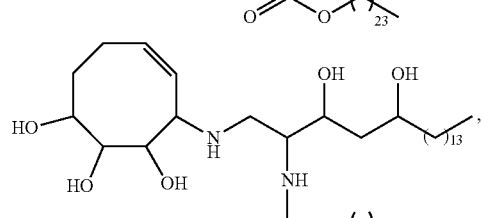
24
-continued
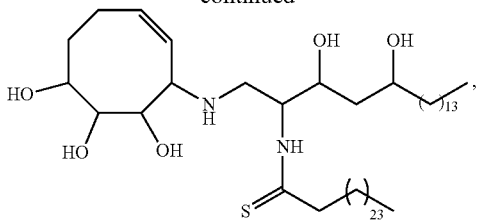
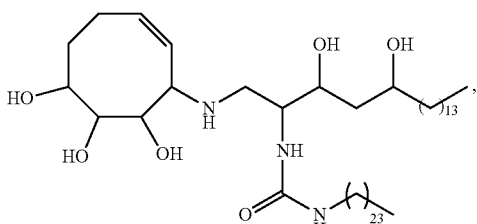
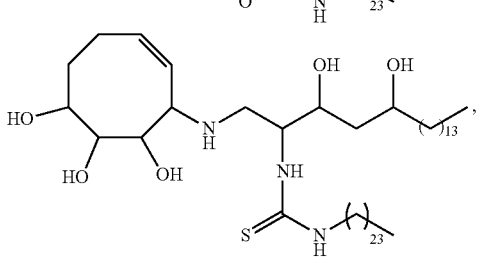
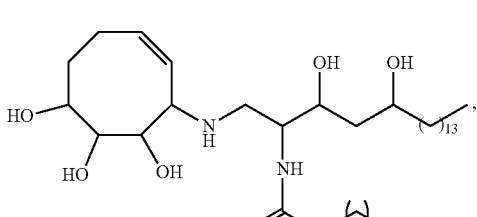
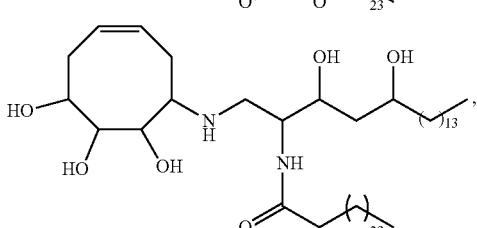
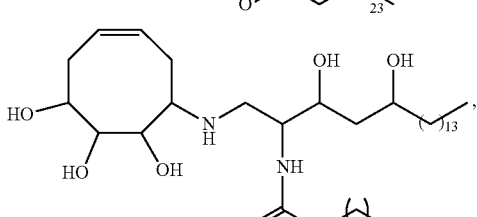
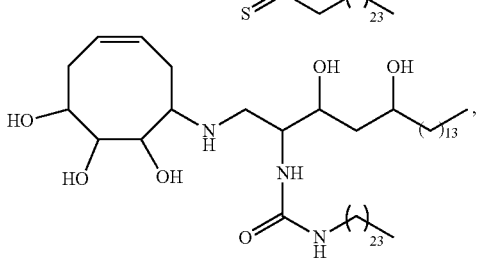

-continued
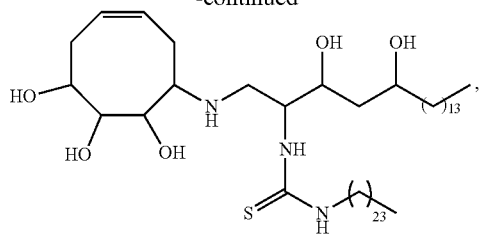
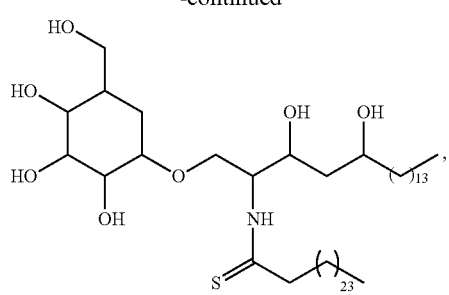
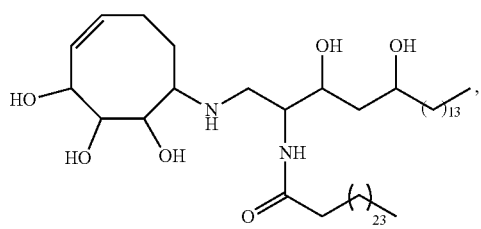
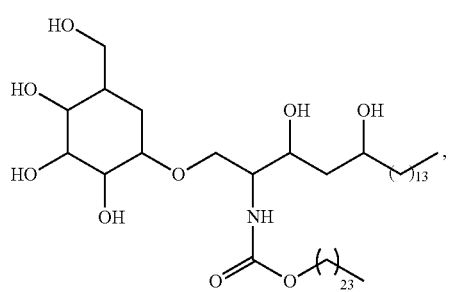
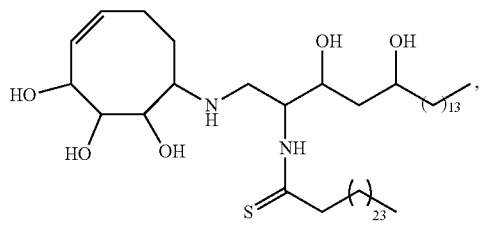
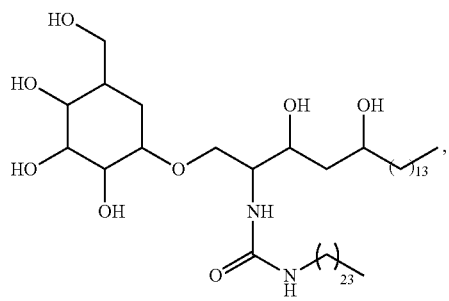
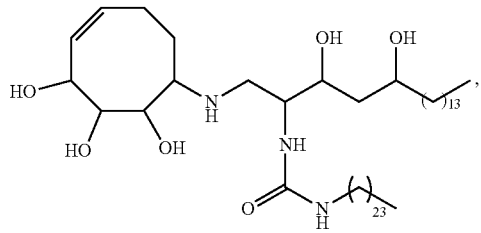
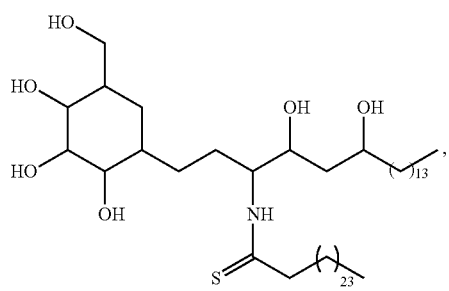
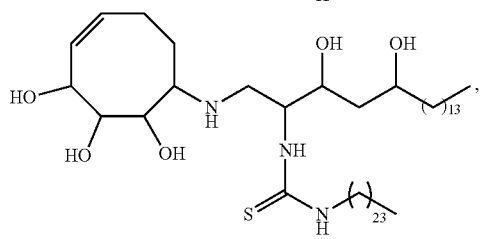
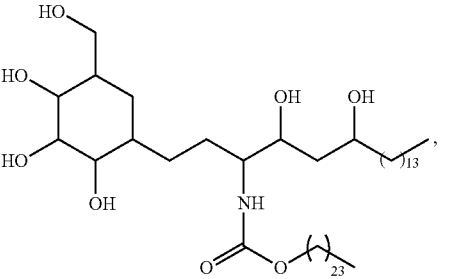
, and
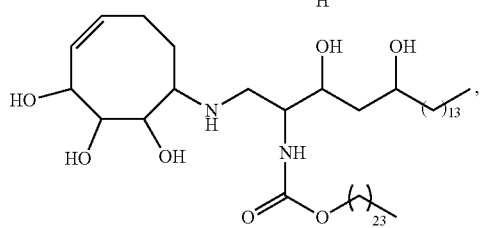

-continued

[chemical structure]

The term "alkyl" used herein refers to a saturated or unsaturated straight or branched chain hydrocarbon group of one to forty carbon atoms, including, but not limited to, methyl, ethyl, n-propyl, isopropyl, n-butyl, isobutyl, tert-butyl, n-hexyl, and the like. Alkyls of one to six carbon atoms are also contemplated. The term "alkyl" includes "bridged alkyl," i.e., a bicyclic or polycyclic hydrocarbon group, for example, norbornyl, adamantyl, bicyclo[2.2.2]octyl, bicyclo[2.2.1]heptyl, bicyclo[3.2.1]octyl, or decahydronaphthyl. Alkyl groups optionally can be substituted, for example, with hydroxy (OH), halide, thiol (SH), aryl, heteroaryl, cycloalkyl, heterocycloalkyl, and amino. It is specifically contemplated that in the compounds described herein the alkyl group consists of 1-40 carbon atoms, preferably 1-25 carbon atoms, preferably 1-15 carbon atoms, preferably 1-12 carbon atoms, preferably 1-10 carbon atoms, preferably 1-8 carbon atoms, and preferably 1-6 carbon atoms. A "heteroalkyl" group refers to an alkyl group having one or more of N, S, and O.

The term "cycloalkyl" used herein refers to a hydrocarbon group arranged in a ring. The cycloalkyl group can be substituted with one or more substituents, such as alkyl, halo, OH, SH, amino, substituted amino, carboxy, aryl, or heteroaryl. Examples of cycloalkyl groups include cyclopropyl, cyclobutyl, cyclopentyl, cyclohexyl, cycloheptyl, cyclooctyl, cylcononyl, and cyclodecyl. The term "heterocycloalkyl" refers to a cycloalkyl group having one or more of N, S, and O.

The term "alkenyl" used herein refers to a straight or branched chain hydrocarbon group of two to ten carbon atoms containing at least one carbon double bond including, but not limited to, 1-propenyl, 2-propenyl, 2-methyl-1-propenyl, 1-butenyl, 2-butenyl, and the like. The term "cycloalkenyl" refers to a cycloalkyl group having one or more double bonds. A "heteroalkenyl" group refers to an alkenyl group having one or more of N, S, and O.

The term "alkynyl" used herein refers to a straight or branched chain hydrocarbon group of two to ten carbon atoms containing at least one carbon triple bond including, but not limited to, 1-propynyl, 2-propynyl, 1-butyryl, 2-butyryl, and the like. A "heteroalkynyl" group refers to an alkynyl group having one or more of N, S, and O.

The term "alkylene" used herein refers to an alkyl group having a substituent. For example, the term "alkylene aryl" refers to an alkyl group substituted with an aryl group. The alkylene group is optionally substituted with one or more substituent previously listed as an optional alkyl substituent. For example, an alkylene group can be $-CH_2CH_2-$ or $-CH_2-$.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $CF_3$, $NO_2$, CN, NC, OH, alkoxy, amino, $CO_2H$, $CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, $CF_3$, $NO_2$, CN, NC, OH, alkoxy, amino, $CO_2H$, $CO_2$alkyl, aryl, and heteroaryl. In some cases, the heteroaryl group is substituted with one or more of alkyl and alkoxy groups. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term "amino" as used herein refers to $-NR_2$, where R is independently hydrogen, optionally substituted alkyl, optionally substituted heteroalkyl, optionally substituted cycloalkyl, optionally substituted heterocycloalkyl, optionally substituted aryl or optionally substituted heteroaryl. Non-limiting examples of amino groups include $NH_2$, $NH(CH_3)$, and $N(CH_3)_2$. In some cases, R is independently hydrogen or alkyl.

The term "carboxy" or "carboxyl" used herein refers to $-COOH$ or its deprotonated form $-COO^-$. $C_{1-10}$carboxy refers to optionally substituted alkyl or alkenyl groups having a carboxy moiety. Examples include, but are not limited to, $-CH_2COOH$, $-CH_2CH(COOH)CH_3$, and $-CH_2CH_2CH_2COOH$.

In some cases, the substituent group(s) is (are) one or more group(s) individually and independently selected from alkyl, cycloalkyl, aryl, heterocyclyl, heteroaryl, hydroxy, alkoxy, aryloxy, mercapto, alkylthio, arylthio, cyano, halo, carbonyl, thiocarbonyl, alkoxycarbonyl, nitro, silyl, trihalomethanesulfonyl, trifluoromethyl, and amino, including mono- and di-substituted amino groups, and the protected derivatives thereof.

Asymmetric carbon atoms can be present. All such isomers, including diastereomers and enantiomers, as well as the mixtures thereof, are intended to be included in the scope of the disclosure herein. In certain cases, compounds can exist in tautomeric forms. All tautomeric forms are intended to be included in the scope of the disclosure herein. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated.

The salts, e.g., pharmaceutically acceptable salts, of the disclosed therapeutics may be prepared by reacting the appropriate base or acid with a stoichiometric equivalent of the therapeutic.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Similarly, pharmaceutically acceptable derivatives (e.g., esters), metabolites, hydrates, solvates and prodrugs of the therapeutic may be prepared by methods generally known to those skilled in the art. Thus, another embodiment provides compounds that are prodrugs of an active compound. In general, a prodrug is a compound which is metabolized in vivo (e.g., by a metabolic transformation such as deamination, dealkylation, de-esterification, and the like) to provide an active compound. A "pharmaceutically acceptable prodrug" means a compound which is, within the scope of sound medical judgment, suitable for pharmaceutical use in a patient without undue toxicity, irritation, allergic response, and the like, and effective for the intended use, including a pharmaceutically acceptable ester as well as a zwitterionic form, where possible, of the therapeutic. As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates. Examples of pharmaceutically-acceptable prodrug types are described in Higuchi and Stella, *Pro-drugs as Novel Delivery Systems*, Vol. 14 of the A.C.S. Symposium Series, and in Roche, ed., *Bioreversible Carriers in Drug Design*, American Pharmaceutical Association and Pergamon Press, 1987, both of which are incorporated herein by reference.

The compounds and compositions described herein may also include metabolites. As used herein, the term "metabolite" means a product of metabolism of a compound of the embodiments or a pharmaceutically acceptable salt, analog, or derivative thereof, that exhibits a similar activity in vitro or in vivo to a disclosed therapeutic. The compounds and compositions described herein may also include hydrates and solvates. As used herein, the term "solvate" refers to a complex formed by a solute (herein, the therapeutic) and a solvent. Such solvents for the purpose of the embodiments preferably should not negatively interfere with the biological activity of the solute. Solvents may be, by way of example, water, ethanol, or acetic acid.

Synthesis of Compounds

The compounds described herein can be synthesized using any means known to the synthetic organic chemist. Described below are synthetic schemes for synthesizing several of the compounds as disclosed herein, and can be used as guidance on synthesis of the compounds disclosed herein.

The completely selective formation of α-galactosides has traditionally been difficult; however in recent years some excellent solutions to this problem have been developed. The Nishida and Kobayashi's dehydrative glycosylation methodology was employed; thus reaction of 2,3,4,6-tetra-O-benzyl-galactose 14 with $CBr_4/PPh_3$ afforded the corresponding galactosyl bromide, which was reacted in situ with acceptor 15, in the presence of tetramethylurea (TMU) and $Bu_4NBr$, to provide a good yield of the desired galactoside 16 as a single α-anomer (Scheme 1). Staudinger reduction of the azide in 16 with $PMe_3$ in wet THF afforded amine 17, which reacted with hexacosanoyl chloride to provide amide 18 in an unoptimized 40% yield from azide 16. Formation of the corresponding urea 19 from amine 17 required the synthesis of an appropriate isocyanate, formed by a Curtius rearrangement on the corresponding acid azide. Use of hexacosanoic acid as the starting point would lead to a urea product containing 27 atoms (26 carbons and one nitrogen) in the acyl chain. The hydrophobic A' binding pocket in CD1d optimally accommodates an acyl chain length containing 26 carbon atoms. So, tetracosanoic acid was used as this would be processed through to a urea product containing 25 atoms in the acyl chain (24 carbons and one nitrogen). Since the α-GalCer analogue containing a C24 acyl chain displays similar biological activity to α-GalCer containing a C26 chain, differences in biological activity between a ureido analogue containing 25 atoms in the acyl chain (i.e. 7), and α-GalCer would be a attributable to an amide-urea switch and not a result of the slightly truncated alkyl chain length. Tricosanyl isocyanate was duly prepared from tetracosanoic acid in three steps. Treatment of tetracosanoyl chloride with $NaN_3$ afforded the corresponding acid azide, which underwent Curtius rearrangement on heating in toluene at reflux to provide tricosanyl isocyanate. Without purification, the isocyanate was reacted with amine 17 to provide urea 19 in 68% yield. Hydrogenolysis of the benzyl groups in amide 18 and urea 19 effected global deprotection and afforded urea 7, alongside α-GalCer 1, which would serve as the control in the biological studies (Scheme 1).

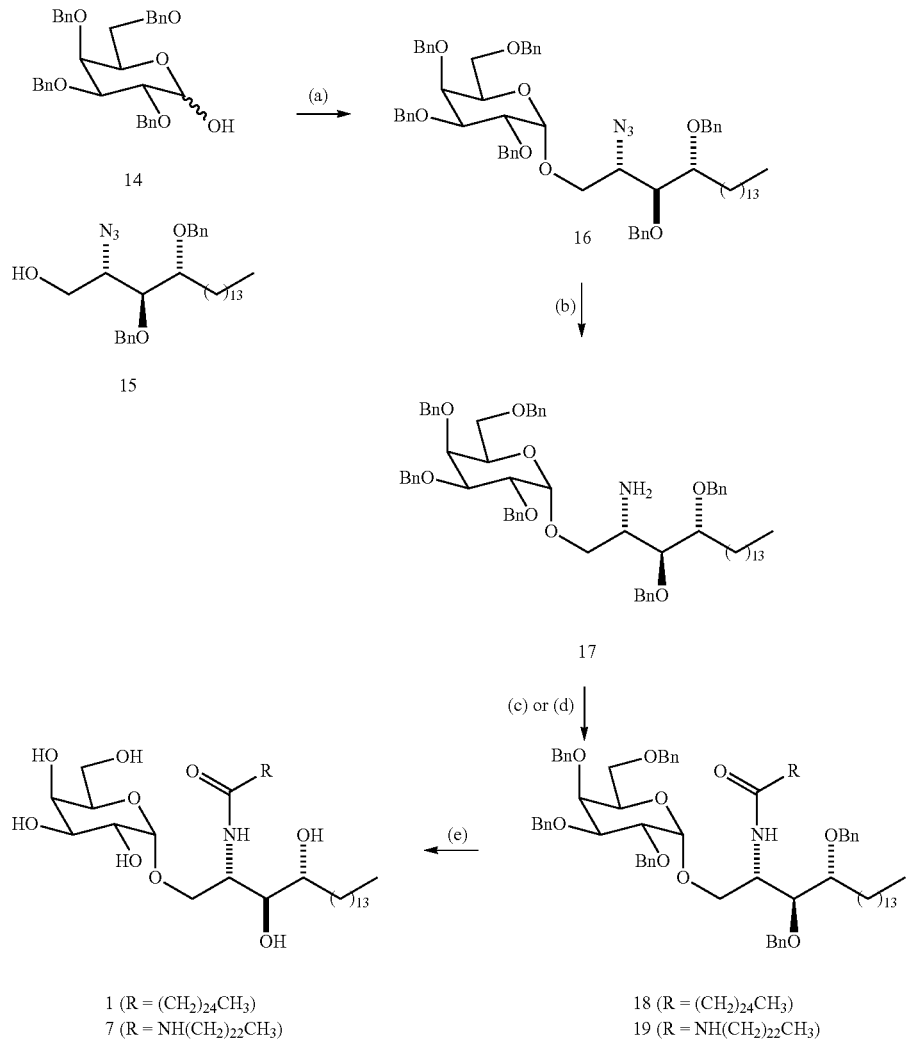

Synthesis of α-GalCer 1 and urea 7. (a) 14, PPh₃, CBr₄, CH₂Cl₂, r.t., 3 h; then Me₂C(O)NMe₂, Bu₄NBr, CH₂Cl₂; then 15, CH₂Cl₂, 3 Å MS, r.t., 3 d, 62%. (b) PMe₃, THF, r.t., 4 h, then H₂O, 1 h, 72%. (c) CH₃(CH₂)₂₄C(O)Cl, Et₃N, CH₂Cl₂, 0° C. to r.t., 8 h, 18 (54%). (d) CH₃(CH₂)₂₂NCO, toluene, reflux, 8 h, 19 (68%). (e) Pd(OH)₂/C, H₂, THF, r.t., 22 h: 1 (68% from 17); 7 (73% from 17).

While benzyl ethers are commonly employed protecting groups, particularly in carbohydrate chemistry, conformational effects can mean that some groups are particularly stubborn to remove. Indeed, this proved to be the case with one of the benzyl ethers in the phytosphingosine unit of amide 18 and urea 19; debenzylation was often slow, and frequently required filtration of the reaction mixture and addition of fresh catalyst to effect complete deprotection. To address this troublesome issue, a modified phytosphingosine acceptor was investigated in which the internal 1,2-diol was protected as an isopropylidene acetal. The use of an acetal to protect the internal 1,2-diol in phytosphingosine would likely necessitate a two-step deprotection post glycosylation; however a late-stage acetal hydrolysis was not problematic, and more importantly, the debenzylation step would be significantly easier. Moreover the additional deprotection step would be mitigated by its straightforward two-step synthesis from phytosphingosine, compared with the three-step synthesis required to access dibenzyl ether 15.

Although the choice of donor/acceptor pairs can impact on the stereoselectivity of glycosylation reactions, galactoside 20 could be accessed under standard conditions in similarly good yield and once again with complete α-stereoselectivity (Scheme 2). Subsequent Staudinger reduction provided amine 21, which was acylated as before to provide amide 22. Alternatively, reaction with a mixed carbonate, prepared from 1-tetracosanol and N,N'-disuccinimidyl carbonate provided carbamate 23. A two-step acetal hydrolysis/debenzylation sequence on 22 and 23 proceeded uneventfully in both cases, to provide α-GalCer and carbamate derivative 8, respectively. Finally the thioamide 6 was prepared from α-GalCer in a three-step sequence, involving peracetylation to provide 24, chemoselective thionation of the amide with Lawesson's reagent to afford thioamide 25, followed by deacetylation under Zémplen conditions (Scheme 2).

Scheme 2

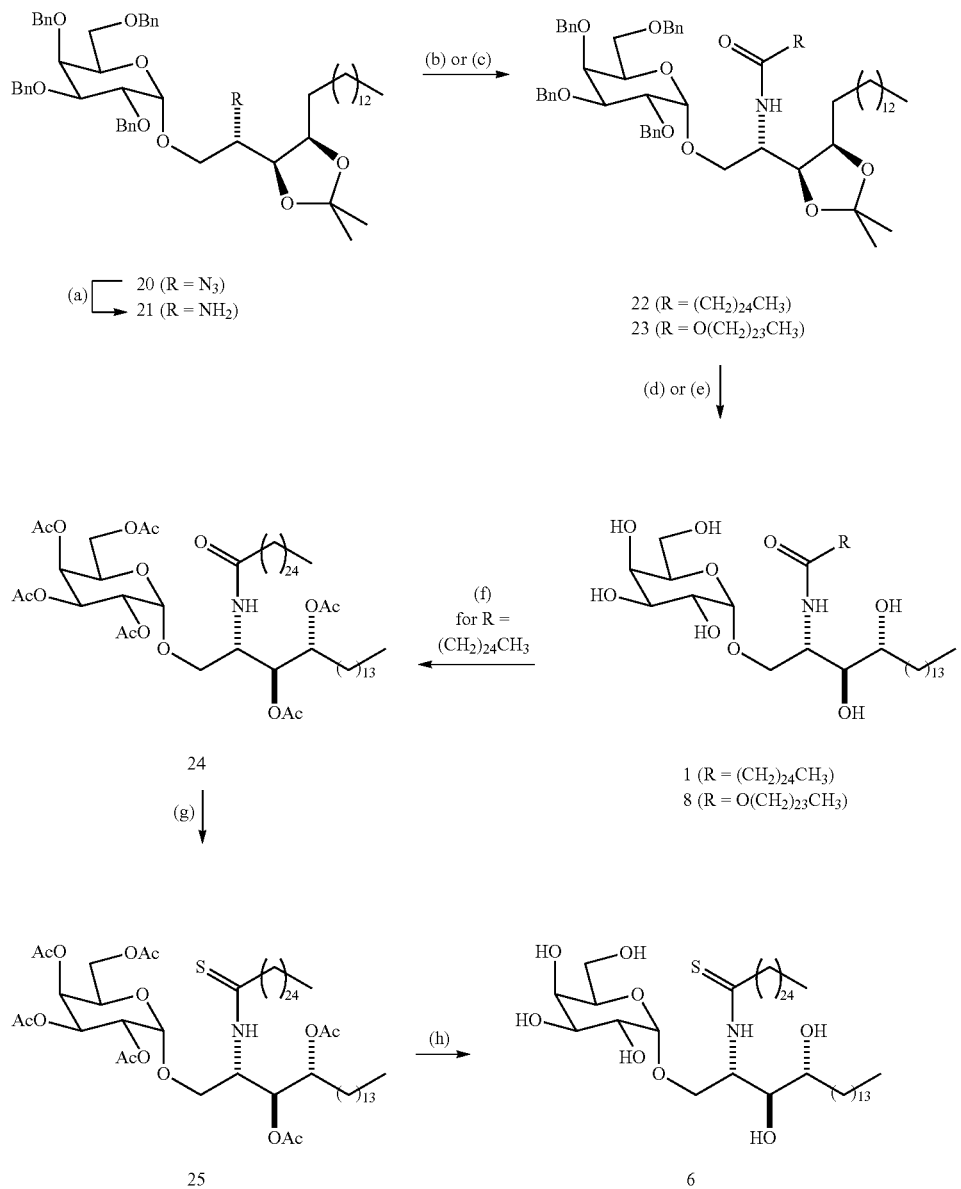

Improved synthesis of α-GalCer 1, and synthesis of carbamate 8 and thioamide 6. (a) PMe$_3$, THF, 3 h, r.t., then H$_2$O, 1 h, 93%. (b) CH$_3$(CH$_2$)$_{24}$C(O)Cl, Et$_3$N, CH$_2$Cl$_2$, 0° C. to r.t., 12 h, 22 (85%). (c) N-succinimidyl-tetracosanyl carbonate, Et$_3$N, CH$_2$Cl$_2$, r.t., 4 h, 23 (82%). (d) from 22: (i) TFA, CH$_2$Cl$_2$—H$_2$O, 10:1, 2 h, r.t.; (ii) Pd(OH)$_2$/C, H$_2$, THF, 6 h, 1 (75%). (e) from 23: (i) TFA, CH$_2$Cl$_2$-MeOH, 2:1, 2 h, r.t.; (ii) Pd(OH)$_2$/C, H$_2$, THF, 6 h, 8 (75%). (f) Ac$_2$O, pyridine, r.t., 10 h, 94%. (g) Lawesson's reagent, toluene, 80° C., 4 h, 85%. (h) NaOMe, MeOH, r.t., 2 h, 90%.

Synthesis of ThrCer 2 and its three analogues 9, 10 and 11 are described next. Ready access to an advanced intermediate, namely amine 26, using a slight modification of the previously established methodology alongside that developed for generating the three α-GalCer analogues, provided straightforward access to the corresponding ThrCer analogues as summarized in Scheme 3. ThrCer 2 was synthesized from amine 26 in a three-step sequence involving acylation, followed by silyl ether deprotection and acetal hydrolysis. Thionation of the acylation product 27 provided thioamide 28, which underwent the same two deprotection steps to afford the first ThrCer target, namely thioamide analogue 9. Alternatively, treatment of amine 26 with the mixed carbonate derived from the reaction of 1-tetracosanol with N,N'-disuccinimidyl carbonate, provided carbamate 29, and with tricosanyl isocyanate, furnished urea 30, and thence the final two targets, carbamate 11 and urea 10, after silyl deprotection and acetal hydrolysis (Scheme 3).

Scheme 3

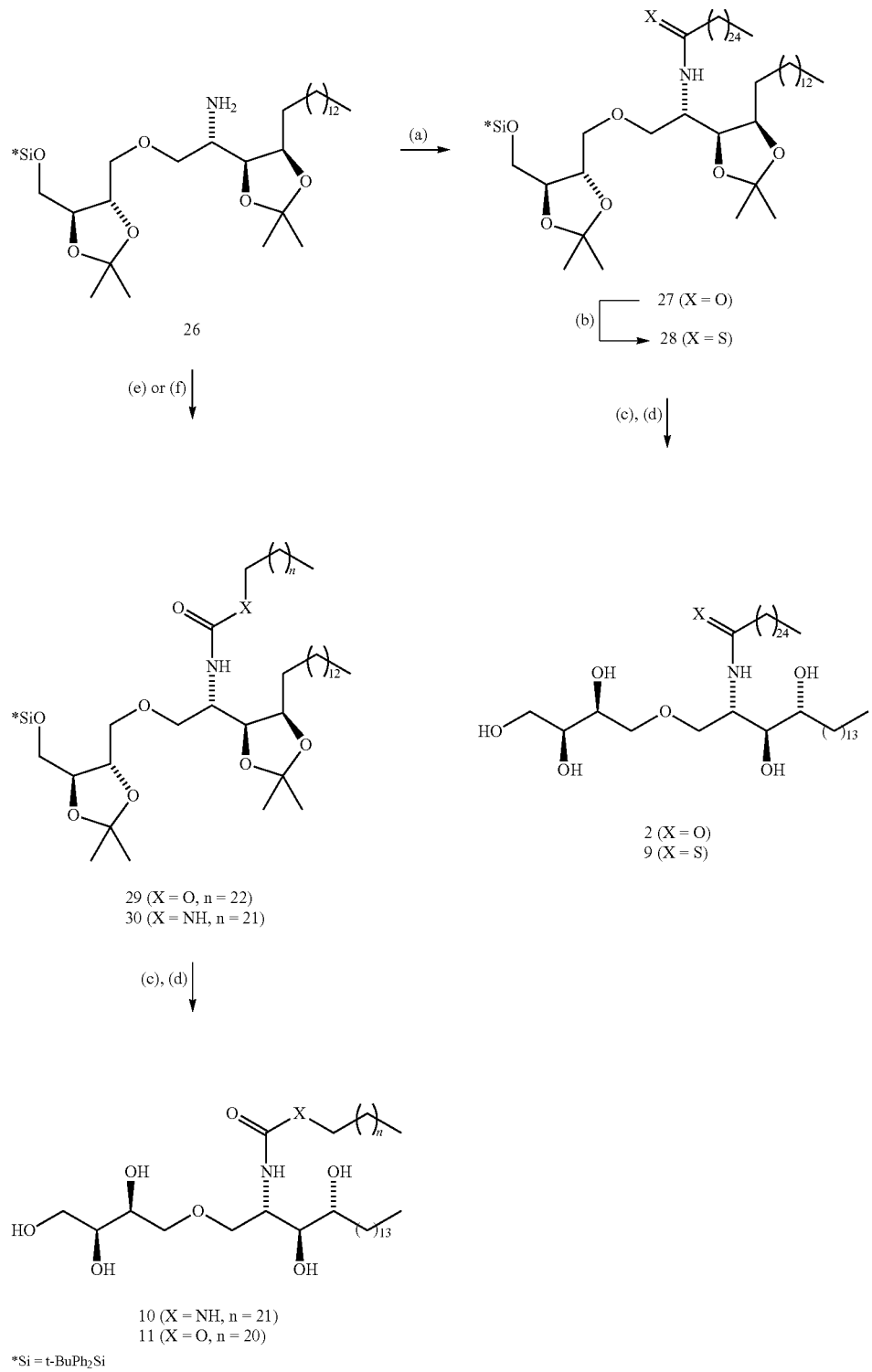

Synthesis of ThrCer 2 and thioamide, urea and carbamate analogues. (a) $CH_3(CH_2)_{24}C(O)Cl$, $Et_3N$, $CH_2Cl_2$, 0° C. to r.t., 12 h, 85%. (b) Lawesson's reagent, toluene, 80° C., 5 h, 88%. (c) $Bu_4NF$, THF, r.t., 4 h. (d) TFA, $CH_2Cl_2$-MeOH (10:1), r.t.; 2 (74% from 27); 9 (73% from 28); 10 (72% from 30); 11 (70% from 29). (e) N-succinimidyl-tetracosanyl carbonate, $Et_3N$, $CH_2Cl_2$, r.t., 5 h, 29 (86%). (f) $CH_3(CH_2)_{24}NCO$, toluene, reflux, 8 h, 30 (80%).

Scheme 4 shows a general synthesis for preparing sulfamidate compounds as disclosed herein.

Scheme 4
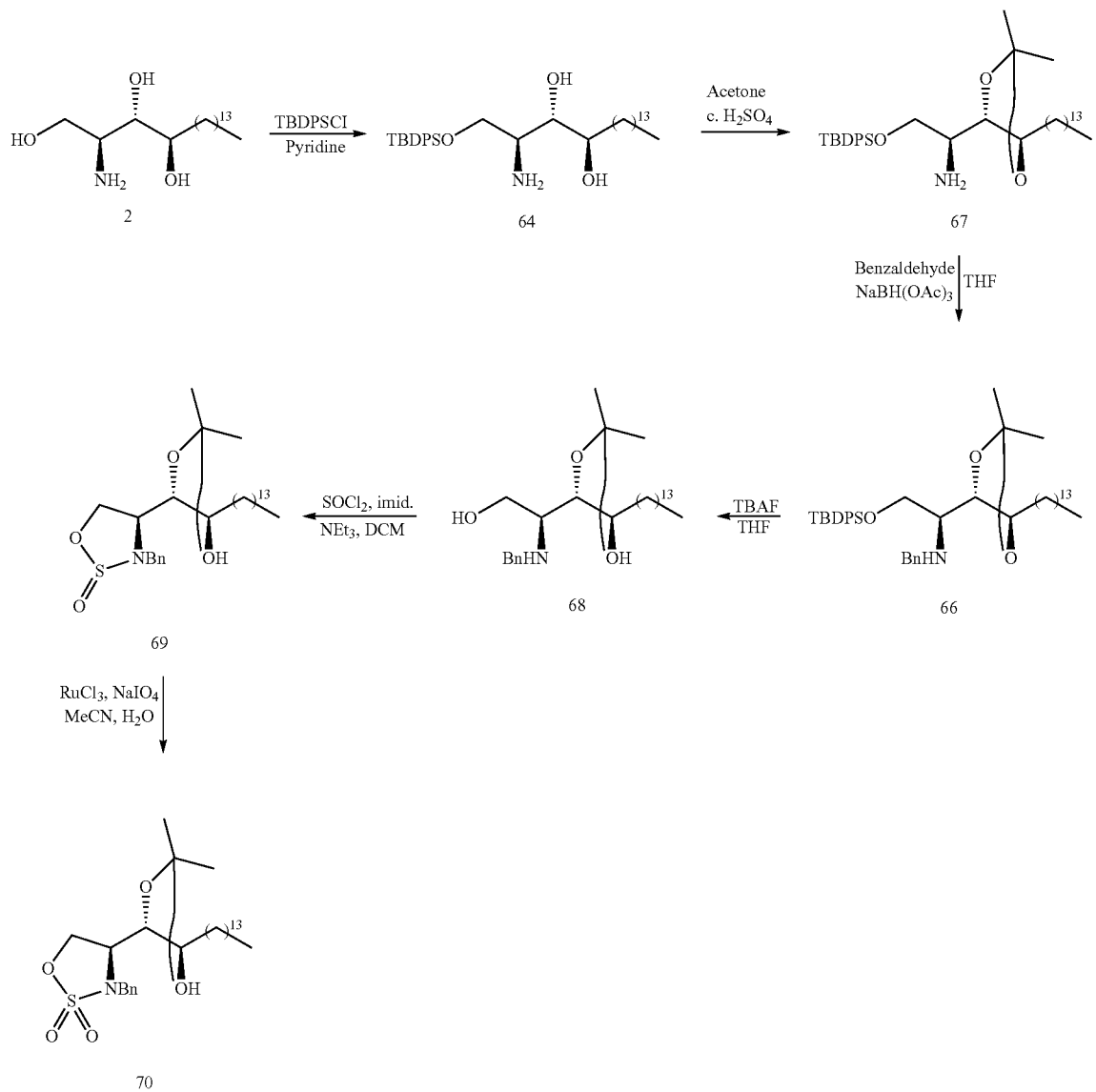
Scheme 5 shows a general synthesis for preparing seven-membered ring compounds as disclosed herein.
Scheme 5
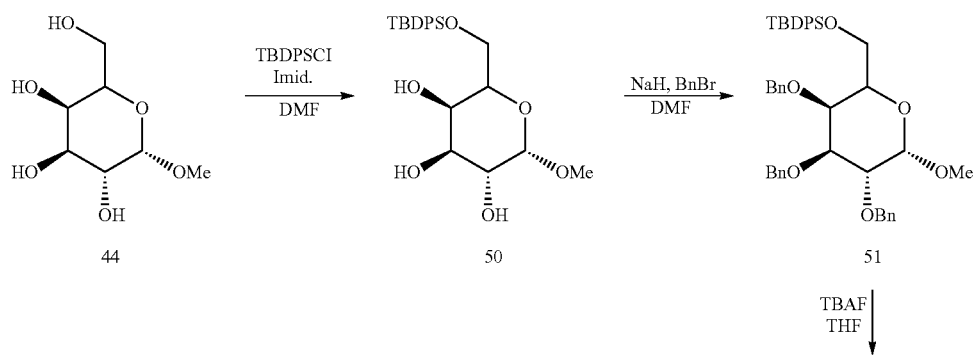

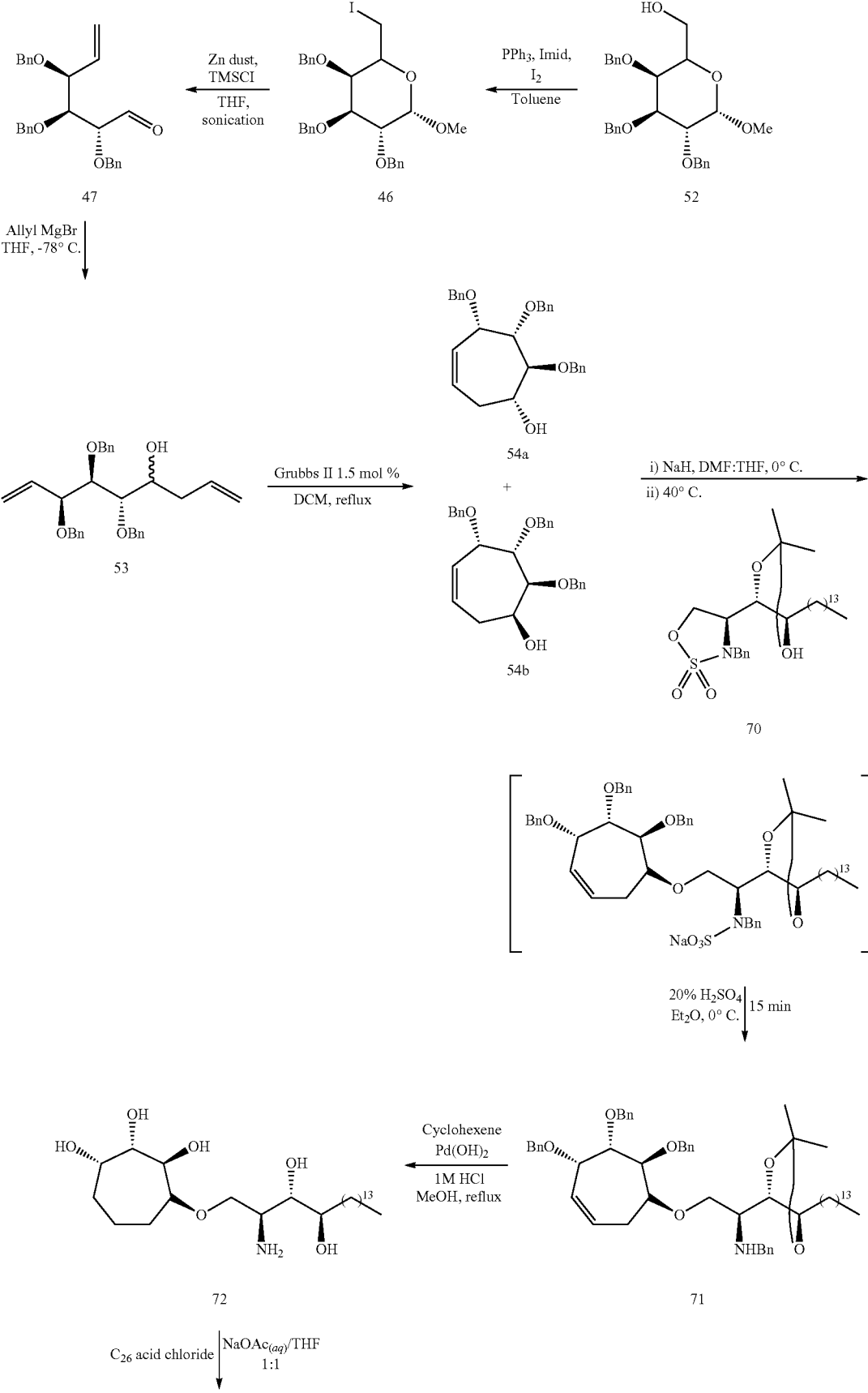

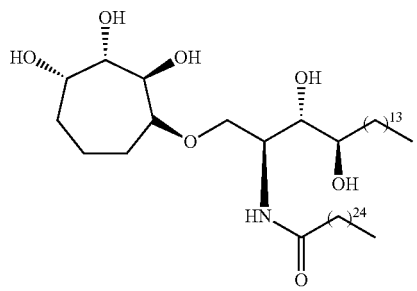
Scheme 6 shows a general synthesis for preparing six-membered ring compounds as disclosed herein.
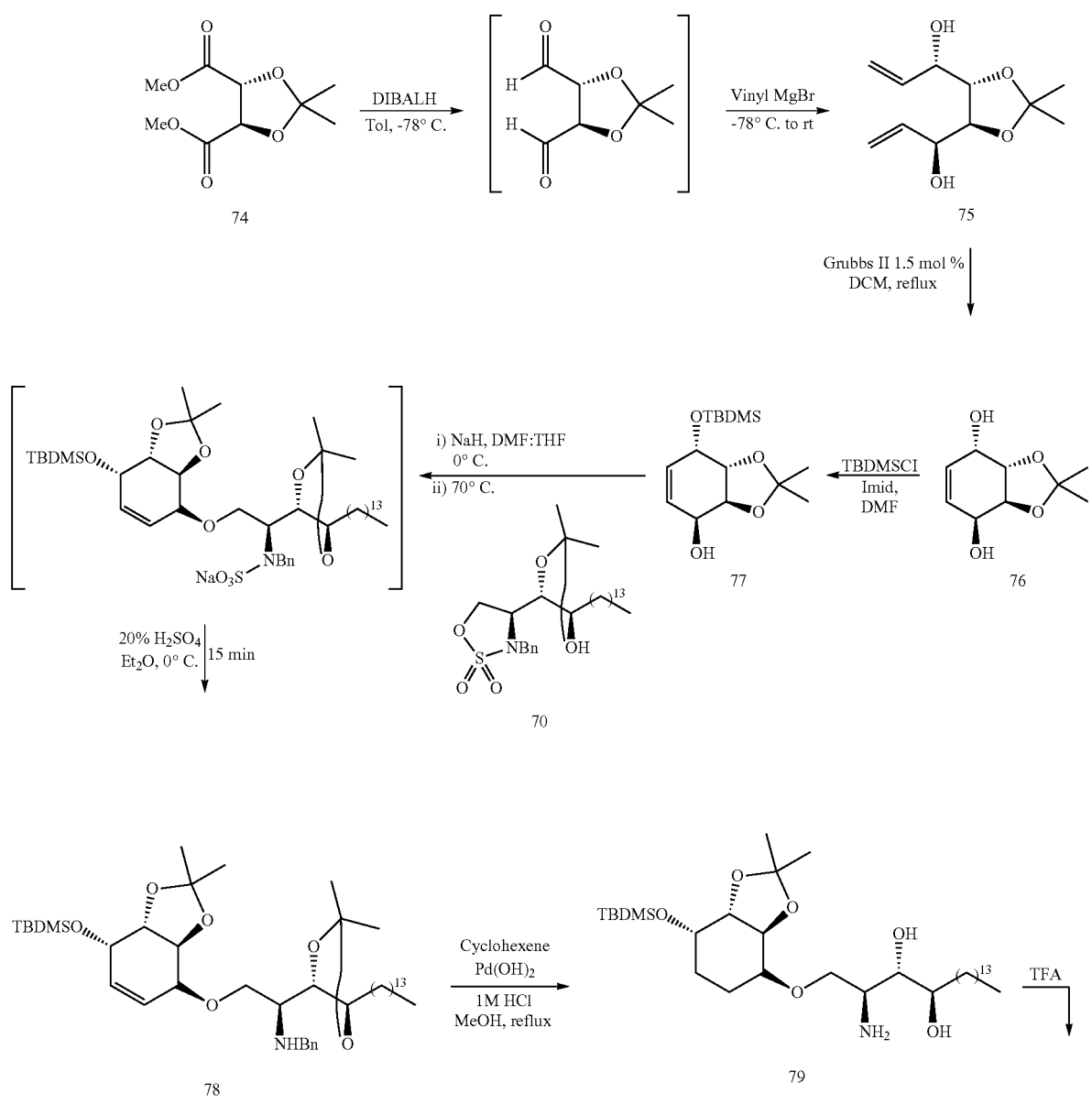

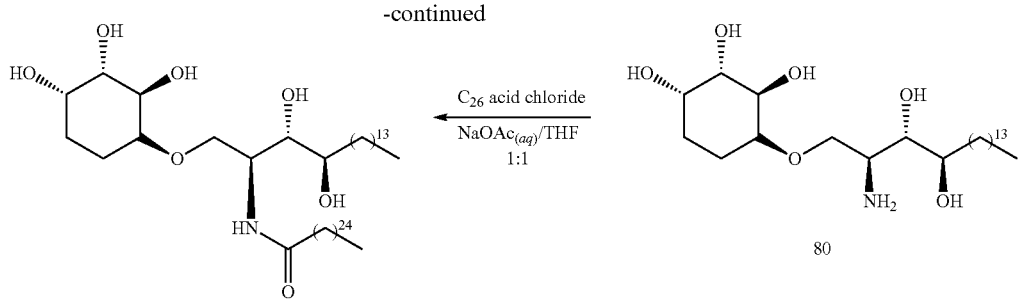
Scheme 7 shows a general synthesis for preparing eight-membered ring compounds as disclosed herein.
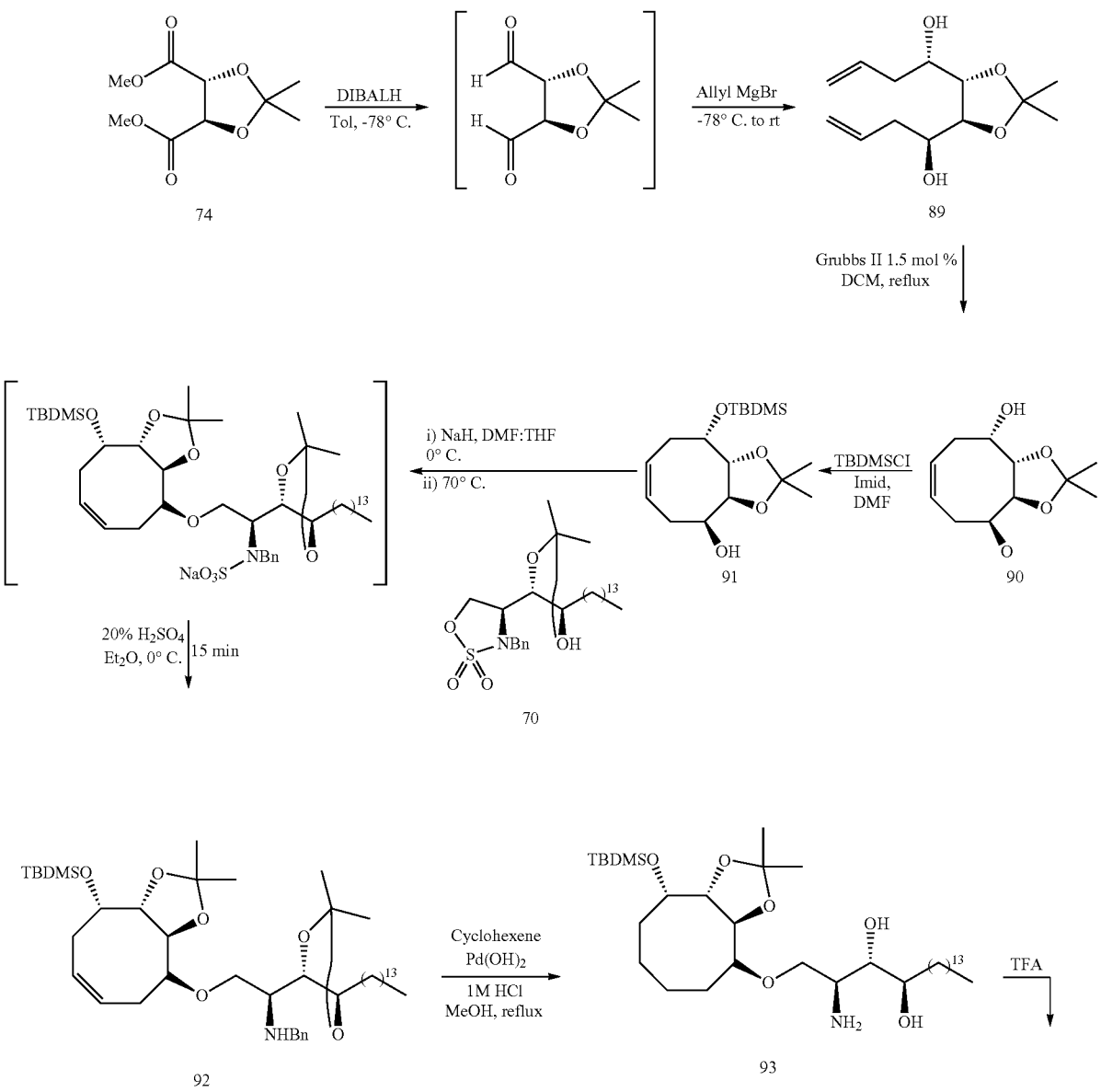

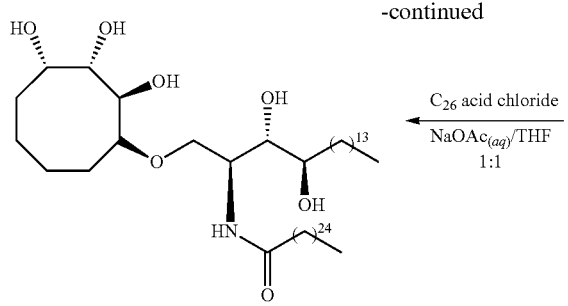
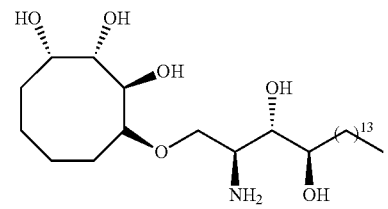

95 → 94

Pharmaceutical Formulations and Routes of Administration

As herein, the compounds described herein may be formulated in pharmaceutical compositions with a pharmaceutically acceptable excipient. The compound or composition comprising the compound is administered by any route that permits treatment of the disease or condition.

One route of administration is oral administration. Additionally, the compound or composition comprising the compound may be delivered to a patient using any standard route of administration, including parenterally, such as intravenously, intraperitoneally, intrapulmonary, subcutaneously or intramuscularly, intrathecally, topically, transdermally, rectally, orally, nasally or by inhalation. Slow release formulations may also be prepared from the agents described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

Administration may take the form of single dose administration, or a compound as disclosed herein can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

In an embodiment, the pharmaceutical compositions are formulated with one or more pharmaceutically acceptable excipient, such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders. A pharmaceutical composition can also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

The pharmaceutical compositions described herein are formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). The suspensions may also contain one or more preservatives (e.g., acetic acid, methyl or n-propyl p-hydroxy-benzoate); one or more coloring agents; one or more flavoring agents; and one or more sweetening agents such as sucrose or saccharin.

The pharmaceutical compositions may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using those suitable dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compounds described herein may be formulated for oral administration in a lipid-based formulation suitable for low solubility compounds. Lipid-based formulations can generally enhance the oral bioavailability of such compounds.

As such, pharmaceutical compositions comprise a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In some embodiments, cyclodextrins may be added as aqueous solubility enhancers. Exemplary cyclodextrins include hydroxypropyl, hydroxyethyl, glucosyl, maltosyl and maltotriosyl derivatives of α-, β-, and γ-cyclodextrin. A specific cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the invention in the composition.

Methods of Treatment

Provided herein are methods of different types of cancer in a subject (e.g., a mammal) in need thereof comprising administering to the subject the compound or composition as described herein in an amount effective to treat said cancer. In some cases, the mammalian subject is a human subject. Practice of methods described herein in other mammalian subjects, especially mammals that are conventionally used as models for demonstrating therapeutic efficacy in humans (e.g., primate, porcine, canine, or rabbit animals), is also contemplated. Standard dose-response studies are used to optimize dose and dosing schedule.

The disclosed methods are useful for treating cancer, for example, inhibiting cancer growth, including complete cancer remission, for inhibiting cancer metastasis, and for promoting cancer resistance. The term "cancer growth" generally refers to any one of a number of indices that suggest change within the cancer to a more developed form. Thus, indices for measuring an inhibition of cancer growth include but are not limited to a decrease in cancer cell survival, a decrease in tumor volume or morphology (for example, as determined using computed tomographic (CT), sonography, or other imaging method), a delayed tumor growth, a destruction of tumor vasculature, improved performance in delayed hypersensitivity skin test, an increase in the activity of cytolytic T-lymphocytes, and a decrease in levels of tumor-specific antigens.

The term "cancer resistance" refers to an improved capacity of a subject to resist cancer growth, in particular growth of a cancer already had. In other words, the term "cancer resistance" refers to a decreased propensity for cancer growth in a subject.

In one aspect, the cancer comprises a solid tumor, for example, a carcinoma and a sarcoma. Carcinomas include malignant neoplasms derived from epithelial cells which infiltrate, for example, invade, surrounding tissues and give rise to metastases. Adenocarcinomas are carcinomas derived from glandular tissue, or from tissues that form recognizable glandular structures. Another broad category of cancers includes sarcomas and fibrosarcomas, which are tumors whose cells are embedded in a fibrillar or homogeneous substance, such as embryonic connective tissue. The invention also provides methods of treatment of cancers of myeloid or lymphoid systems, including leukemias, lymphomas, and other cancers that typically are not present as a tumor mass, but are distributed in the vascular or lymphoreticular systems. Further contemplated are methods for treatment of adult and pediatric oncology, growth of solid tumors/malignancies, myxoid and round cell carcinoma, locally advanced tumors, cancer metastases, including lymphatic metastases. The cancers listed herein are not intended to be limiting. Age (child and adult), sex (male and female), primary and secondary, pre- and post-metastatic, acute and chronic, benign and malignant, anatomical location cancer embodiments and variations are contemplated targets. Cancers are grouped by embryonic origin (e.g., carcinoma, lymphomas, and sarcomas), by organ or physiological system, and by miscellaneous grouping. Particular cancers may overlap in their classification, and their listing in one group does not exclude them from another.

Carcinomas that may targeted include adrenocortical, acinar, acinic cell, acinous, adenocystic, adenoid cystic, adenoid squamous cell, cancer adenomatosum, adenosquamous, adnexel, cancer of adrenal cortex, adrenocortical, aldosterone-producing, aldosterone-secreting, alveolar, alveolar cell, ameloblastic, ampullary, anaplastic cancer of thyroid gland, apocrine, basal cell, basal cell, alveolar, comedo basal cell, cystic basal cell, morphea-like basal cell, multicentric basal cell, nodulo-ulcerative basal cell, pigmented basal cell, sclerosing basal cell, superficial basal cell, basaloid, basosquamous cell, bile duct, extrahepatic bile duct, intrahepatic bile duct, bronchioalveolar, bronchiolar, bronchioloalveolar, bronchoalveolar, bronchoalveolar cell, bronchogenic, cerebriform, cholangiocelluarl, chorionic, choroids plexus, clear cell, cloacogenic anal, colloid, comedo, corpus, cancer of corpus uteri, cortisol-producing, cribriform, cylindrical, cylindrical cell, duct, ductal, ductal cancer of the prostate, ductal cancer in situ (DCIS), eccrine, embryonal, cancer en cuirasse, endometrial, cancer of endometrium, endometroid, epidermoid, cancer ex mixed tumor, cancer ex pleomorphic adenoma, exophytic, fibrolamellar, cancer fibro'sum, follicular cancer of thyroid gland, gastric, gelatinform, gelatinous, giant cell, giant cell cancer of thyroid gland, cancer gigantocellulare, glandular, granulose cell, hepatocellular, Hürthle cell, hypernephroid, infantile embryonal, islet cell carcinoma, inflammatory cancer of the breast, cancer in situ, intraductal, intraepidermal, intraepithelial, juvenile embryonal, Kulchitsky-cell, large cell, leptomeningeal, lobular, infiltrating lobular, invasive lobular, lobular cancer in situ (LCIS), lymphoepithelial, cancer medullare, medullary, medullary cancer of thyroid gland, medullary thyroid, melanotic, meningeal, Merkel cell, metatypical cell, micropapillary, mucinous, cancer muciparum, cancer mucocellulare, mucoepidermoid, cancer mucosum, mucous, nasopharyngeal, neuroendocrine cancer of the skin, noninfiltrating, non-small cell, non-small cell lung cancer (NSCLC), oat cell, cancer ossificans, osteoid, Paget's, papillary, papillary cancer of thyroid gland, periampullary, preinvasive, prickle cell, primary intrasseous, renal cell, scar, schistosomal bladder, Schneiderian, scirrhous, sebaceous, signet-ring cell, cancer simplex, small cell, small cell lung cancer (SCLC), spindle cell, cancer spongiosum, squamous, squamous cell, terminal duct, anaplastic thyroid, follicular thyroid, medullary thyroid, papillary thyroid, trabecular cancer of the skin, transitional cell, tubular, undifferentiated cancer of thyroid gland, uterine corpus, verrucous, villous, cancer villosum, yolk sac, squamous cell particularly of the head and neck, esophageal squamous cell, and oral cancers and carcinomas.

Sarcomas that may be targeted include adipose, alveolar soft part, ameloblastic, avian, botryoid, sarcoma botryoides, chicken, chloromatous, chondroblastic, clear cell sarcoma of kidney, embryonal, endometrial stromal, epithelioid, Ewing's, fascial, fibroblastic, fowl, giant cell, granulocytic, hemangioendothelial, Hodgkin's, idiopathic multiple pigmented hemorrhagic, immunoblastic sarcoma of B cells, immunoblastic sarcoma of T cells, Jensen's, Kaposi's, kupffer cell, leukocytic, lymphatic, melanotic, mixed cell, multiple, lymphangio, idiopathic hemorrhagic, multipotential primary sarcoma of bone, osteoblastic, osteogenic, parosteal, polymorphous, pseudo-kaposi, reticulum cell, reticulum cell sarcoma of the brain, rhabdomyosarcoma, rous, soft tissue, spindle cell, synovial, telangiectatic, sarcoma (osteosarcoma)/malignant fibrous histiocytoma of bone, and soft tissue sarcomas.

Lymphomas that may be targeted include AIDS-related, non-Hodgkin's, Hodgkin's, T-cell, T-cell leukemia/lymphoma, African, B-cell, B-cell monocytoid, bovine malignant, Burkitt's, centrocytic, lymphoma cutis, diffuse, diffuse, large cell, diffuse, mixed small and large cell, diffuse, small cleaved cell, follicular, follicular center cell, follicular, mixed small cleaved and large cell, follicular, predominantly large cell, follicular, predominantly small cleaved cell, giant follicle, giant follicular, granulomatous, histiocytic, large cell, immunoblastic, large cleaved cell, large nocleaved cell, Lennert's, lymphoblastic, lymphocytic, intermediate; lymphocytic, intermediately differentiated, plasmacytoid; poorly differentiated lymphocytic, small lymphocytic, well differentiated lymphocytic, lymphoma of cattle; MALT, mantle cell, mantle zone, marginal zone, Mediterranean lymphoma mixed lymphocytic-histiocytic, nodular, plasmacytoid, pleomorphic, primary central nervous system, primary effusion, small b-cell, small cleaved cell, small concleaved cell, T-cell lymphomas; convoluted T-cell, cutaneous t-cell, small lymphocytic T-cell, undefined lymphoma, u-cell, undifferentiated, aids-related, central nervous system, cutaneous T-cell, effusion (body cavity based), thymic lymphoma, and cutaneous T cell lymphomas.

Leukemias and other blood cell malignancies that may be targeted include acute lymphoblastic, acute myeloid, acute lymphocytic, acute myelogenous leukemia, chronic myelogenous, hairy cell, erythroleukemia, lymphoblastic, myeloid, lymphocytic, myelogenous, leukemia, hairy cell, T-cell, monocytic, myeloblastic, granulocytic, gross, hand mirror-cell, basophilic, hemoblastic, histiocytic, leukopenic, lymphatic, Schilling's, stem cell, myelomonocytic, monocytic, prolymphocytic, promyelocytic, micromyeloblastic, megakaryoblastic, megakaryoctyic, rieder cell, bovine, aleukemic, mast cell, myelocytic, plamsa cell, subleukemic, multiple myeloma, nonlymphocytic, chronic myelogenous leukemia, chronic lymphocytic leukemia, polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia and chronic myelocytic leukemias.

Brain and central nervous system (CNS) cancers and tumors that may be targeted include astrocytomas (including cerebellar and cerebral), brain stem glioma, brain tumors, malignant gliomas, ependymoma, glioblastoma, medulloblastoma, supratentorial primitive neuroectodermal tumors, visual pathway and hypothalamic gliomas, primary central nervous system lymphoma, ependymoma, brain stem glioma, visual pathway and hypothalamic glioma, extracranial germ cell tumor, medulloblastoma, myelodysplastic syndromes, oligodendroglioma, myelodysplastic/myeloproliferative diseases, myelogenous leukemia, myeloid leukemia, multiple myeloma, myeloproliferative disorders, neuroblastoma, plasma cell neoplasm/multiple myeloma, central nervous system lymphoma, intrinsic brain tumors, astrocytic brain tumors, gliomas, and metastatic tumor cell invasion in the central nervous system.

Gastrointestimal cancers that may be targeted include extrahepatic bile duct cancer, colon cancer, colon and rectum cancer, colorectal cancer, gallbladder cancer, gastric (stomach) cancer, gastrointestinal carcinoid tumor, gastrointestinal carcinoid tumors, gastrointestinal stromal tumors, bladder cancers, islet cell carcinoma (endocrine pancreas), pancreatic cancer, islet cell pancreatic cancer, prostate cancer rectal cancer, salivary gland cancer, small intestine cancer, colon cancer, and polyps associated with colorectal neoplasia.

Lung and respiratory cancers that may be targeted include bronchial adenomas/carcinoids, esophagus cancer esophageal cancer, esophageal cancer, hypopharyngeal cancer, laryngeal cancer, hypopharyngeal cancer, lung carcinoid tumor, non-small cell lung cancer, small cell lung cancer, small cell carcinoma of the lungs, mesothelioma, nasal cavity and paranasal sinus cancer, nasopharyngeal cancer, nasopharyngeal cancer, oral cancer, oral cavity and lip cancer, oropharyngeal cancer; paranasal sinus and nasal cavity cancer, and pleuropulmonary blastoma.

Urinary tract and reproductive cancers that may be targeted include cervical cancer, endometrial cancer, ovarian epithelial cancer, extragonadal germ cell tumor, extracranial germ cell tumor, extragonadal germ cell tumor, ovarian germ cell tumor, gestational trophoblastic tumor, spleen, kidney cancer, ovarian cancer, ovarian epithelial cancer, ovarian germ cell tumor, ovarian low malignant potential tumor, penile cancer, renal cell cancer (including carcinomas), renal cell cancer, renal pelvis and ureter (transitional cell cancer), transitional cell cancer of the renal pelvis and ureter, gestational trophoblastic tumor, testicular cancer, ureter and renal pelvis, transitional cell cancer, urethral cancer, endometrial uterine cancer, uterine sarcoma, vaginal cancer, vulvar cancer, ovarian carcinoma, primary peritoneal epithelial neoplasms, cervical carcinoma, uterine cancer and solid tumors in the ovarian follicle), superficial bladder tumors, invasive transitional cell carcinoma of the bladder, and muscle-invasive bladder cancer.

Skin cancers and melanomas (as well as non-melanomas) that may be targeted include cutaneous t-cell lymphoma, intraocular melanoma, tumor progression of human skin keratinocytes, basal cell carcinoma, and squamous cell cancer. Liver cancers that may be targeted include extrahepatic bile duct cancer, and hepatocellular cancers. Eye cancers that may be targeted include intraocular melanoma, retinoblastoma, and intraocular melanoma Hormonal cancers that may be targeted include: parathyroid cancer, pineal and supratentorial primitive neuroectodermal tumors, pituitary tumor, thymoma and thymic carcinoma, thymoma, thymus cancer, thyroid cancer, cancer of the adrenal cortex, and ACTH-producing tumors.

Miscellaneous other cancers that may be targeted include advanced cancers, AIDS-related, anal cancer adrenal cortical, aplastic anemia, aniline, betel, buyo cheek, cerebriform, chimney-sweeps, clay pipe, colloid, contact, cystic, dendritic, cancer à deux, duct, dye workers, encephaloid, cancer en cuirasse, endometrial, endothelial, epithelial, glandular, cancer in situ, kang, kangri, latent, medullary, melanotic, mule-spinners', non-small cell lung, occult cancer, paraffin, pitch workers', scar, schistosomal bladder, scirrhous, lymph node, small cell lung, soft, soot, spindle cell, swamp, tar, and tubular cancers.

Miscellaneous other cancers that may be targeted also include carcinoid (gastrointestinal and bronchal) Castleman's disease chronic myeloproliferative disorders, clear cell sarcoma of tendon sheaths, Ewing's family of tumors, head and neck cancer, lip and oral cavity cancer, Waldenström's macroglobulinemia, metastatic squamous neck cancer with occult primary, multiple endocrine neoplasia syndrome, multiple myeloma/plasma cell neoplasm, Wilms' tumor, mycosis fungoides, pheochromocytoma, sezary syndrome, supratentorial primitive neuroectodermal tumors, unknown primary site, peritoneal effusion, malignant pleural effusion, trophoblastic neo-plasms, and hemangiopericytoma.

Further described herein are methods of stimulating an immune response in a mammalian subject comprising administering to the subject a compound or composition described herein. In some embodiments, the compound or composition is administered directly to the subject in the same manner as a vaccine. In some embodiments, the compounds described herein are useful for the induction of an immune response to a tumor antigen, one or more pathogenic organisms, or other antigen as described herein.

Dosing

The terms "therapeutically effective amount" and "prophylactically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, reduction in symptoms, or by any of the assays or clinical diagnostic tests described herein. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

Dosages of the therapeutic can be administered as a dose measured in mg. Contemplated dosages of the disclosed therapeutics include about 0.1 mg to 5000 mg (5 g). Specific ranges of doses in mg include about 1 mg to about 4000 mg, about 2 mg to about 3000 mg, about 5 mg to about 2000 mg, about 5 mg to about 1000 mg, about 10 mg to about 1000 mg, about 20 mg to about 500 mg, about 30 mg to about 200 mg, and about 50 mg to about 100 mg. The doses can be total daily amounts given to a subject or the dose given at any single time. Thus, the dose can be administered as a single dose or in divided doses throughout the day (e.g., in two, three, four, or five doses over the course of a day).

Dosages of the therapeutic can alternately be administered as a dose measured in mg/kg (mg compound per kilogram of body weight for the treated subject). Contemplated mg/kg doses of the disclosed therapeutics include about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg.

Combination Therapy

The methods disclosed herein can also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used. In some cases, a compound disclosed herein is administered and/or formulated with a second therapeutic.

The second therapeutic can be one or more of a chemotherapeutic or an immunotherapeutic agent. In some specific cases, the second therapeutic is a cytokine, an anti-inflammatory agent, a cancer vaccine, a cancer antigen, or a polynuecleotide encoding a cancer antigen. In some cases, the second therapeutic is radiation.

Contemplated chemotherapeutics for use in combination therapies as disclosed herein include aspirin, sulindac, curcumin, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; and enzymes such as L-asparaginase.

Contemplated biological response modifying agents for use in combination therapies as disclosed herein include, but are not limited to, interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; non-steroidal antiandrogens such as flutamide; kinase inhibitors, histone deacetylase inhibitors, methylation inhibitors, proteasome inhibitors, monoclonal antibodies, oxidants, anti-oxidants, telomerase inhibitors, BH3 mimetics, ubiquitin ligase inhibitors, stat inhibitors and receptor tyrosin kinase inhibitors such as imatinib mesylate (marketed as Gleevac or Glivac) and erlotinib (an EGF receptor inhibitor) now marketed as Tarveca; and anti-virals such as oseltamivir phosphate, Amphotericin B, and palivizumab.

Contemplated immunotherapeutic agents for use in the combination therapies disclosed herein include, but are not limited to a Her2/neu receptor antibody such as trastuzumab (marketed as Herceptin®), an anti-CD52 antibody such as alemtuzumab (marketed as Campath®. MabCampath® or Campath-1H), an anti-CD33 antibody such as gemtuzumab linked to calicheamicin (marketed as Mylotarg®), an anti-CD20 antibody such as rituximab (marketed as Rituxan® and MabThera®), Ibritumomab tiuxetan (marketed as Zevalin®), anti-TNFα antibodies such as infliximab (marketed as Remicade®) or adalimmumab (marketed as Humira®), a soluble TNFR2 molscule such as etanercept (marketed as Enbrel®), an antibody to the CD25 chain of the IL-2 receptor such as basiliximab (marketed as Simulect®), an anti CD40/CD40L antibody such as humanized IgG1 anti-human CD40 antibody (SGN-40), an anti-CTLA-4 blocking antibody such as iplimumab (marketed as MDX-101 or MDX-010) or tremelimumab, an anti-programmed death protein 1 (PD-1) antibody (i.e., an anti-CD279 antibody), an anti-programmed cell death ligand (PDL-1) antibody, an anti-glucocorticoid-induced TNFR-related gene (GITR) antibody, an anti-OX-40 (CD134) antibody, soluble lymphocyte-activation gene 3 (also known as LAG3 or CD223)-based immune modulator such as LAG3-Ig (IMP321), Toll-like receptor agonists such as monophosphoril lipid A (MPL®), CpG, single-stranded RNA, nucleotides, nucleotide analogue, CL087 (a TLR7-specific ligand), loxoribine, polyinosine-polycytidylic acid, flagellin, resiquimod, immiquimod, gardiquimod, NOD ligands such as muramyl dipeptide, murabutide, peptidoglycan and muramyldipeptide, In some embodiments, a combination therapy as disclosed herein comprises administration of a compound disclosed herein, such as a compound having a structure:

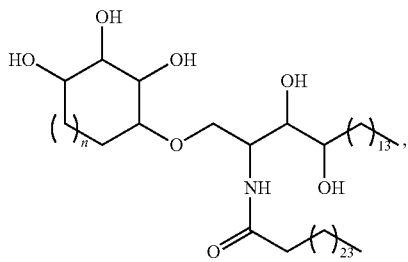

wherein n is 1, 2, or 3, or a salt, ester, solvate, or hydrate thereof and one or more antibodies selected from the group consisting of an anti-PD1 antibody, an anti-PDL-1 antibody, an anti-CTLA-4 antibody an anti-GITR antibody and an anti-OX40 antibody.

In some embodiments, the anti-PD1 antibody is a monoclonal antibody directed against the negative immynoregulatory human cell surface receptor PD-1 with immunopotentiation activity. An exemplary anti-PD1 antibody is human monoclonal antibody MDX-1106 which binds and blocks the activation of PD-1 by its ligands PD-L1 and PD-L2, resulting in the activation of T-cells and cell-mediated immune responses against tumor cells. In some embodiments, the anti-PD-L1 antibody is a monoclonal antibody directed against the protein ligand PD-L1 with immunomodulating and antineoplastic activities. An exemplary anti-PD-L1 antibody is human monoclonal antibody MDX-1105 which binds PD-L1 and blocks its binding to and activation of its receptor PD-1, which may enhance the T-cell-mediated immune response to neoplasms and reverse T-cell inactivation in chronic infections disease. PD-L1 is expressed broadly on hematopoietic and parenchymal tissues.

In some embodiments, the anti-CTLA-4 antibody is a monoclonal antibody directed against the T-cell receptor protein cytotoxic T-lymphocyte-associated protein 4 (CTLA-4). An exemplary anti-CTLA-4 antibody is human IgG2 monoclonal antibody tremelimumab which binds to CTLA4 and blocks binding of the antigen presenting cell ligands B7-1 and B7-2 to CTLA-4, resulting in inhibition of B7-CTLA4-mediated downregulation of T-cell activation. Another exemplary anti-CTLA-4 antibody is human IgG1 monoclonal antibody ipilimumab which binds to CTLA4 and blocks binding of the antigen presenting cell ligands B7-1 and B7-2 to CTLA-4, resulting in inhibition of B7-CTLA4-mediated downregulation of T-cell activation. Ipilimumab is undergoing clinical trials for the treatment of non-small cell lung carcinoma, small cell lung cancer and metastatic hormone-refractory prostate cancer.

In some embodiments, the anti-GITR antibody is a monoclonal antibody directed against glucocorticoid-induced tumor necrosis factor receptor (GITR) which blocks the interaction of GITR with its ligand, enhances cytotoxicity of natural human killer cells and/or downmodulates GITR expression on peripheral blood lymphocytes.

In some embodiments, the an anti-OX40 antibody is an agonistic monoclonal antibody that mimicks the natural OX40 ligand and selectively binds to and activates the OX40 receptor. Receptor activation induces proliferation of memory and effector T cells Cytokines that are effective in inhibiting tumor growth/metastasis are contemplated for use in the combination therapy. Such cytokines, lymphokines, or other hematopoietic factors include, but are not limited to, M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNFα, TNF1, TNF2, G-CSF, Meg-CSF, GM-CSF, thrombopoietin, stem cell factor, and erythropoietin.

An immunotherapeutic agent can be a cancer vaccine. A cancer vaccine is an agent, molecule, or immunogen which stimulates or elicits an endogenous immune response in an individual or subject against one or more tumor antigens.

As used herein, a cancer antigen is broadly defined as an antigen specifically expressed by a tumour or cancer cell. A cancer antigen which is present on the surface of cancer cells in an individual but which is not present on the surface of normal somatic cells of the individual i.e. the antigen is exposed to the immune system in cancer cells but not in normal somatic cells. The antigen may be expressed at the cell surface of the tumour cell where it is recognized by components of the humoral immune system such as B lymphocytes (B cells). Intracellular tumour antigens are processed into shorter peptide fragments which form complexes with major histocompatibility complex (MHC) molecules and are presented on the cell surface of cancer cells, where they are recognized by the T cell receptors (TCR's) of T lymphocytes (T cells). Preferably, the cancer antigen is one which is not expressed by normal cells, or at least not expressed to the same level as in tumour cells. An immunotherapeutic agent, such as a cancer vaccine maybe comprised of one or more epitopes or antigenic determinants, e.g. peptide epitopes or antigenic determinants from a tumor or cancer antigen, such that the immune response generated by the cancer vaccine is reactive against the antigen.

A cancer vaccine may enhance the presentation of one or more cancer antigens to both antigen presenting cells (e.g., macrophages and dendritic cells) and/or to other immune cells such as T cells, B cells, and NK cells. In some examples, preparations and/or formulations of cancer vaccines may be used together with one or more adjuvants that are well known in the art, to induce an immune response or to increase an immune response.

Cancer antigens may include, for example, cancer-testis antigens encoded by cancer-germ line genes. Cancer-testis (CT) antigens constitute a unique group of genes which are predominantly expressed in human germ line cells such as placenta and testis but become reactivated in various malignancies (Simpson et al., Nature Rev (2005) 5, 615-625). Most of these genes are located as multigene families on the X-chromosome and are also referred to as CT-X antigens (Simpson et al., Nature Rev (2005) 5, 615-625). Analogies have been drawn between their expression pattern during germ maturation and neoplastic transformation, thus suggesting their involvement in several steps of tumorigenesis (Simpson et al., Nature Rev (2005) 5, 615-625). The CT-X antigens are broadly expressed in a wide variety of cancer types including for example bladder cancer, lung cancer, ovarian cancer, breast cancer, prostate cancer, Brain cancer, glioma, glioblastoma, hepatocellular carcinoma and melanoma. Moreover, their expression pattern is closely associated with advanced disease and poor outcome and might thus be of diagnostic and/or prognostic relevance (Gure et al., Clin Cancer Res (2005) 11,8055-8062; Velazquez et al., Cancer Immun (2007) 7, 1 1; Andrade et al., Cancer Immun (2008) 8, 2; Tinguely et al., Cancer Science (2008); Napoletano et al., Am J of Obstet Gyn (2008) 198, 99 e91-97. Due to their highly restricted expression in malignant tissues, their tumour associated peptide epitopes provide promising targets for anticancer immunotherapy (Scanlan et al., Immunol Rev (2002) 188, 22-32). Indeed, clinical trials evaluating the role of CT antigens, namely MAGE-A3, Prame and NY-ESO-I, as targets for specific immunotherapy have already been initiated in a number of different malignancies (Bender et al., Cancer Immunol (2007) 7, 16; Atanackovic et al., PNAS (2008) 105, 1650-1655; Jager et al., PNAS (2006) 103, 14453-14458; van Baren et al., J Clin Oncol (2005) 23, 9008-9021; Valmori et al., PNAS (2007) 104, 8947-8952; Odunsi et al., PNAS (2007) 104, 12837-12842; Davis et al., PNAS (2004) 101, 10697-10702 (9-15). Tumor antigens which may be comprised of the full-length polypeptide sequence of the tumor antigen or an immunogenic fragment, or epitope derived from the full-length polypeptide sequence of the tumor antigen. Tumor antigens include the corresponding nucleotide sequence encoding for the full-length polypeptide, immunogenic fragment, or epitope derived from the full-length polypeptide sequence of the tumor antigen.

A fragment of a cancer antigen is a contiguous stretch of amino acid residues from the sequence of the antigen which is shorter than the full length antigen (i.e. it consists of fewer amino acid residues). For example, a fragment may comprise less than 500, less than 400, less than 300, less than 200, less than 100 amino acids, or less than 50 amino acids. A fragment will generally consist of at least 5 amino acids, for example, at least 10 amino acids, at least 15 amino acids, at least 20 amino acids, at least 25 amino acids, at least 30 amino acids or at least 35 amino acids. Fragments of cancer antigens may include immunogenic regions or epitopes that bind to MHC class I or class II molecules and are recognized by TCR's of T lymphocytes. Many such epitopes of cancer antigens are known in the art www.cancerimmunity.org/peptidedatabase/Tcellepitopes.

The cancer antigen can be a tumor associated peptide, or protein that induces or enhances immune response and is derived from tumor associated genes and encoded proteins including, for example, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (AGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1, CT-7, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RAR.alpha. fusion protein, PTPRK, K-ras, N-ras, Triosephosphate isomeras, GnTV, Herv-K-mel, Lage-1, Mage-C2, NA-88, /Lage-2, SP17, and TRP2-Int2, (MART-I), gp100 (Pmel 17), TRP-1, TRP-2, MAGE-1, MAGE-3, p15(58), CEA, NY-ESO (LAGE), SCP-1, Hom/Mel-40, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, .beta.-Catenin, CDK4, Mum-1, p16, TAGE, PSMA, PSCA, CT7, telomerase, 43-9F, 5T4, 791Tgp72, .alpha.-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NB\170K, NY-CO-1, RCAS1, SDCCAG16, TA-90 (Mac-2 binding protein\cyclophilin C-associated protein), TAAL6, TAG72, TLP, and TPS. For example, antigenic peptides characteristic of tumors include those listed in International Patent Application Publication No. WO 20000/020581 and U.S. Patent Application Publication No. 2010/0284965, which are each incorporated herein by reference. In some exemplary embodiments, the antigen is a tumor antigen selected from the group consisting of MUC1, MAGE, BAGE, GE, CAGE, SSX-2, NY-ESO-1, PRAME, PSMA, tyrosinase, melan-A, and mixtures thereof. In some variations, the cancer antigen is a mammalian protein. In some variations, the cancer antigen is a human protein. In some variations, the full-length protein is employed as the antigen. In some variations, peptides comprising an antigenic fragment of these proteins is used as the tumor antigen.

Other suitable antigens include cancer antigens in the following classes: cancer testis antigens (e.g., HOM-MEL-40), differentiation antigens (e.g., HOM-MEL-55), overexpressed gene products (HOM-MD-21), mutated gene products (NY-COL-2), splice variants (HOM-MD-397), gene amplification products (HOM-NSCLC-11) and cancer related autoantigens (HOM-MEL-2.4) as reviewed in Cancer Vaccines and Immunotherapy (2000) Eds Stern, Beverley and Carroll, Cambridge University Press, Cambridge. Further examples include, MART-1 (Melanoma Antigen Recognized by T-cells-1) MAGE-A (MAGE-A1, MAGE-A2, MAGE-A3, MAGE-A4, MAGE-A6, MAGE-A8, MAGE-A10, MAGE-A12), MAGE B (MAGE-B1-MAGE-B24), MAGE-C (MAGE-C1/CT7, CT10), GAGE (GAGE-1, GAGE-8, PAGE-1, PAGE-4, XAGE-1, XAGE-3), LAGE (LAGE-1a(1S), -1b(1L), NY-ESO-1), SSX (SSX1-SSX-5), BAGE, SCP-1, PRAME (MAPE), SART-1, SART-3, CTp11, TSP50, CT9/BRDT, gp100, MART-1, TRP-1, TRP-2, MELAN-A/MART-1, Carcinoembryonic antigen (CEA), prostate-specific antigen (PSA), MUCIN (MUC-1) and Tyrosinase. TAAs are reviewed in Cancer Immunology (2001) Kluwer Academic Publishers, The Netherlands. Additional cancer associated antigens include Her 2, survivin and TERT.

The term "antigen" refers to protein or peptide to be introduced into a subject. As described herein, an antigen may be provided through delivering a peptide or protein or through delivering a nucleic acid encoding a peptide or protein.

By "antigen" in the context of the present disclosure it is also meant to incorporate an antigenic peptide derived from an antigen. In particular, "cancer associated antigen" is intended to encompass a peptide derived from a cancer associated antigen.

An antigen such as a cancer associated antigen can be provided for use as a medicament in a number of different ways. It can be administered as part of a vector.

Any suitable vector may be used to introduce a polynucleotide that encodes a polypeptide of the invention encoding one of the tumor antigen proteins into the host. Exemplary vectors that have been described in the literature include replication deficient retroviral vectors, including but not limited to lentivirus vectors [Kim et al., J. Virol., 72(1): 811-816 (1998); Kingsman & Johnson, Scrip Magazine, October, 1998, pp. 43 46.]; adeno-associated viral (AAV) vectors [U.S. Pat. Nos. 5,474,935; 5,139,941; 5,622,856; 5,658,776; 5,773,289; 5,789,390; 5,834,441; 5,863,541; 5,851,521; 5,252,479; Gnatenko et al., J. Invest. Med., 45: 87 98 (1997)]; adenoviral (AV) vectors [See, e.g., U.S. Pat. Nos. 5,792,453; 5,824,544; 5,707,618; 5,693,509; 5,670,488; 5,585,362; Quantin et al., Proc. Natl. Acad. Sci. USA, 89: 2581 2584 (1992); Stratford Perricadet et al., J. Clin. Invest., 90: 626 630 (1992); and Rosenfeld et al., Cell, 68: 143 155 (1992)]; an adenoviral adenoassociated viral chimeric (see for example, U.S. Pat. No. 5,856,152) or a vaccinia viral or a herpesviral (see for example, U.S. Pat. Nos. 5,879,934; 5,849,571; 5,830,727; 5,661,033; 5,328,688; Lipofectin mediated gene transfer (BRL); liposomal vectors [See, e.g., U.S. Pat. No. 5,631,237 (Liposomes comprising Sendai virus proteins)]; and combinations thereof.

Suitable cancer vaccines are known in the art and may be produced by any convenient technique.

For example, a cancer vaccine may be generated wholly or partly by chemical synthesis. For example, a peptide-based vaccine or immunogen may be synthesised using liquid or solid-phase synthesis methods; in solution; or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof. Chemical synthesis of peptides is well-known in the art (J. M. Stewart and J. D. Young, Solid Phase Peptide Synthesis, 2nd edition, Pierce Chemical Company, Rockford, Ill. (1984); M. Bodanzsky and A. Bodanzsky, The Practice of Peptide Synthesis, Springer Verlag, New York (1984); J. H. Jones, The Chemical Synthesis of Peptides. Oxford University Press, Oxford 1991; in Applied Biosystems 430A Users Manual, ABI Inc., Foster City, Calif.; G. A. Grant, (Ed.) Synthetic Peptides, A User's Guide. W. H. Freeman & Co., New York 1992, E. Atherton and R. C. Sheppard, Solid Phase Peptide Synthesis, A Practical Approach. IRL Press 1989 and in G. B. Fields, (Ed.) Solid-Phase Peptide Synthesis (Methods in Enzymology Vol. 289). Academic Press, New York and London 1997).

Alternatively, peptide-based cancer vaccines may be generated wholly or partly by recombinant techniques. For example, a nucleic acid encoding a cancer antigen may be expressed in a host cell and the expressed antigen isolated and/or purified from the cell culture. For example, antigen may be expressed in *E. coli* either in soluble form or in inclusion bodies, which may be solubilized and refolded. After expression, the antigen may be isolated and/or purified. Cancer antigen may be analyzed by standard techniques, such as mass spectrometry and western blot analysis.

The use of tumor antigens to generate immune responses is well-established in the art (see for example; Kakimi K, et al. Int J Cancer. 2011 Feb. 3; Kawada J, Int J Cancer. 2011 Mar. 16; Gnjatic S, et al. Clin Cancer Res. 2009 Mar. 15; 15(6):2130-9; Yuan J, et al. Proc Natl Acad Sci USA. 2008 Dec. 23; 105(51):20410-5; Sharma P, et al. J Immunother. 2008 November-December; 31(9):849-57; Wada H, et al. Int J Cancer. 2008 Nov. 15; 123(10):2362-9; Diefenbach C S, et al. Clin Cancer Res. 2008 May 1; 14(9):2740-8; Bender A, et al. Cancer Immun. 2007 Oct. 19; 7:16; Odunsi K, et al. Proc Natl Acad Sci USA. 2007 Jul. 31; 104(31):12837-42; Valmori D, et al. Proc Natl Acad Sci USA. 2007 May 22; 104(21):8947-52; Uenaka A, et al. Cancer Immun. 2007 Apr. 19; 7:9; Kawabata R, et al. Int J Cancer. 2007 May 15; 120(10):2178-84; Jäger E, et al. Proc Natl Acad Sci USA. 2006 Sep. 26; 103(39):14453-8; Davis I D Proc Natl Acad Sci USA. 2005 Jul. 5; 102(27):9734; Chen Q, Proc Natl Acad Sci USA. 2004 Jun. 22; 101(25):9363-8; Jäger E, Proc Natl Acad Sci USA. 2000 Oct. 24; 97(22):12198-203; Carrasco J, et al. J Immunol. 2008 Mar. 1; 180(5):3585-93; van Baren N, et al. J Clin Oncol. 2005 Dec. 10; 23(35): 9008-21; Kruit W H, et al. Int J Cancer. 2005 Nov. 20; 117(4):596-604; Marchand M, et al. Eur J Cancer. 2003 January; 39(1):70-7; Marchand M et al. Int J Cancer. 1999 Jan. 18; 80(2):219-30; Atanackovic D, et al. Proc Natl Acad Sci USA. 2008 Feb. 5; 105(5):1650-5).

Typically, an immunotherapeutic agent, such as a cancer vaccine, is administered to the individual whose cancer expresses the said antigen. Cancer cells from the individual may be analyzed to identify the cancer antigen and patients are then identified for administration of the appropriate immunotherapeutic agent or cancer vaccine. For example, a method as described herein may comprise the step of identifying a cancer antigen which is displayed by one or more cancer cells in a sample obtained from the individual.

A biological sample may be obtained from the subject such as a biopsy, blood or bone marrow sample and tested for the presents of cancer cells which may be identified as displaying the cancer antigen using any standard techniques including but not limited to immunological techniques, such as immunocytochemistry and immunohistochemistry may be employed. Additional techniques include immunological analysis such as serologically determining an autologous immune response to said cancer antigen, see WO2001/007917. Analysis of gene expression can be performed using methods known in the art such as polymerase chain reaction or microarray analysis.

Combination Therapy Compositions:

A pharmaceutical composition may comprise, in addition to (1) the compound as disclosed herein, (2) an immunotherapeutic agent such as a cancer vaccine, (3) an adjuvant, and (4) a pharmaceutically acceptable excipient, carrier, buffer, stabilizer or other materials well known to those skilled in the art. Suitable materials will be sterile and pyrogen free, with a suitable isotonicity and stability. Examples of pharmaceutically acceptable excipient, carrier, buffer, stabilizer or other materials include sterile saline (e.g. 0.9% NaCl), water, dextrose, glycerol, ethanol or the like or combinations thereof. Such materials should be non-toxic and should not interfere with the efficacy of the active compound. The precise nature of the carrier or other material will depend on the route of administration, which may be by bolus, infusion, injection or any other suitable route, as discussed below. The composition may further contain auxiliary substances such as wetting agents, emulsifying agents, pH buffering agents or the like.

An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of Salmonella Minnesota Re 595 lipopolysaccharide; saponins including QS21 (SmithKlineBeecham), a pure QA-21 saponin purified from Quillja saponaria extract; DQS21, described in PCT application WO96/33739 (SmithKline Beecham); QS-7, QS-17, QS-18, and QS-L1 (So et al., MoI Cells (1997) 7:178-186); ISCOMATRIX adjuvant, a cage-like structure composed of saponin, phospholipid, and cholesterol (see, e.g., Maraskovsky et al., Clin. Cancer Res. (2004) 10:2879-2890); incomplete Freund's adjuvant; complete Freund's adjuvant; montanide; alum; CpG oligonucleotides (see e.g. Kreig et al., Nature 374:546-9, 1995) and other immunostimulatory oligonucleotides including poly-IC and poly-ICLC (Hiltonol®); and various water-in-oil emulsions prepared from biodegradable oils such as squalene and/or tocopherol.

The cancer vaccine may be administered in conjunction with an adjuvant. Suitable adjuvants are well known in the art and include aluminum salts, such as alum (aluminium potassium sulphate dodecahydrate), aluminum hydroxide and aluminum phosphate and organic compounds, such as squalene.

In addition to a cancer antigen, an immunotherapeutic, immunogenic or vaccine formulation may comprise an adjuvant. For example, a formulation may comprise 1-500 µg, preferably 1-50 µg, of cancer antigen and 0.5 to 20 mg, preferably 1-10 mg, of adjuvant in a pharmaceutically acceptable carrier or diluent as mentioned above.

A vaccine formulation may comprise a Toll-like Receptor (TLR) ligand. Suitable TLR ligands include polyinosinicpolycytidylic acid (poly I:C), lipopolysaccharide (LPS), CpG oligodeoxynucleotide, poly LC, poly ICLC, MPL (Corixa Corp) and imidazoquinolines, such as imiquimod and R848. The use of TLR ligands to modulate immune responses is well-known in the art (see for example, Weiner et al (1997) PNAS USA 94 10833-10837; Vabulas et al J. Immunol. (2000) 164 2372-2378; Gunzer et al (2005) Blood 106 2424-2432).

Formulations of immunotherapeutic agents, such as cancer vaccines, are well-known in the art and include MAGE-A3 ASCI, NY-ESO-1 ASCI and PRAME ASCI (GSK Bio); Provenge (Dendreon), Abogovomab (Meranini), M-Vax (Avax), Allovectin-7 (Vial) for metastatic melanoma, GSK1572932A (GSK Bio) Belagenpumatucel-L (Novarex) BMP-25 (Merck Serono), BiovaxID (Biovest/Accentia), MDX-1379 (Medarex/BMS), Ipilimumab (BMS) Trovax (Oxford Biomedical) Oncophage (Antigenics) and PR1 leukemia peptide (The Vaccine company).

The invention will be more fully understood by reference to the following examples which detail exemplary embodiments of the invention. They should not, however, be construed as limiting the scope of the invention. All citations throughout the disclosure are hereby expressly incorporated by reference.

EXAMPLES

Synthesis of Compounds

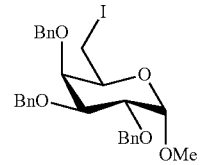

6-iodo-((2R,3S,4R)-benzyloxy)-methyl-α-D-galactose (46)

A solution of glycoside 45/49/52 (206 mg, 0.44 mmol) and PPh$_3$ (139 mg, 0.53 mmol) in toluene (5 mL) was heater under reflux with for 10 min. The reaction mixture was cooled to 80° C., and then imidazole (89 mg, 1.32 mmol) and I$_2$ (142 mg, 0.57 mmol) were added. The mixture was heated under reflux for 20 min before being concentrated under reduced pressure. The residue was dissolved in EtOAc (50 mL) and washed with Na$_2$S$_2$O$_3$ solution (20 mL) and H$_2$O (20 mL). The organic layer was then dried over Na$_2$SO$_4$, filtered and the filtrate concentrated under reduced pressure. The crude product was purified by column chromatography (8% EtOAc in hexanes) to give iodide 46 as a colourless oil (183 mg, 72%).

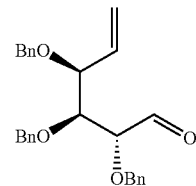

(2R,3S,4S)-2,3,4-tris(benzyloxy)hex-5-enal (47)

Zinc dust was preactivated by stirring in HCl (50 mL of 1.0 M solution) at rt for 15 mins, before being filtered and washed sequentially with H$_2$O (30 mL), acetone (30 mL) and Et$_2$O (30 mL). The zinc was then dried under high vacuum with a heatgun. The activated zinc (0.706 mg, 10.8 mmol) was added to a solution of glycoside 46 (620 mg, 1.08 mmol) and TMSCl (0.137 mL, 1.08 mmol) in THF (20 mL) and the reaction mixture sonicated at 40° C. After 5 h Et$_2$O (50 mL) and H$_2$O (50 mL) were added to the suspension, which was then filtered through Celite. The layers were separated and the aqueous layer was extracted with Et$_2$O (3×25 mL). The combined organic layers were washed with H$_2$O (2×15 mL) and brine (15 mL), then dried over Na$_2$SO$_4$, filtered and the filtrate concentrated under reduced pressure. The crude product was purified by column chromatography (8% EtOAc in hexanes) to give aldehyde 47 as a colourless oil.

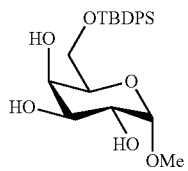

6-((tert-butyldiphenylsilyl)oxy)-methyl-α-D-galactose (50)

Imidazole (0.77 g, 11.30 mmol), and TBDPSCl (1.74 mL, 6.70 mmol) were added sequentially to a solution of methyl □-D-galactopyranoside (1.00 g, 5.15 mmol) in DMF (5 mL). After 24 h the reaction mixture was diluted with Et$_2$O (30 mL), washed with H$_2$O (20 mL) and NH$_4$Cl solution (20 mL). The organic layer was dried over Na$_2$SO$_4$, filtered and the filtrate concentrated under reduced pressure. The crude product was purified by column chromatography (30% hexanes in EtOAc) to give silyl ether 50 as a colourless oil (2.10 g, 94%).

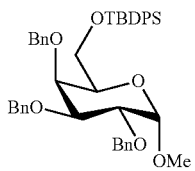

2,3,4-benzyloxy-6-((tert-butyldiphenylsily)oxy)-methyl-α-D-galactose (51)

NaH (60% wt in mineral oil, 0.61 g, 15.5 mmol) was added to a solution of glycoside 50 (1.20 g, 2.78 mmol) in DMF (10 mL) at 0° C. The reaction mixture was stirred for 20 min, then BnBr (1.33 mL, 11.1 mmol) was added at 0° C. After stirring overnight at rt the reaction was quenched with the slow addition of MeOH, and then diluted with EtOAc (30 mL). The organic layer was washed with H$_2$O (20 mL), dried over Na$_2$SO$_4$, filtered and the filtrate concentrated under reduced pressure. The crude product was purified by column chromatography (10% EtOAc in hexanes) to give tribenzyl ether 51 as a colourless oil.

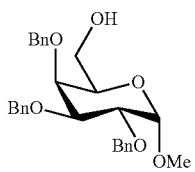

2,3,4-tribenzyloxy-methyl-α-D-galactose (52)

TBAF (1M solution in THF, 1.27 mL, 1.27 mmol) was added to a solution of glycoside 51 (460 mg, 0.63 mmol) in THF (5 mL). The reaction mixture was stirred overnight before being quenched with H$_2$O (15 mL). The resulting layers were separated and the aqueous layer was extracted with EtOAc (3×15 mL). The organic layers were combined and washed with brine (15 mL), dried over Na$_2$SO$_4$, filtered and the filtrate concentrated under reduced pressure to provide the crude product, which was used directly in the next reaction without further purification. Rf=0.19 (40% EtOAc in hexanes)

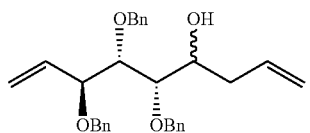 [SMILES: C=CCC(O)[C@H](OCc1ccccc1)[C@@H](OCc1ccccc1)[C@H](C=C)OCc1ccccc1]

(5S,6S,7S)-5,6,7-tris(benzyloxy)nona-1,8-dien-4-ol (53)

Allyl magnesium bromide (1.0 M in Et$_2$O, 1.44 mL, 1.44 mmol) was added dropwise over 5 min to a solution of aldehyde 47 (200 mg, 0.48 mmol) in THF (10 mL) at −78° C. The reaction mixture was left stirring at this temperature for 4 h before being quenched with NH$_4$Cl solution (30 mL). The resulting layers were separated and the aqueous layer was extracted with EtOAc (3×25 mL). The combined organic layers were washed with H$_2$O (20 mL) and brine (20 mL), dried over Na$_2$SO$_4$, filtered and the filtrate concentrated under reduced pressure. The crude product was purified by column chromatography (0-4% EtOAc in hexanes, gradient) to give product 53 as a mixture of two diastereoisomers.

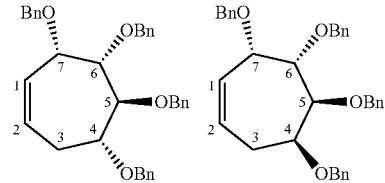 [SMILES: C1=C[C@H](OCc2ccccc2)[C@H](OCc2ccccc2)[C@@H](OCc2ccccc2)[C@H](OCc2ccccc2)C1 ; C1=C[C@H](OCc2ccccc2)[C@H](OCc2ccccc2)[C@@H](OCc2ccccc2)[C@@H](OCc2ccccc2)C1]

(4R,5S,6S,7S)-5,6,7-tris(benzyloxy)cyclohept-2-enol (54a) and (4S,5S,6S,7S)-5,6,7-tris(benzyloxy)cyclohept-2-enol (54b)

A solution of diene 53 (270 mg, 0.59 mmol) in CH$_2$Cl$_2$ (60 mL) was degassed according to the general procedure. Grubbs 2$^{nd}$ generation Ru metathesis catalyst (8 mg, 0.009 mmol) was added and the solution was heated under reflux. After 2 h the solution was concentrated under reduced pressure and the crude product purified by column chromatography (20% EtOAc in hexanes) to give products 54a and 54b.

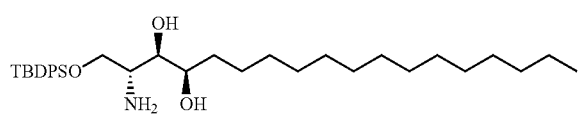

(2R,3R,4R)-2-amino-1-((tert-butyldiphenylsilyl)oxy) octadecane-3,4-diol (64)

TBDPSCl (2.46 mL, 9.45 mmol) was added to a solution of phytosphingsine (2.0 g, 6.3 mmol) in pyridine. After stirring overnight the reaction was quenched with MeOH (5 mL), then the solvent was removed under reduced pressure. The crude product was purified by column chromatography (50% EtOAc in hexanes, EtOAc, 0%-7% MeOH in EtOAc) to provide sphingosine 64 as a colourless oil.

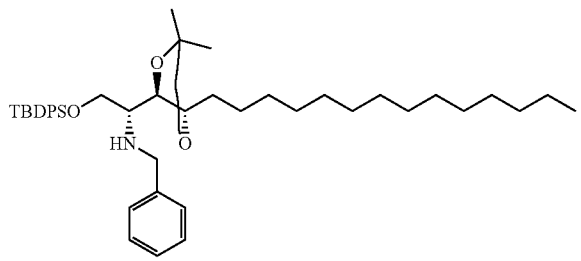

2R—N-benzyl-1-((tert-butyldiphenylsilyl)oxy)-(3R, 4R—O-isopropylidene) octadecane (65)

Benzaldehyde (86 µL, 0.85 mmol) was added to a stirred suspension of amine 66 (420 mg, 0.71 mmol) and NaBH(OAc)₃ (377 mg, 1.78 mmol) in THF (5 mL). After stirring overnight the reaction mixture was diluted with Et₂O (20 mL) and NaHCO₃ solution (20 mL). The resulting layers were separated and the aqueous layer was extracted with Et₂O (3×20 mL). The organic layers were combined and washed with brine (20 mL), then dried over Na₂SO₄, filtered and the filtrate concentrated under reduced pressure. The crude product was purified by column chromatography (0-2% EtOAc in hexanes, gradient) to give amide 65 as a colourless oil.

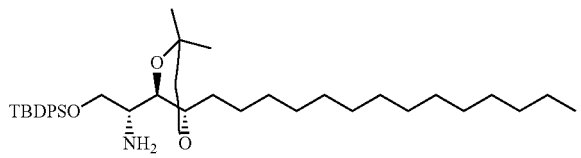

2R-amino-1-((tert-butyldiphenylsilyl)oxy)-(3R,4R—O-isopropylidene)octadecane (66)

Concentrated H₂SO₄ (4 drops) was added to a solution of sphingosine 64 (450 mg, 0.81 mmol) in dry acetone (10 mL) at 0° C. and stirred for 5 h. The reaction mixture was quenched with NaHCO₃ solution (20 mL), then concentrated under reduced pressure. The mixture was then extracted with EtOAc (3×20 mL) and the combined organic layers were washed with brine (10 mL), then dried over Na₂SO₄, filtered and the filtrate concentrated under reduced pressure. The crude product was purified by column chromatography (20% EtOAc in hexanes) to provide acetonide 67 as a colourless oil.

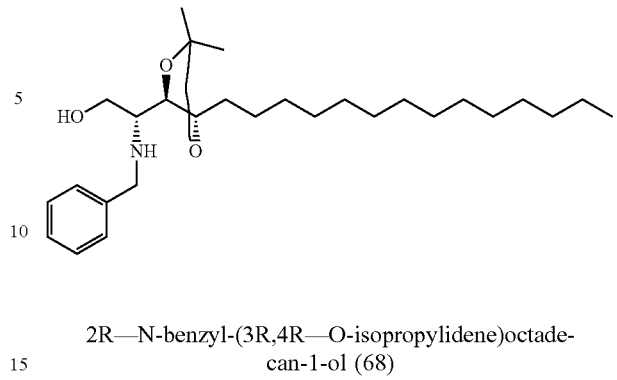

2R—N-benzyl-(3R,4R—O-isopropylidene)octadecan-1-ol (68)

TBAF (1M solution in THF, 1.27 mL, 1.27 mmol) was added to a solution of acetonide 66 (440 mg, 0.64 mmol) in THF (20 mL). The reaction mixture was stirred overnight before being quenched with H₂O (15 mL). The resulting layers were separated and the aqueous layer was extracted with EtOAc (3×15 mL). The organic layers were combined and washed with brine (15 mL), dried over Na₂SO₄, filtered and the filtrate concentrated under reduced pressure. The crude product was purified by column chromatography (25% EtOAc in hexanes) to provide alcohol 68 as a colourless oil.

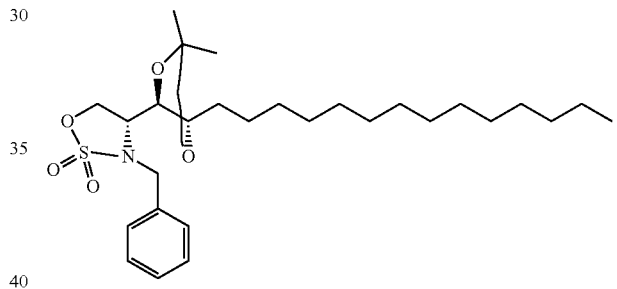

(R)-3-benzyl-4-((4R,5R)-2,2-dimethyl-5-tetradecyl-1,3-dioxolan-4-yl)-1,2,3-oxathiazolidine 2,2-dioxide (70)

A solution of amide 68 (280 mg, 0.63 mmol) in CH₂Cl₂ (5 mL) was added dropwise over 30 min to a −50° C. solution of SOCl₂ (50 µL, 0.69 mmol), imidazole (172 mg, 2.52 mmol) and NEt₃ (194 µL, 1.39 mmol) in CH₂Cl₂ (6 mL). The reaction mixture was warmed up to 0° C. and stirred for 21 h, before adding H₂O (10 mL). The organic layer was isolated and washed with brine (5 mL), dried over Na₂SO₄, filtered and the filtrate concentrated under reduced pressure to give the crude sulfamidite, which was used immediately. Rf=0.88 (30% EtOAc in hexanes)

NaIO₄ (148 mg, 0.69 mmol), RuCl₃ (14 mg, 0.064 mmol) and H₂O (5 mL) were added sequentially to a solution of crude sulfamidite in MeCN (5 mL) at 0° C. After 2.5 h the reaction mixture was diluted with H₂O (50 mL) and Et₂O (50 mL). The resulting layers were separated and the aqueous layer was extracted with Et₂O (3×35 mL). The organic layers were combined and washed with H₂O (30 mL), brine (20 mL), then dried over Na₂SO₄, filtered and the filtrate concentrated under reduced pressure. The crude product was purified by column chromatography (10% EtOAc in hexanes) to give sulfamidate 70 as a colourless oil.

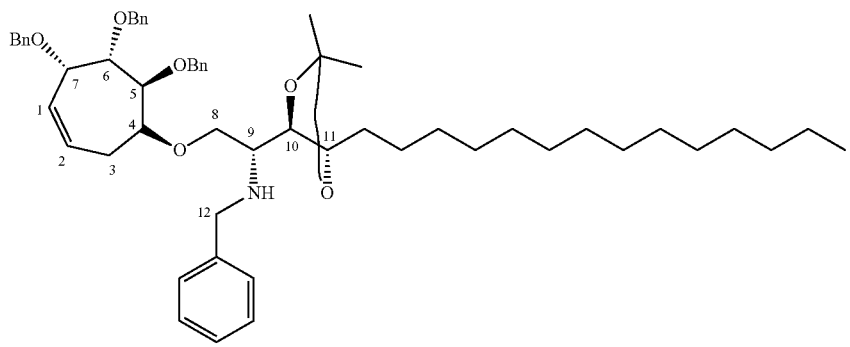

(R)—N-benzyl-1-((4R,5S)-2,2-dimethyl-5-tetradecyl-1,3-dioxolan-4-yl)-2-(((1R,5S,6S,7S)-5,6,7-tris(benzyloxy)cyclohept-3-en-1-yl)oxy)ethanamine (71)

NaH (40% wt in mineral oil, 10 mg, 0.24 mmol) was added to a solution of alcohol 54b (34 mg, 0.079 mmol) in DMF (0.25 mL) and THF (0.05 mL) at 0° C. After stirring for 1 h a solution of sulfamidate 70 (40 mg, 0.079 mmol) in THF (0.2 mL) was added at 0° C. After stirring overnight at 40° C. the reaction mixture was concentrated and the residue was dissolved in Et$_2$O (10 mL). A 20% aq. H$_2$SO$_4$ solution (10 mL) was added at 0° C. and the reaction mixture was stirred for 20 min before being neutralized with K$_2$CO$_3$ (1 g). After 40 min Et$_2$O (20 mL) and H$_2$O (20 mL) was added. The resulting layers were separated and the aqueous layer was extracted with Et$_2$O (3×35 mL). The organic layers were combined and washed with H$_2$O (30 mL), NaHCO$_3$ solution (20 mL) and brine (20 mL), then dried over Na$_2$SO$_4$, filtered and the filtrate concentrated under reduced pressure. The crude product was purified by column chromatography (10% EtOAc in hexanes) to give ether 71 as a colourless oil.

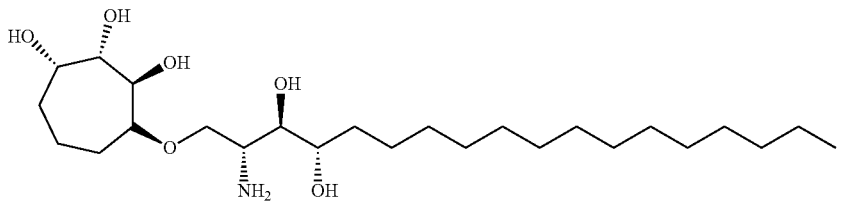

(1S,2S,3R,4R)-4-(((2R,3R,4S)-2-amino-3,4-dihydroxyoctadecyl)oxy) cycloheptane-1,2,3-triol (72)

A 1M solution of HCl (150 μL, 0.15 mmol) and Pd—C (10% wt, 32 mg, 0.03 mmol) were added to a solution of ether 71 (130 mg, 0.15 mmol) and cyclohexene (2 mL) in MeOH (10 mL) and heated under reflux. After stirring overnight the reaction mixture was cooled to rt and diluted with a 5:1 solution of CHCl$_3$:MeOH, before being filtered thought a bed of celite. The filtrate was concentrated under reduced pressure to provide the crude amine 72, which was used directly in the next step.

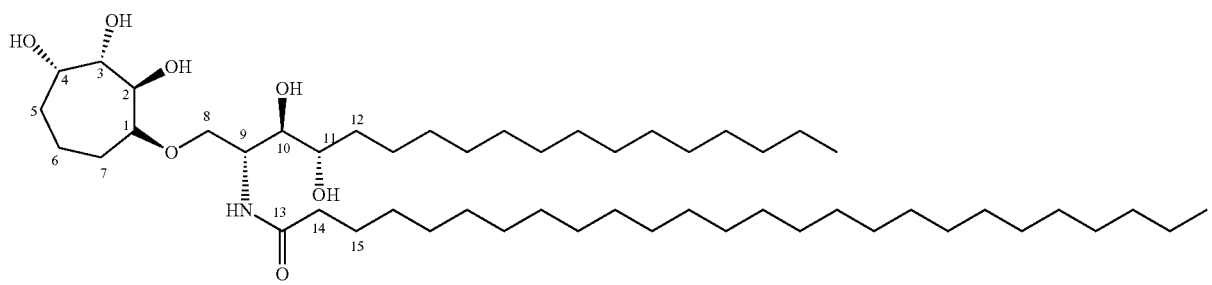

N-((2R,3R,4S)-3,4-dihydroxy-1-(((1S,2R,3S,4S)-2,3,4-trihydroxycycloheptyl) oxy)octadecan-2-yl) hexacosanamide (73)

(COCl)$_2$ (2 mL) was added to hexacosanoic acid (139 mg, 0.39 mmol) and heated at 70° C. for 2 h, after which time the solution was cooled to rt, and the (COCl)$_2$ removed under a stream of dry argon. The residual volatiles were removed under reduced pressure. The resulting crude acyl chloride was dissolved in THF (0.5 mL) and added with vigorous stirring to a solution of amine 72 (81 mg, 0.18 mmol) in THF/NaOAc$_{(aq)}$ (8M) (1:1, 2 mL). Vigorous stirring was maintained for 2 h, after which time the reaction mixture was left to stand and the layers were separated. The aqueous layer was extracted with THF (3×2.0 mL) and the organic layers were combined and concentrated under reduced pressure. The crude product was purified by column chromatography (10% MeOH in CHCl$_3$) to give amide 73 as a white solid.

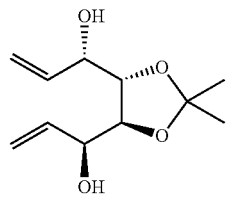

(1S,1'S)-1,1'-((4S,5S)-2,2-dimethyl-1,3-dioxolane-4,5-diyl)bis(prop-2-en-1-ol) (75)

A solution of (2R,3R)-2,3-O-isopropylidene tartrate (1.5 g, 6.9 mmol) in toluene (25 mL) was degassed according to the general procedure. DIBALH (1.0 M in toluene, 14.4 mL, 14.4 mmol) was added dropwise over 10 mins to the solution at −78° C. which was left to stir for 2.5 h at that temperature. After 2.5 h vinyl magnesium bromide (1.0 M in THF, 20.6 mL, 20.6 mmol) was added and the reaction mixture left to stir for 2 h at −78° C., before being allowed to warm up to rt slowly. The reaction was carefully quenched with NH$_4$Cl solution (50 mL) and the resulting layers were separated. The aqueous layer was extracted with EtOAc (3×35 mL). The organic layers were combined and washed with H$_2$O (20 mL) and brine (20 mL), then dried over Na$_2$SO$_4$, filtered and the filtrate concentrated under reduced pressure. The crude product was purified by column chromatography (25% EtOAc in hexanes) to give diene 75 as the major product in a mixture of diastereoisomers with a ratio of 3:1.

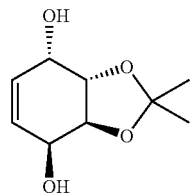

3S,3'S—O-isopropylidene-cyclohex-1-en-2S,2'S-diol (76)

A solution of diene 75 (217 mg, 1.01 mmol) in CH$_2$Cl$_2$ (230 mL) was degassed according to the general procedure. Grubbs 2$^{nd}$ generation Ru metathesis catalyst (12 mg, 0.015 mmol) was added and the solution was heated under reflux. After 2 h the solution was concentrated under reduced pressure and the crude product purified by column chromatography (5% MeOH in CHCl$_3$) to give diol 76.

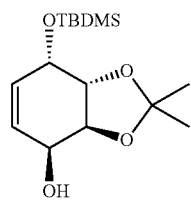 [SMILES: CC1(C)O[C@@H]2[C@@H](O1)[C@@H](O)C=C[C@@H]2O[Si](C)(C)C(C)(C)C]

4S-(tert-butyldimethylsily)oxy)-5S,6S—O-isopropylidene-cyclohex-2-enol (77)

Imidazole (275 mg, 4.04 mmol) and TBDMSCl (486 mg, 3.23 mmol) were added sequentially to a solution of diol 76 (500 mg, 2.69 mmol) in DMF (5 mL). After stirring overnight the reaction mixture was diluted with Et$_2$O (30 mL), washed with H$_2$O (15 mL) and NH$_4$Cl solution (15 mL). The organic layer was dried over Na$_2$SO$_4$, filtered and the filtrate concentrated under reduced pressure. The crude product was purified by column chromatography (20% EtOAc in hexanes) to give alcohol 77 as a colourless oil.

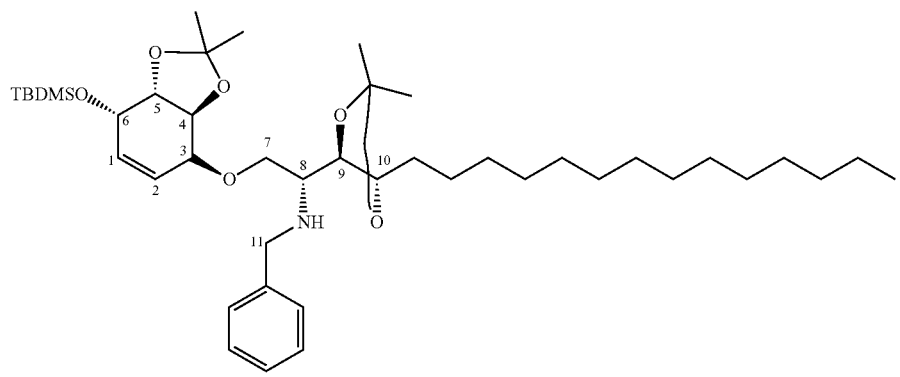

(2'R)—N-benzyl-1-((1S,2S,3S,4S)-4-((tert-butyldimethylsilyl)oxy)-2,3-O-isopropylidene-cyclohex-5-ene)-3'R,4'S—O-isopropylidene-octadecane (78)

NaH (40% wt in mineral oil, 78 mg, 1.95 mmol) was added to a solution of alcohol 77 (195 mg, 0.65 mmol) in DMF (2 mL) and THF (1 mL) at 0° C. After stirring for 1 h a solution of sulfamidate 70 (397 mg, 0.78 mmol) in THF (1 mL) was added at 0° C. After stirring overnight at 40° C. the reaction mixture was concentrated and the residue was dissolved in Et$_2$O (10 mL). A 20% aq. H$_2$SO$_4$ solution (10 mL) was added at 0° C. and the reaction mixture was stirred for 20 min before being neutralized with K$_2$CO$_3$ (1 g). After 40 min Et$_2$O (20 mL) and H$_2$O (20 mL) was added. The resulting layers were separated and the aqueous layer was extracted with Et$_2$O (3×35 mL). The organic layers were combined and washed with H$_2$O (30 mL), NaHCO$_3$ solution (20 mL) and brine (20 mL), then dried over Na$_2$SO$_4$, filtered and the filtrate concentrated under reduced pressure. The crude product was purified by column chromatography (10% EtOAc in hexanes) to give ether 78 as a colourless oil.

necessary to provide the crude amine 80, which was used directly in the next reaction. Rf=0.33 (30% MeOH in CHCl$_3$)

(COCl)$_2$ (2 mL) was added to hexacosanoic acid (21 mg, 0.054 mmol) and heated at 70° C. for 2 h, after which time the solution was cooled to rt, and the (COCl)$_2$ removed under a stream of dry argon. The residual volatiles were removed under reduced pressure. The resulting crude acyl chloride was dissolved in THF (0.5 mL) and added with vigorous stirring to a solution of amine 80 (20 mg, 0.045 mmol) in THF/NaOAc$_{(aq)}$ (8M) (1:1, 2 mL). Vigorous stirring was maintained for 2 h, after which time the reaction mixture was left to stand and the layers were separated. The aqueous layer was extracted with THF (3×2.0 mL) and the organic layers were combined and concentrated under reduced pressure. The crude product was purified by column chromatography (10% MeOH in CHCl$_3$) to give amide 81 as a white solid.

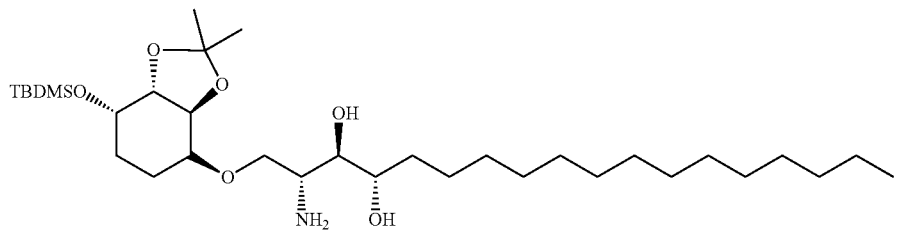

(2R,3R,4S)-2-amino-1-((1S,2S,3S,4S)-4-((tert-butyldimethylsilyl)oxy)-2,3-O-isopropylidene-cyclohexane)octadecane-3,4-diol (79)

A 1M solution of HCl (71 µL, 0.071 mmol) and Pd—C (10% wt, 15 mg, 0.014 mmol) were added to a solution of ether 78 (50 mg, 0.071 mmol) and cyclohexene (1 mL) in MeOH (5 mL) and heated under reflux. After stirring overnight the reaction mixture was cooled to rt and diluted with a 5:1 solution of CHCl$_3$:MeOH, before being filtered thought a bed of celite. The filtrate was concentrated under reduced pressure to provide the crude amine 79, which was used directly in the next step.

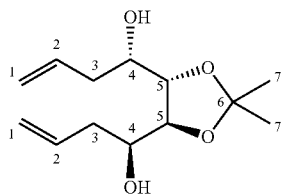

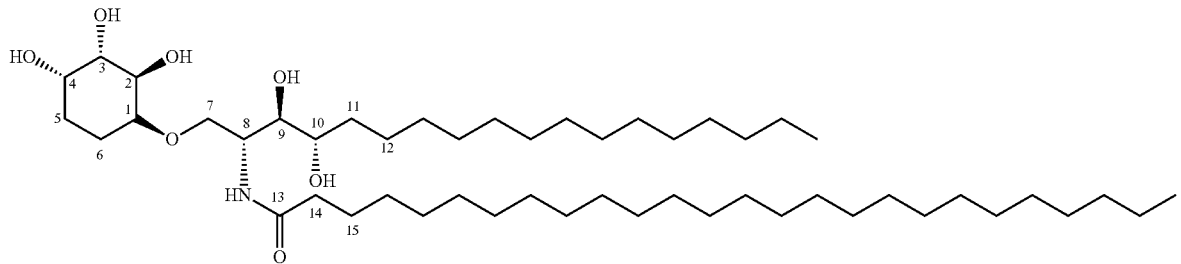

N-((2R,3R,4S)-3,4-dihydroxy-1-(((1S,2R,3S,4S)-2,3,4-trihydroxycyclohexyl) oxy)octadecan-2-yl)hexacosanamide (81)

Neat TFA (2 mL) was added to ether 79 (assuming 100% conversion, 0.071 mmol) for 15 min before removal of the TFA under reduced pressure. This procedure was repeated if

(1S,1'S)-1,1'-((4S,5S)-2,2-dimethyl-1,3-dioxolane-4,5-diyl)bis(but-3-en-1-ol) (89)

A solution of (2R,3R)-2,3-O-isopropylidene tartrate (1.88 g, 8.6 mmol) in toluene (25 mL) was degassed. DIBALH (1.0 M in toluene, 18.1 mL, 18.1 mmol) was added dropwise over 10 mins to the solution at −78° C. which was left to stir for 2.5 h at that temperature. After 2.5 h allyl magnesium bromide (1.0 M in THF, 25.9 mL, 25.9 mmol) was added and the reaction mixture left to stir for 2 h at −78° C., before being allowed to warm up to rt slowly. The reaction was carefully quenched with NH₄Cl solution (50 mL) and the resulting layers were separated. The aqueous layer was extracted with EtOAc (3×35 mL). The organic layers were combined and washed with H₂O (20 mL) and brine (20 mL), then dried over Na₂SO₄, filtered and the filtrate concentrated under reduced pressure. The crude product was purified by column chromatography (25% EtOAc in hexanes) to give diene 89.

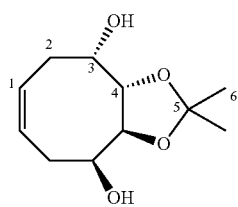

4S,4'S—O-isopropylidene-cyclooct-1-en-4,4'-diol (90)

A solution of diene 89 (400 mg, 1.65 mmol) in CH₂Cl₂ (750 mL) was degassed. Grubbs $2^{nd}$ generation Ru metathesis catalyst (21 mg, 0.025 mmol) was added and the solution was heated under reflux. After 2 h the solution was concentrated under reduced pressure and the crude product purified by column chromatography (40% EtOAc in hexanes) to give diol 90.

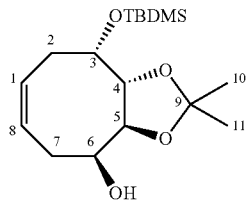 [SMILES: CC1(C)O[C@@H]2[C@@H](O1)[C@@H](O)C/C=C\C[C@@H]2O[Si](C)(C)C(C)(C)C]

6-(tert-butyldimethylsilyl)oxy)-7S,8S—O-isopropylidene-cyclooct-3-en-1-ol (91)

Imidazole (140 mg, 2.1 mmol) and TBDMSCl (187 mg, 1.2 mmol) were added sequentially to a solution of diol 90 (220 mg, 1.0 mmol) in DMF (5 mL). After stirring overnight the reaction mixture was diluted with Et₂O (30 mL), washed with H₂O (15 mL) and NH₄Cl solution (15 mL). The organic layer was dried over Na₂SO₄, filtered and the filtrate concentrated under reduced pressure. The crude product was purified by column chromatography (20% EtOAc in hexanes) to give alcohol 91 as a colourless oil.

Biology—Linker Analogues

The biological activity of each of the α-GalCer thioamide 6, α-GalCer urea 7, and α-GalCer carbamate 8 analogues and the ThrCer thioamide 9, ThrCer urea 10, and ThrCer caarbamate 11 analogues was investigated alongside α-GalCer 1 and ThrCer 2. In a preliminary screen, all eight compounds were tested for their ability to stimulate the iNKT cell hybridoma DN32, following pulsing of C1R-mCD1d cells with various concentrations of ligands. The concentration of IL-2 in the supernatant released after iNKT cell activation was measured using an enzyme-linked immunosorbent assay (ELISA). Encouragingly, these experiments demonstrated that both ThrCer-thioamide 9 and ThrCer-carbamate 11 induced increased activation compared with ThrCer 2, whereas the ThrCer-urea analogue 10 led to weak stimulation and only at high concentrations (FIG. 1B). A similar hierarchy was observed for the α-GalCer analogues, although the differences, particularly at high concentration, were less pronounced (FIG. 1A).

In another in vitro experiment to test functional activity, this time using a human model, human iNKT cells were co-cultured for 40 h with C1R-hCD1d cells that had been pulsed with 100 ng mL⁻¹ concentrations of vehicle, α-GalCer 1, α-GalCer-thioamide 6, α-GalCer-urea 7, and α-GalCer-carbamate 8 (FIG. 2A) and, ThrCer 2, ThrCer-thioamide 9, ThrCer-urea 10, and ThrCer-carbamate 11 (FIG. 2B). In this assay, the ability of the various ligands to activate iNKT cells was assessed by determining the levels of IFNγ production after 40 h by ELISA. Once again, all three ThrCer analogues were shown to stimulate human iNKT cells, albeit at lower levels than the αGalCer analogues, which is in accord with the behaviour of the two parent compounds. In agreement with the murine iNKT cell data (FIG. 1), the weakest ligand at 100 ng mL⁻¹ was again ThrCer-urea 10; however in this assay, ThrCer-thioamide 9 and ThrCer-carbamate 11 were now more comparable to ThrCer in their behaviour (FIG. 2B). All of the α-GalCer analogues stimulated human iNKT cells, with the urea analogue 7 proving to be the weakest activator at low concentrations (FIG. 2A).

Since the two urea derivatives 7 and 10 displayed the weakest activity in in vitro experiments, further studies focused solely on the thioamide and carbamate derivatives of ThrCer and α-GalCer. These analogues were next investigated in vivo, alongside the parent compounds and Th2-biasing molecule OCH9 (12, below), specifically to assess their ability to effect DC maturation as well as their cytokine response profile.

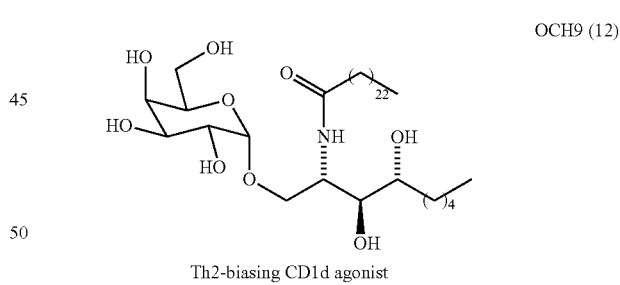

Th2-biasing CD1d agonist

Figure 4B:
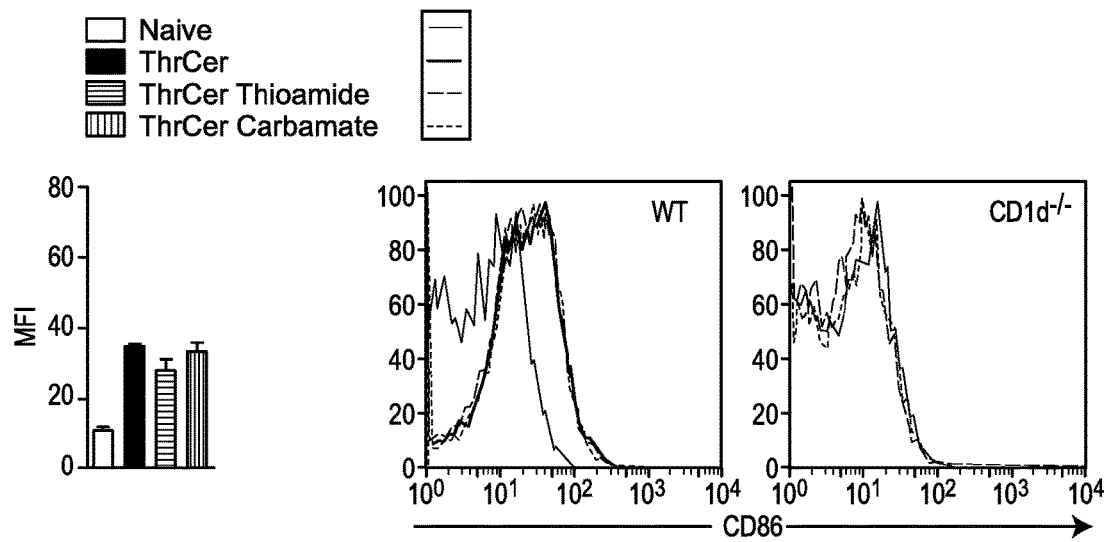

To this end, 1 μg lipid was injected intravenously (i.v.) into wildtype C57 BL/6 or C57 BL/6 CD1d −/− (NKT cell-deficient) mice. After 2 h, the mice were tail-bled and IL-4 levels in the serum measured by ELISA (FIG. 3). At 18 h, the mice were sacrificed and blood serum levels of IFNγ were measured by ELISA (FIG. 3), and cells harvested from the spleen were used to determine the extent of DC maturation by measuring the expression of the co-stimulatory molecule, CD86 using fluoresence-activated cell sorting (FACS) analysis (FIG. 4).

The in vivo activation of iNKT cells with the α-GalCer and ThrCer analogues was determined by analyzing the cytokine profile in blood serum at 2 h and 18 h. Thus, α-GalCer analogues 6 and 8 showed a marked decrease in the ability to stimulate iNKT cells to produce IL-4 at 2 h post injection compared with α-GalCer, but both compounds were able to maintain IFNγ production at 18 h, consistent with that of α-GalCer (FIG. 3A). Differences in cytokine production were even more pronounced with the weaker ThrCer agonists 9 and 11, both of which did not stimulate iNKT cells to produce IL-4 at all when assayed at 2 h, but were still able to produce IFNγ at 18 h (FIG. 3B). No cytokine production was detected in CD1d −/− mice injected with the α-GalCer and ThrCer analogues. Since the presentation of CD1d-lipid complex by DC to iNKT cells results in activation and the subsequent maturation of DC, we also determined whether there was any difference in the ability of DC to upregulate the co-stimulatory molecule, CD86, following i.v. delivery of α-GalCer and ThrCer analogues. Pleasingly, both sets of analogues induced DC maturation to a similar degree as the parent α-GalCer and ThrCer compounds in wildtype mice but not in CD1d −/− mice (FIG. 4).

Figure 5A:
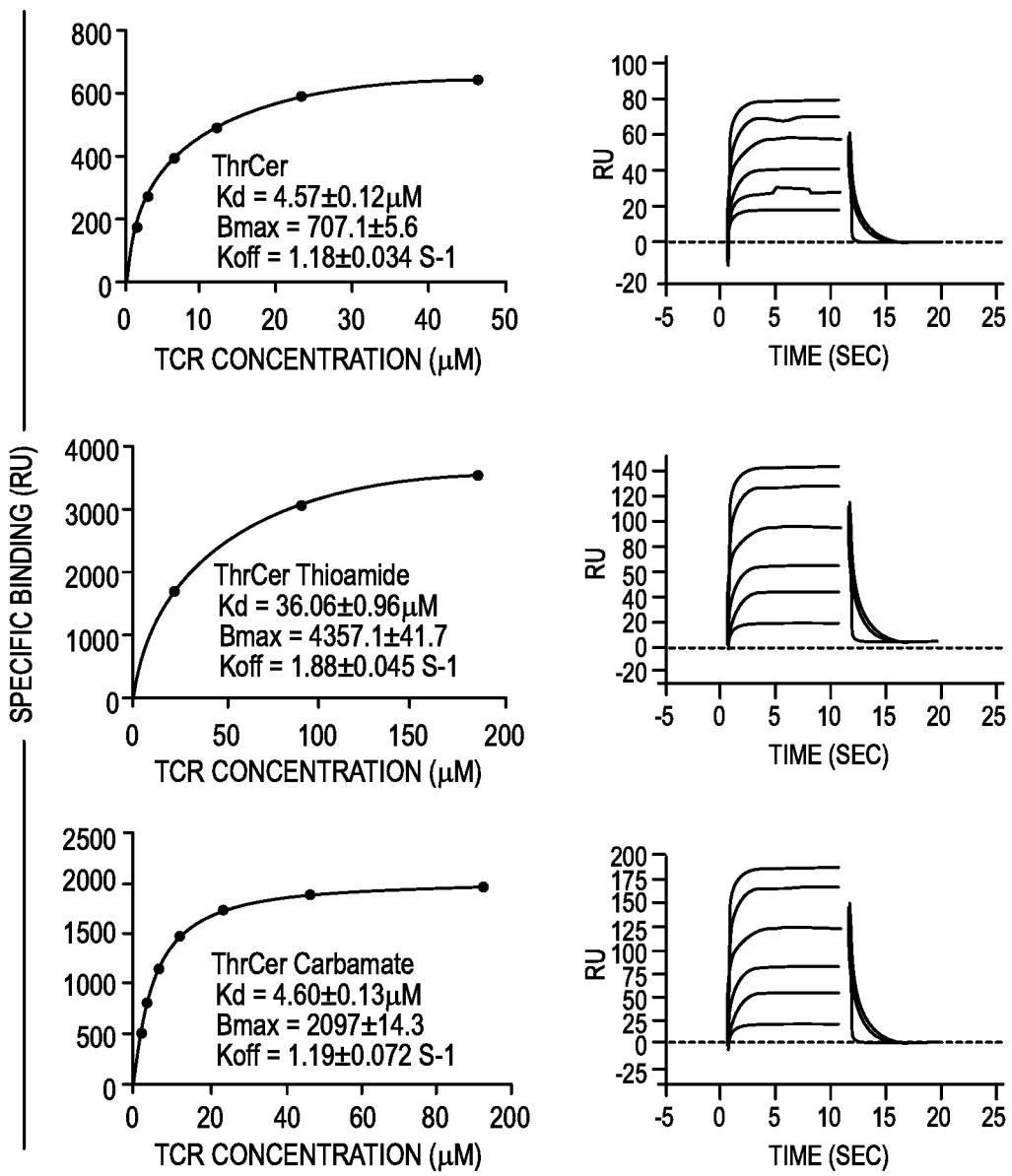
FIG. 5 shows SPR experiments used to measure the affinity and kinetics of human iNKT cell T cell receptors (TCRs) for hCD1d cells loaded with α-GalCer, ThrCer, α-GalCer thioamide, α-GalCer carbamate, ThrCer thioamide, and ThrCer carbamate analogues.
Figure 5B:
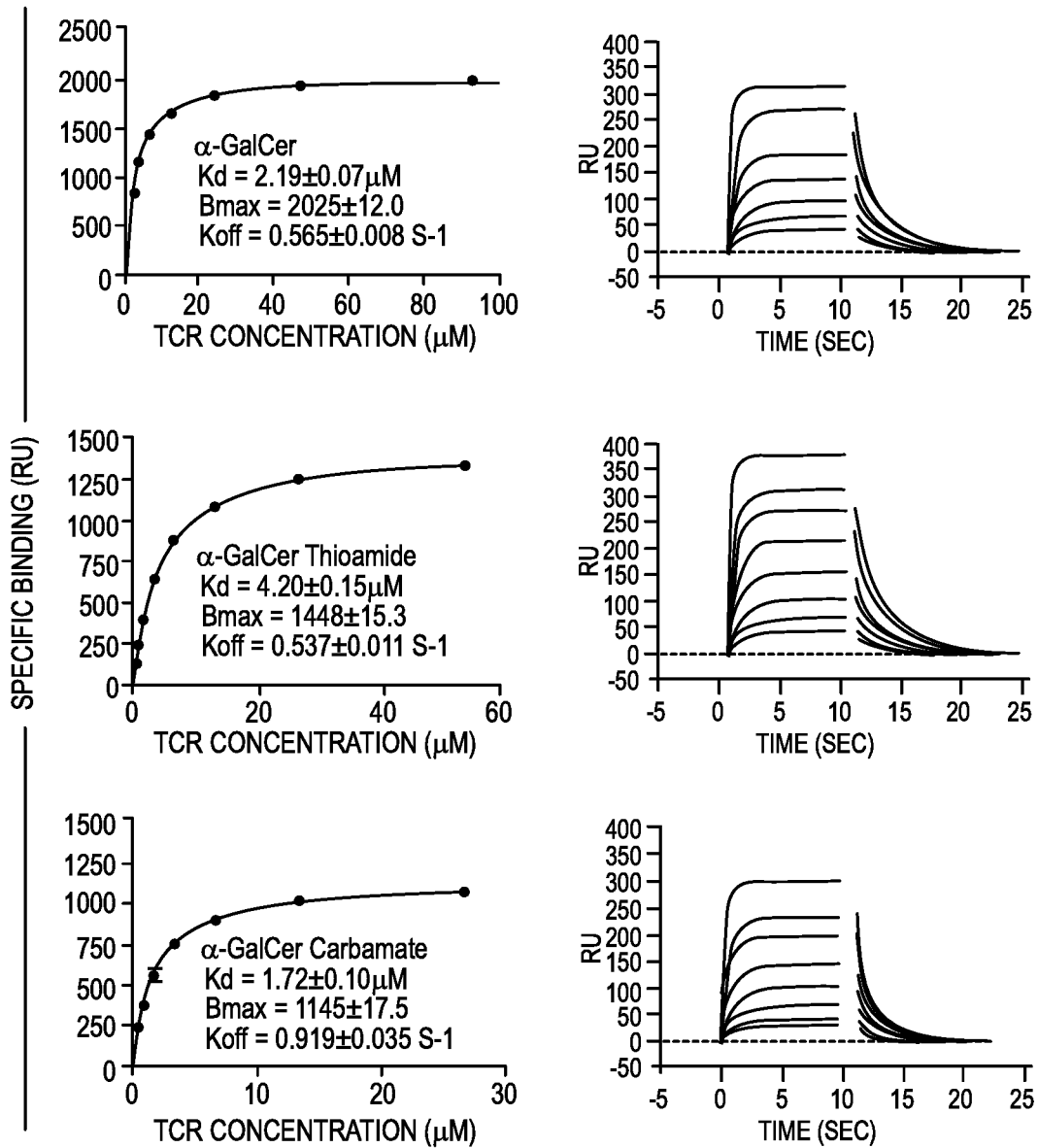

The binding kinetics of these ThrCer and α-GalCer analogue compounds were examined. To this end, bacterially-expressed hCD1d and β-2-microglobulin (β2 M) molecules were refolded with the thioamide, and carbamate analogues of both α-GalCer and ThrCer by oxidative refolding chromatography, and then biotinylated. The urea analogues of α-GalCer and ThrCer could not be refolded, and therefore, no surface plasmon resonance (SPR) data are available for these molecules. Soluble human iNKT TCR was prepared. SPR experiments were used to measure the affinity and kinetics of human iNKT cell TCRs for hCD1d loaded with α-GalCer, ThrCer, and their thioamide and carbamate analogues (FIG. 5). To this end, increasing concentrations of TCR were injected for 5 seconds over the indicated complex immobilized on the BIAcore chip until the specific binding reached its plateau. $K_d$ and $B_{max}$ were calculated by fitting the data using non-linear regression binding kinetics model (FIG. 5). Kinetic measurements for the $k_{off}$ were calculated using BIAevaluation software kit; $k_{on}$, values were calculated from the experimental $k_{off}$ and $K_d$.

TABLE

| lipid on CD1d | experimental $K_d$ (μM) | experimental $k_{off}$ (s$^{-1}$) | calculated $k_{on}$ (×10$^5$ M$^{-1}$ s$^{-1}$) |
|---|---|---|---|
| ThrCer 2 | 4.57 ± 0.12 | 1.18 ± 0.034 | 2.58 ± 0.10 |
| ThrCer thioamide 9 | 36.06 ± 0.96 | 1.88 ± 0.045 | 5.20 ± 0.26 |
| ThrCer carbamate 11 | 4.60 ± 0.13 | 1.19 ± 0.072 | 2.59 ± 0.17 |
| α-GalCer 1 | 2.19 ± 0.07 | 0.565 ± 0.008 | 2.58 ± 0.09 |
| α-GalCer thioamide 6 | 4.20 ± 0.15 | 0.537 ± 0.011 | 1.28 ± 0.05 |
| α-GalCer carbamate 8 | 1.72 ± 0.10 | 0.919 ± 0.035 | 5.34 ± 0.37 |

The mechanisms by which glycolipid CD1d agonists are able to modulate the cytokine response on iNKT cell activation are complex. The stability of the glycolipid-CD1d complex, and its TCR affinity have both been invoked to be important; however more recently the metabolic stability of the glycolipid, along with the cellular location of loading have also been proposed to play a role. Indirect effects resulting from iNKT cell activation also need to be considered; for example the Th2-biasing molecule, OCH9 12, has been shown to reduce the level of CD40L expression by activated iNKT cells, which in turn reduces IL-12 production and thence downstream IFNγ production from NK cells.

The in vivo experiments for the α-GalCer analogues show that the thioamide and carbamate derivatives, 6 and 8, respectively, both display a cytokine bias towards IFNγ compared with α-GalCer, resulting from a reduction in IL-4 production relative to the parent α-GalCer 1, rather than an increase in IFNγ production, which in both cases was similar to that generated by α-GalCer 1. Results for the ThrCer derivatives were more significant in that these displayed a similar but more pronounced trend. Compared with α-GalCer 1, ThrCer 2 is a weaker activator of iNKT cells, although it displays a similar cytokine profile. ThrCer-thioamide 9 and ThrCer-carbamate 11 displayed no IL-4 production, when assayed at 2 h; however they showed levels of IFNγ production at 18 h, which were higher than those shown for ThrCer 2 and only four times lower than that displayed by α-GalCer 1.

Both the α-GalCer and ThrCer analogues induced DC maturation to a similar degree as the parent α-GalCer and ThrCer compounds in wildtype mice but not in CD1d−/− mice. In terms of binding affinity of the TCR for glycolipid-loaded hCD1d, $K_d$ values for the hCD1d-carbamate-TCR complexes in both series were comparable to those measured for the parent compounds. The iNKT cell TCR exhibited slightly lower binding affinity for hCD1d loaded with α-GalCer-thioamide 6 compared with hCD1d/α-GalCer, whereas binding affinity for hCD1d loaded with ThrCer-thioamide 9 was interestingly an order of magnitude lower than that for hCD1d/ThrCer 2. The binding kinetics experiment showed that these lower binding affinities are a consequence of a faster off rate and a slower on rate of the hCD1d-thioamide-TCR complex compared to CD1d complexes with the parent molecules. This observation is comparable to the kinetics displayed by the Th2-biasing α-GalCer analogue, OCH9 whose weak binding ($K_d$ of 123±9.08 μM) was attributed to both, a decrease in the $k_{on}$ (2.3× 10$^4$±1×10$^3$ M$^{-1}$ s$^{-1}$), as well as an increased $k_{off}$ (2.67±0.12 s$^{-1}$). These iNKT cell TCR binding affinity data for the CD1d-glycolipid complexes do not show a clear correlation with the observed cytokine response.

A recent study made a direct comparison between the Th2-biasing OCH9 glycolipid 12 and the Th1-biasing C-glycosyl analogue of α-GalCer 13. It showed that both OCH9 12 and the C-glycosyl analogue of α-GalCer 13 displayed weaker interactions than α-GalCer with the iNKT cell TCRs. The differences in cytokine response profiles was attributed to other factors including their differing pharmacokinetics properties, and their ability to transactivate other cytokinereleasing T-lymphocytes such as NK cells. When such transactivation requires prolonged lifetime after initial injection, metabolically more stable glycolipid analogues should function better. A similar observation was made with the neoglycolipid α-carba-GalCer, which induces a Th1-biased cytokine response profile upon iNKT cell activation. Having replaced the amide residue with metabolically more stable functionality, all three structural analogues, and in particular the non-glycosidic threitol derivatives 9, 10 and 11, which are also not susceptible to glycosidase-mediated hydrolysis, were expected to exhibit prolonged lifetimes in vivo, and for this reason, it was postulated that this might lead to increased IFNγ production. This hypothesis appears to have been borne out, at least in part, in the ThrCer series with the thioamide and carbamate analogues. In both α-GalCer and ThrCer series, the urea analogues displayed poor activity and binding and kinetics data for these two substrates were unattainable, which may suggest that the additional NH functionality incorporated into the acyl chain disrupts glycolipid binding and subsequent presentation.

Ever since it was demonstrated that α-GalCer 1 functions as a potent CD agonist, numerous structural modifications have probed structure-activity relationships and led to the discovery of CD1d agonists that are capable of polarizing cytokine production. Structural variation around the amide bond in 1 has to-date received scant attention. To this end, thioamide, carbamate and urea analogues of α-GalCer and its non-glycosidic analogue, ThrCer, were prepared and an investigation of their biological activity was conducted. Whilst the carbamate and thioamide analogues of α-GalCer are similar in behaviour to the parent molecule, the same changes in ThrCer, led to two substrates that display a markedly different cytokine response profile upon iNKT cell activation. This study shows for the first time that amide isosteres of CD1d agonists can be used to elicit significant changes in cytokine response. Although the factors that govern the cytokine profile are likely multifactorial, it is postulated that providing the glycolipid binds in a viable conformation for presentation to iNKT cell TCRs, increased metabolic stability is important for prolonged activation of iNKT cells. By this reasoning, the thioamide analogue of the C-glycosyl α-GalCer derivative are worthy of investigation.

Biology—Cyclic Analogues

Binding affinity of iNKT TCR to various compounds, as noted below, was assessed.

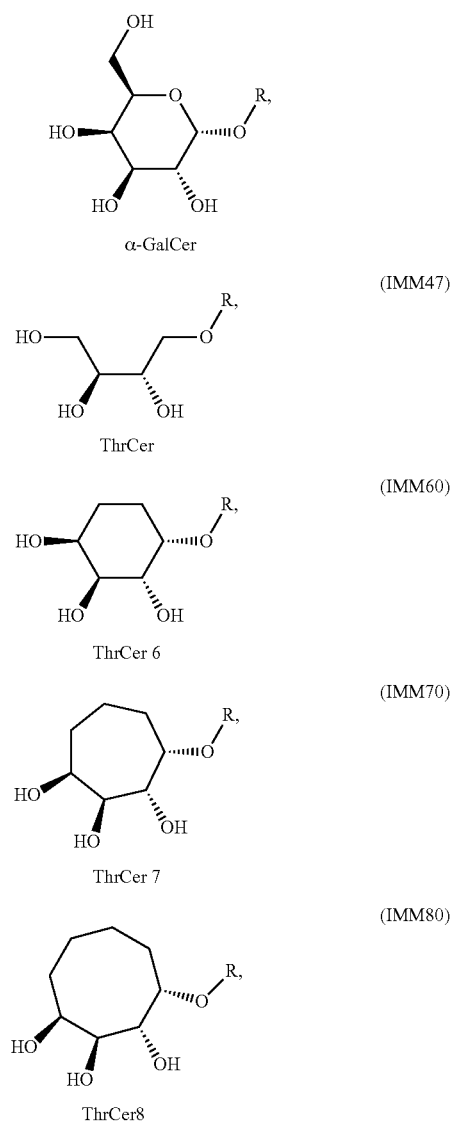

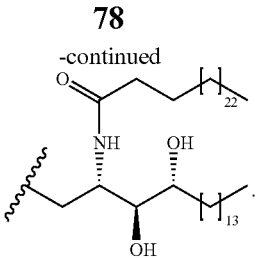

Figure 6:
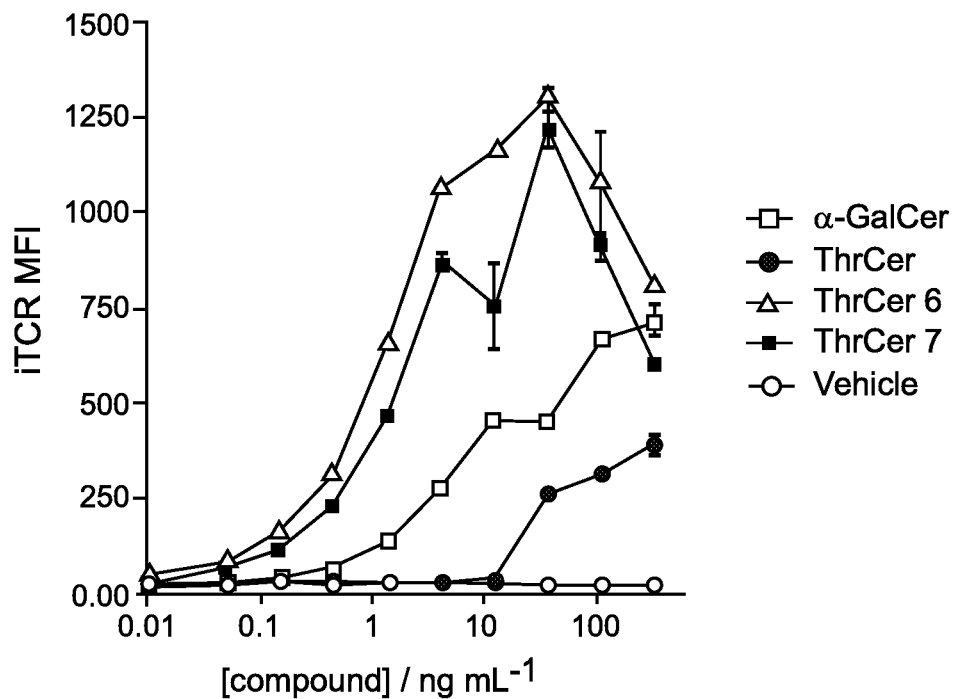
FIG. 6. Binding affinity of iNKT TCR to ThrCer6 and ThrCer7 CD1d complex. C1R-hCD1d cells were pulsed with various ligands, as noted, and the affinity of iNKT TCR-tetramer determined by flow cytometry as measured by median Fluorescent Intensity (MFI)).
Figure 7:
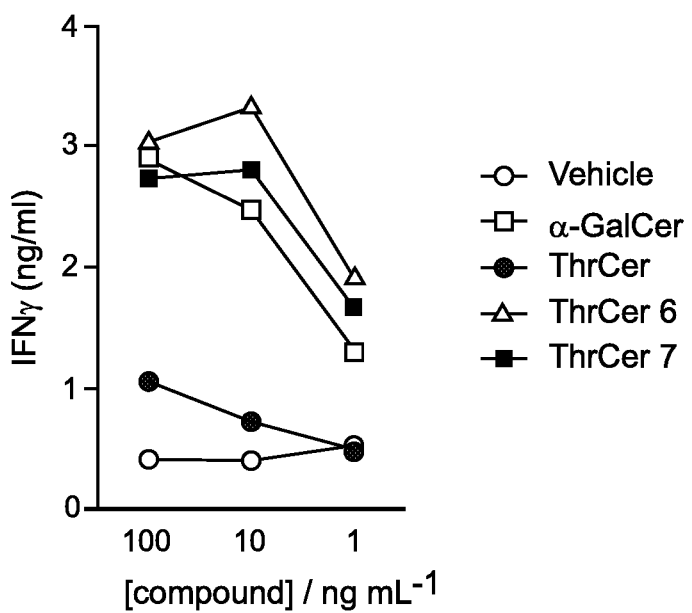
FIG. 7. Binding affinity of iNKT TCR in the presence of different ligands. C1R-hCD1d cells pulsed with various ligands, as noted, and IFNγ levels measured in their supernatant by ELISA.
Figure 8:
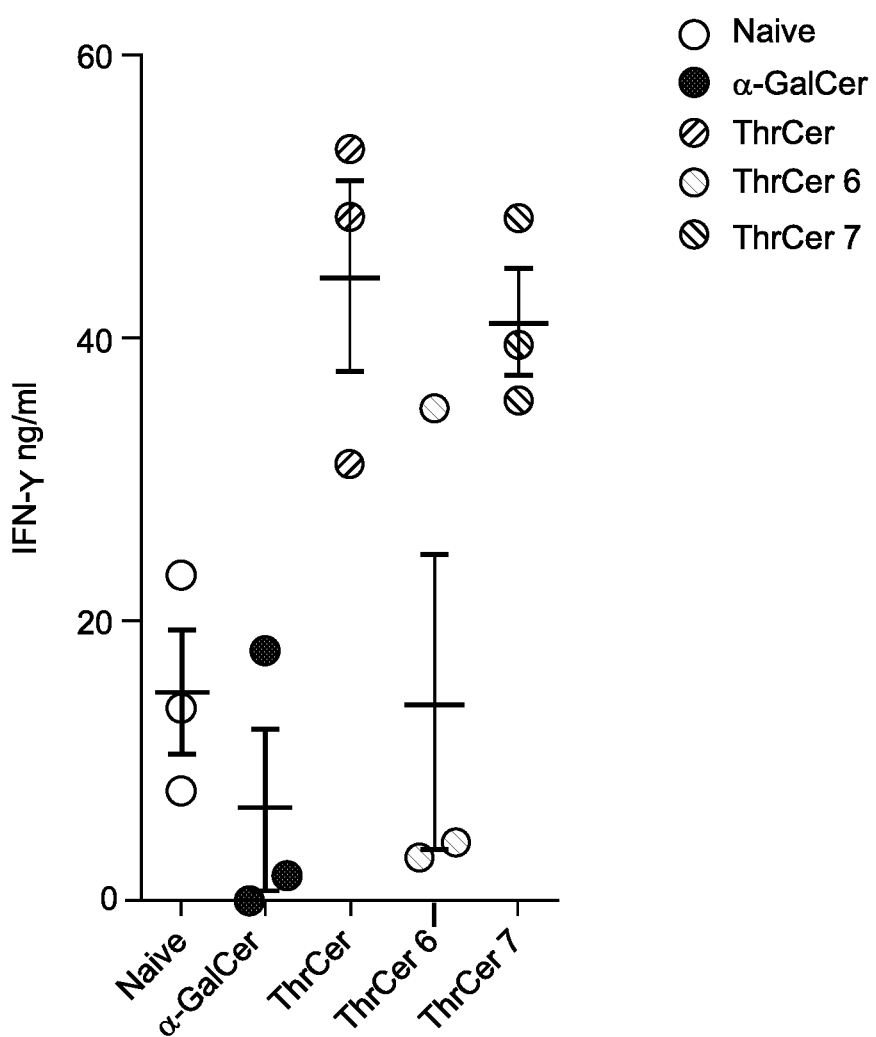
FIG. 8. Recovery of iNKT cells from activation-induced anergy. Splenocytes cultured for 60 h in the presence of various ligands and IFNγ levels measured in the supernatant by ELISA.

C1R-hCD1d cells were pulsed with each ligand noted above and the affinity of iNKT TCR-tetramer was determined by flow cytometry as measured by median Fluorescent Intensity (MFI). The results are shown in FIG. 6. The supernatant was tested for IFNγ by ELISA, and the results are shown in FIG. 7. Mice (n=3) were immunized with 0.1 µg of each compound on day −28. Splenocytes were cultured for 60 hours in the presence of α-GalCer and the supernatants were tested for IFNγ by ELISA, the results are shown in FIG. 8.

Figure 9A:
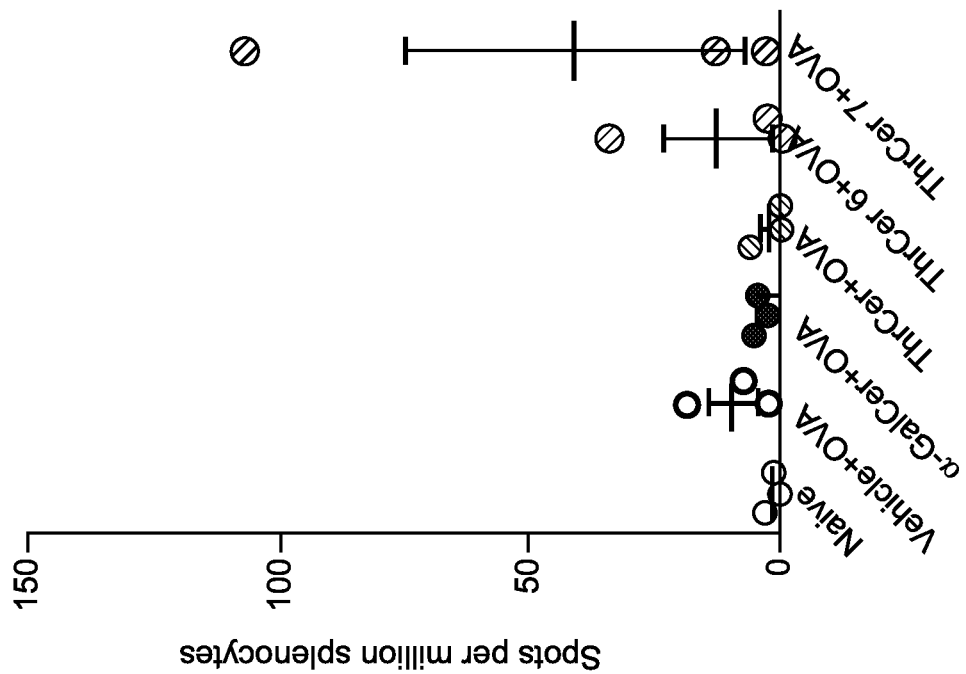
FIG. 9. Adjuvant activity of various ligands. Splenocytes were contacted for 18 hours with 800 µg OVA, 1 µg lipid, and OVA-specific MHC I (FIG. 9A) and MHCII (FIG. 9B) peptides. IFNγ levels measured after 18 hours by ELISpot and expressed as spots per million splenocytes.
Figure 9B:
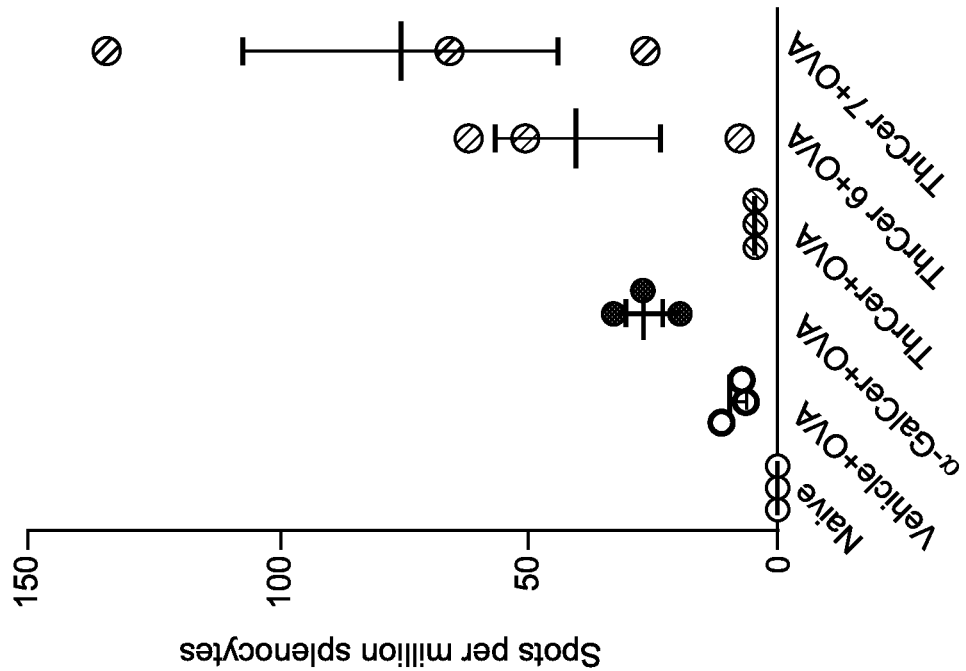

Following immunization with 800 µg OVA and 1 µg lipids i.v. at day −7, splenocytes were cultured in vitro in the presence of OVA specific MHC I (A) and MHCII (B) peptides. IFNγ release was determined at 18 hours by ELISpot and expressed as the number of spot per million splenocytes. The results are shown in FIG. 9.

Figure 10:
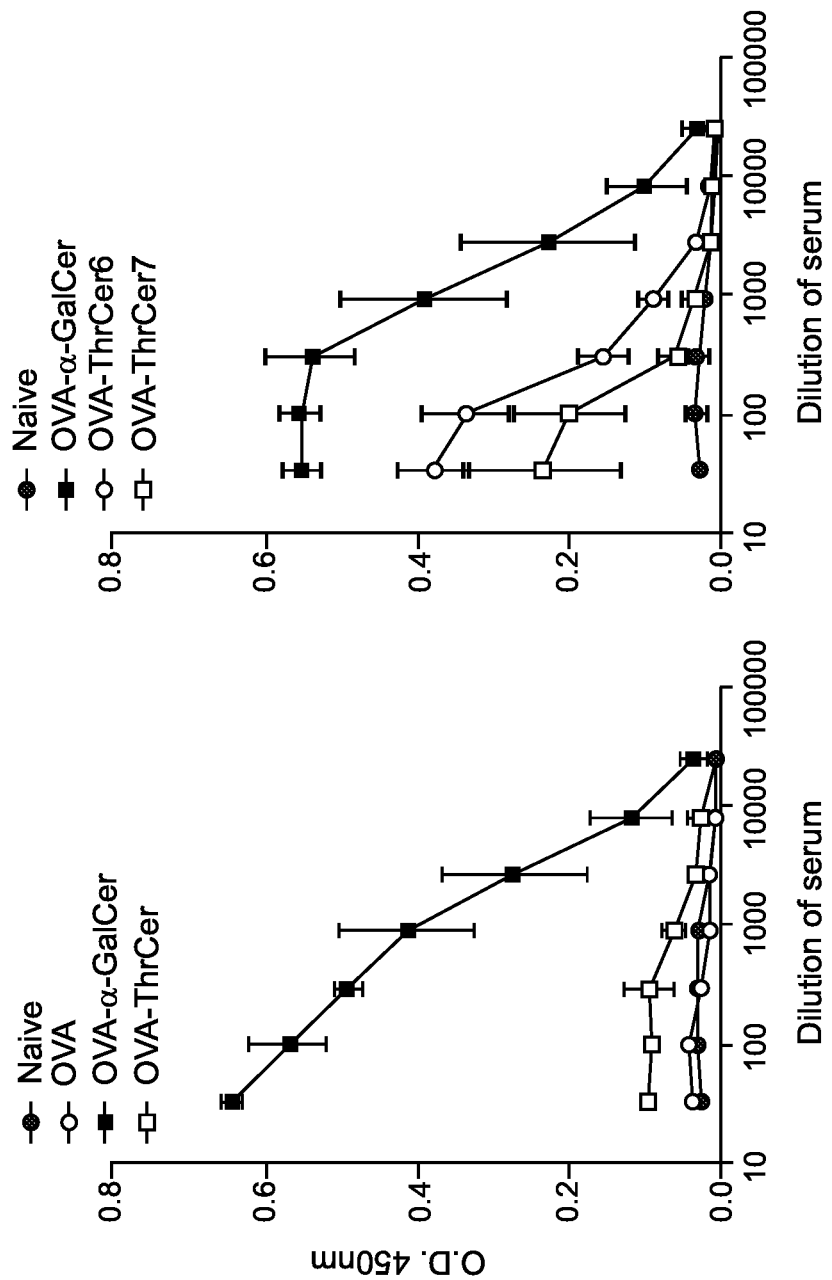
FIG. 10. Adjuvant activity of various ligands. Splenocytes were contacted for 18 hours with 800 µg OVA, 1 µg lipid, and OVA-specific MHC I and MHCII peptides. OVA IgG levels measured after 18 hours.

Adjuvant activity of ThrCer 6 and ThrCer 7 were assessed. Following immunization with 800 µg OVA and 1 µg lipids i.v. at day −7, mice were bled and sera tested by ELISA for the presence of OVA-specific IgGs. The results are shown in FIG. 10.

Biology Studies of IMM47, IMM60, IMM70, and IMM80

Mice and reagents: C57BL/6 wild-type and CD1d$^{-/-}$ (NKT deficient) mice were used. Animal experiments were carried out under the authority of a U.K. Home Office Project License. Lipid compounds α-GalCer, IMM47 (threitolceramide), IMM60 (ThrCer 6-membered ring), IMM70 (ThrCer 7-membered ring), and IMM80 (ThrCer 8-membered ring), were solubilized in vehicle (150 mM NaCl and 0.5% Tween 20; Sigma, UK). Hiltonol (Poly I:C; [Oncovir Inc, USA]) was diluted in phosphate buffered saline (PBS; Oxoid, UK) prior to injection.

In vitro and in vivo activation of iNKT cells: For in vitro re-stimulation of iNKT cells, 5×10$^5$ C57BL/6 splenocytes were loaded with either 100 ng/ml, 10 ng/ml or 1 ng/ml α-GalCer or vehicle for 48 hours and the presence of IFNγ in supernatant determined by ELISA (eBioscience).

For in vivo activation of iNKT cells, C57BL/6 wild-type or CD1d$^{-/-}$ (NKT cell deficient) mice were injected intravenously with 1 µg lipids and blood sera taken at 2 hours or 18 hours and the presence of IL-4 and IFNγ determined by ELISA (eBioscience).

Protein expression and purification: hCD1d and β2m were refolded with α-GalCer, IMM47, IMM60, IMM70 or IMM80 by oxidative chromatography. In summary, CD1d and β2m were overexpressed in *E. coli* BL21 using a prokaryotic expression system (Novagen, UK). The individual proteins were purified from inclusion bodies, then refolded with the corresponding lipid. The complex was biotinylated and purified.

Preparation of human iNKT TCR: Soluble TCR was prepared according to the protocol described by McCarthy et al., *J Exp Med*, 204 (5), 1131-44 (2007), where both Vα24 and Vβ11 chains were individually overexpressed in *E. coli* and purified from the inclusion bodies, then refolded and purified to generate the TCR heterodimers.

Surface plasmon resonance: SPR experiments were performed with a model 3000 BIAcore to measure the affinity and kinetics of iNKT TCR binding to hCD1d-ligand complexes. In brief, approximately 1000 RU of the biotinylated hCD1d-lipid complexes, were immobilized onto streptavidin-coated CM5 sensor chips (BIAcore). Injections of purified TCR serial dilutions were passed on the immobilized hCD1d-lipid at a flow rate of 10 µl/min for the equilibrium binding experiments, or 50 µl/min for the kinetics experiments. The $K_d$ values were calculated by fitting the data from the equilibrium binding experiment to a non-linear regression saturation binding model (GraphPad Prism 5.0), whereas the $k_{off}$ data were estimated from the kinetics experiments by fitting the data to the 1:1 Langmuir binding model using the BIAevaal 3.1 software (BIAcore).

Figure 19:
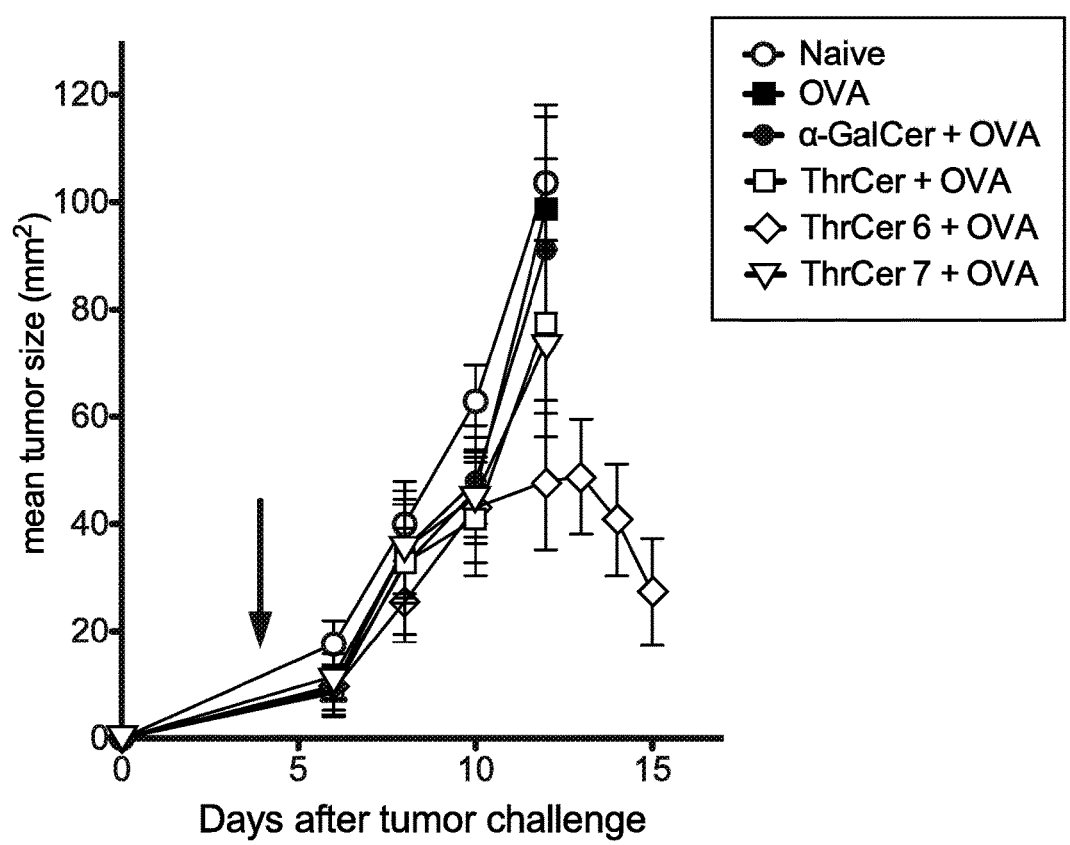
FIG. 19 is a graph analyzing tumor size in mice at various times after tumor challenge in mice treated with indicated compounds. The data show that IMM60 (ThrCer6) induced tumor regression.

Comparative Analysis of Alpha-GalCer, ThrCer, IMM60, and IMM70 on Tumor Regression Mice were injected with $1 \times 10^6$ EG7 cells (EL4 cells transfected with full length ovalbumin). Four days later (when tumor was palpable) the mice were immunized with 800 µg of ovalbumin (OVA) alone or various lipids: (alpha-GalCer, ThrCer, IMM60, and IMM70. Mean tumor size was assessed at various days after challenge. As summarized in FIG. 19, IMM60 was the only compound of those tested that induced regression of the established tumour.

In Vivo Anergy of iNKT Cells

Figure 13:
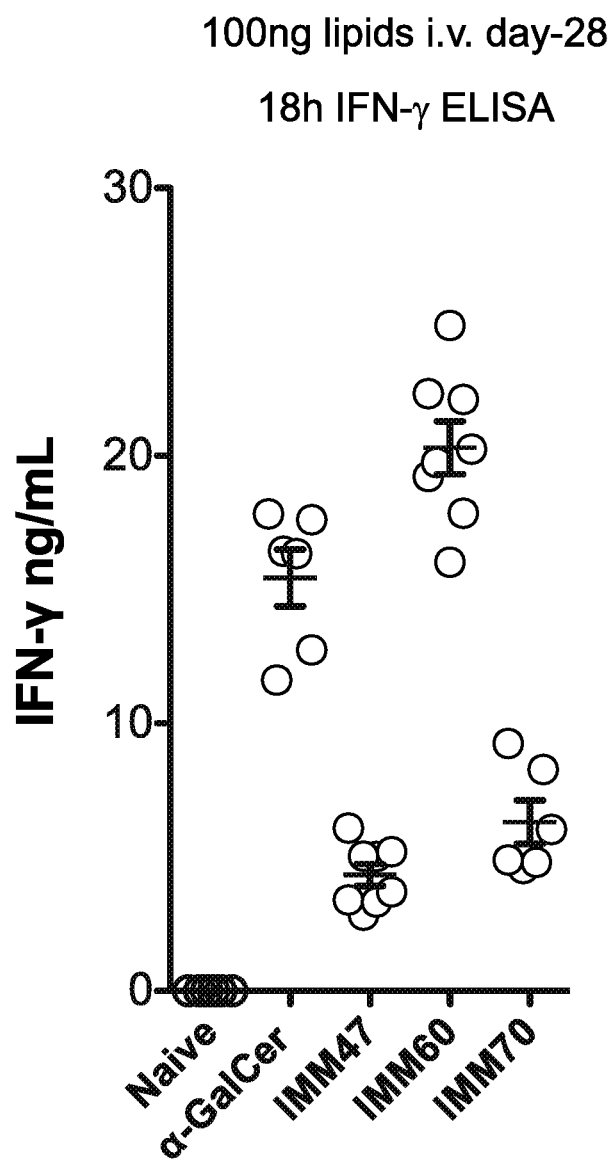
FIG. 13 is a graph showing the level of IFNγ expression in naïve mice and in mice 18 hours after being immunized with alpha-GalCer, IMM47, IMM60 or IMM70.
Figure 14:
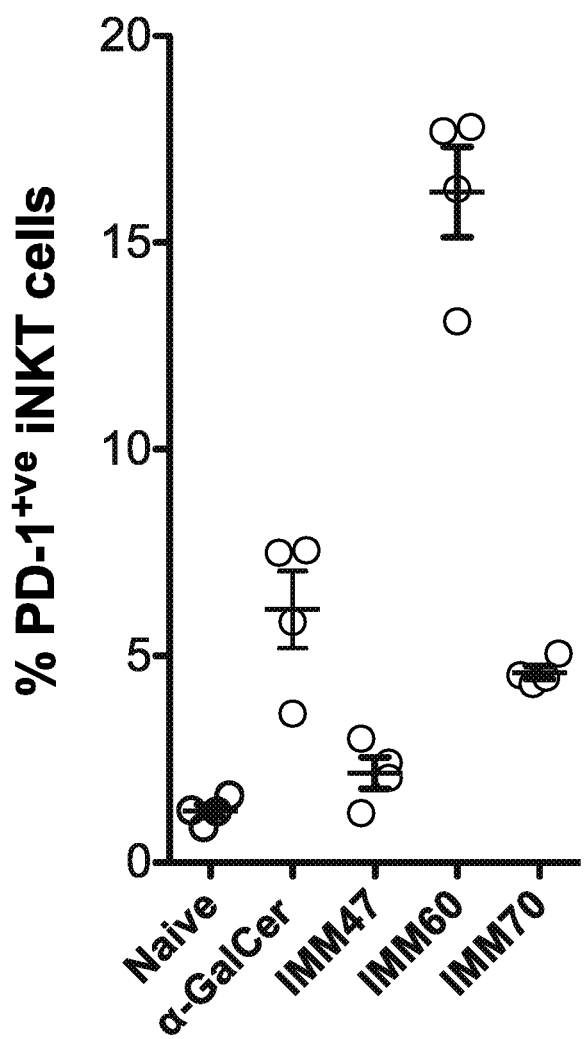
FIG. 14 is a graph showing the level of PD1 expression in naïve mice and in mice 28 days after being immunized with alpha-GalCer, IMM47, IMM60 or IMM70.

The following experiment was designed to assess the in vivo anergy of iNKT cells as defined by their ability to enhance antigen-specific T- and B-cell responses. The experimental design is set forth in FIG. 12. Mice were pre-conditioned at day −28 with individual lipids shown in FIG. 12 (100 ng i.v. of either alphaGalCer, IMM47, IMM60, or IMM70). Eighteen hours later, mice were bled to assess iNKT cell activation, as defined by IFN-gamma (determined by ELISA (eBioscience)), results shown in FIG. 13. At day zero (28 days after lipid preconditioning), expression of the iNKT cell activation marker PD1 was measured in splenic iNKT cells (FIG. 14). These two results show that IMM60 induces a stronger iNKT cell activation than IMM47, IMM70, or even alphaGalCer. (This observation is consistent with IMM60's ability to induce stronger T and B cell responses after 7 day priming as described below.) However, IMM60 also caused enhanced DC lysis and enhanced anergy as described below.

Figure 12:
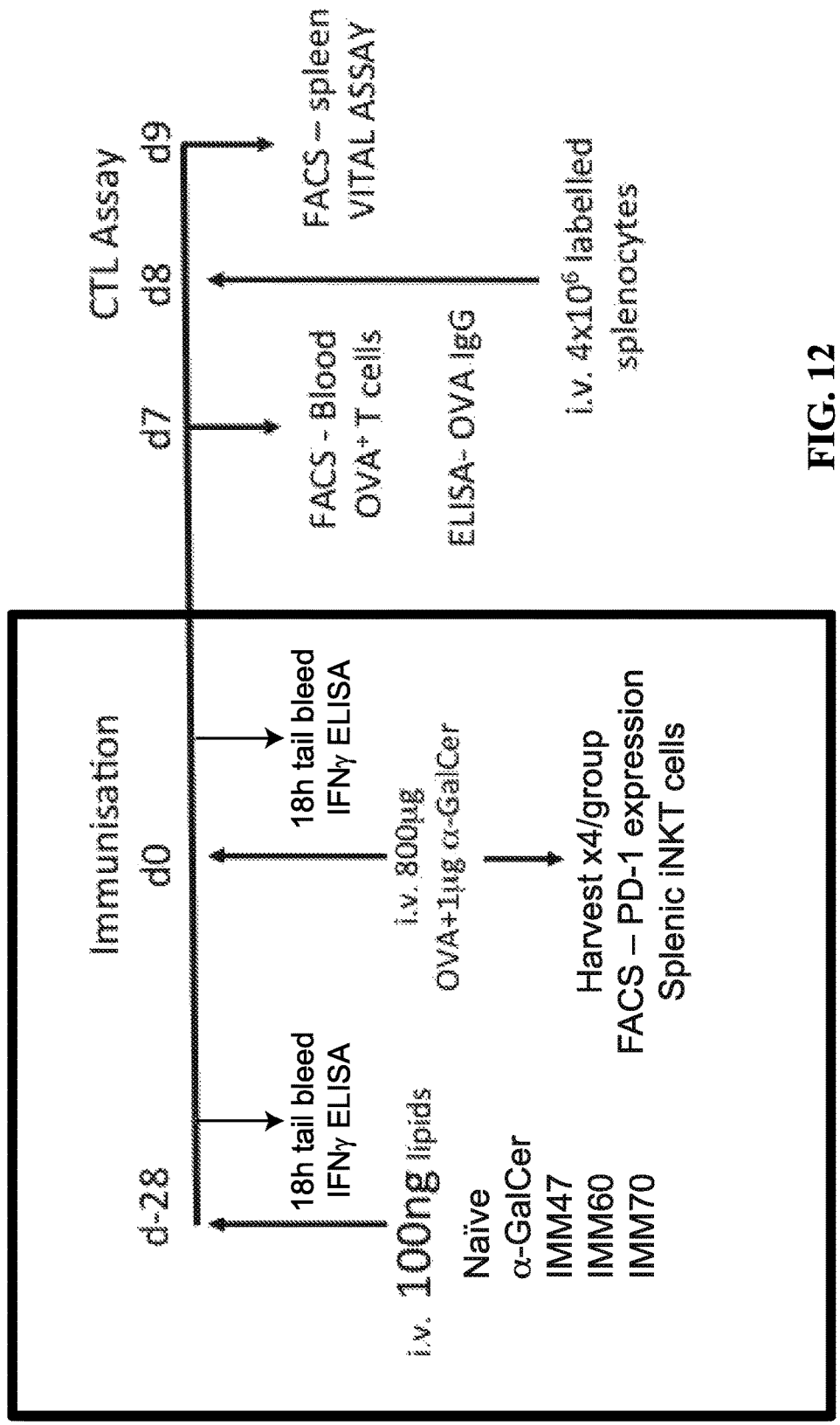
FIG. 12 is a schematic showing the experimental design for the experiments described below (Section heading: In vivo anergy of iNKT cells).
Figure 15:
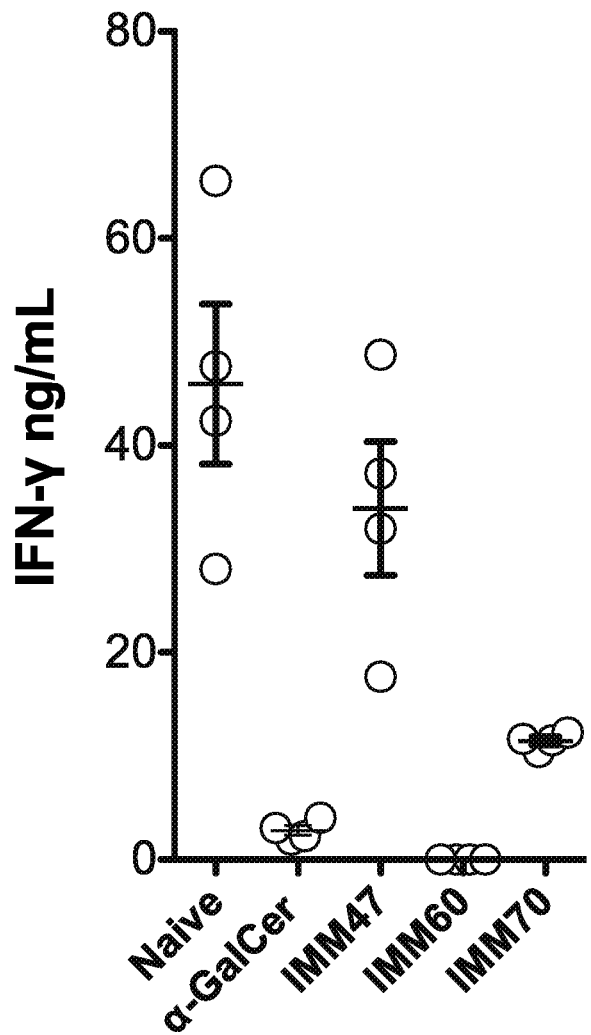
FIG. 15 is a graph showing the measurement of iNKT cell anergy (as defined by measurements of IFNγ) after stimulation with various ligands.
Figure 16:
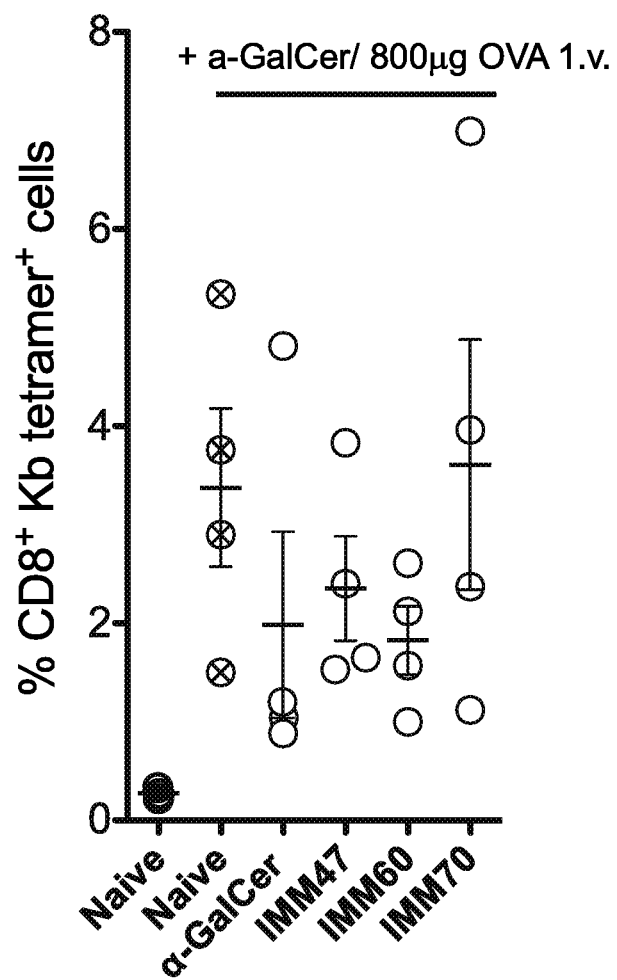
FIG. 16 is a graph showing that IMM70 preconditioned mice demonstrated the highest T-cell response.

As indicated in FIG. 12, immunization was performed at day zero with 800 µg OVA and alphaGalCer (for all mice). Eighteen hours later, iNKT cell activation was analyzed by IFNγ expression by ELISA (FIG. 15). At day 7, T cell responses were analyzed (FIG. 16).

The results in FIG. 15 confirmed previous findings that IMM47 caused the weakest iNKT cell anergy (as defined by the highest amount of IFNγ). AlphaGalCer and IMM60 induced the highest iNKT cell anergy, while IMM70 pre-conditioned mice had functional iNKT cells (as shown by the intermediate amount of IFNγ). The results shown in FIG. 16 indicate that IMM70 preconditioned mice had the highest T-cell response.

Lysis of Dendritic Cells Pulsed with IMM47, IMM60 and IMM70

The following experiments were performed to analyze the extent to which IMM47, IMM60 and IMM70 cause lysis of human dendritic cells.

Figure 17:
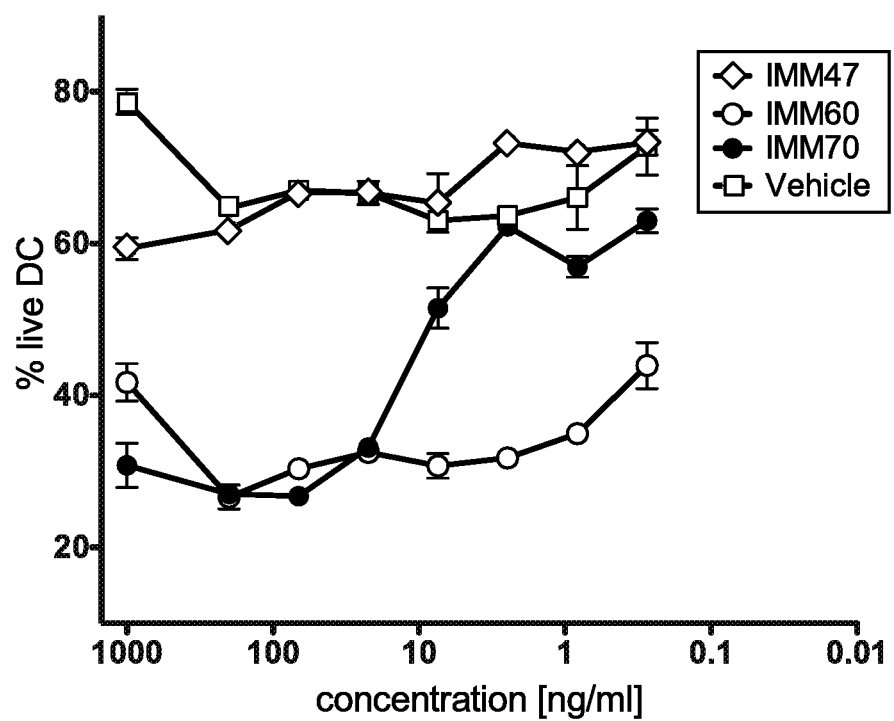
FIG. 17 is a graph showing that IMM60 caused the highest dendritic cell killing compared to the other compounds tested.

Monocyte-derived dendritic cells and human iNKT cells were cultured with various concentrations of each lipid for 40 hours and then PI stained to determine percent dendritic cell lysis (and percent survival). The results shown in FIG. 17 show that IMM47 caused the lowest dendritic cell killing (by observing the percent live dendritic cells in the sample) and that IMM60 caused the highest dendritic cell killing.

Interestingly, at concentrations lower than 5 ng/ml, the percentage of DC lysis obtained with IMM70 is very similar to the results obtained with IMM47, even though IMM70 is the stronger agonist.

Direct T- and B-Cell Priming by IMM47, IMM60 and IMM70

Figure 11:
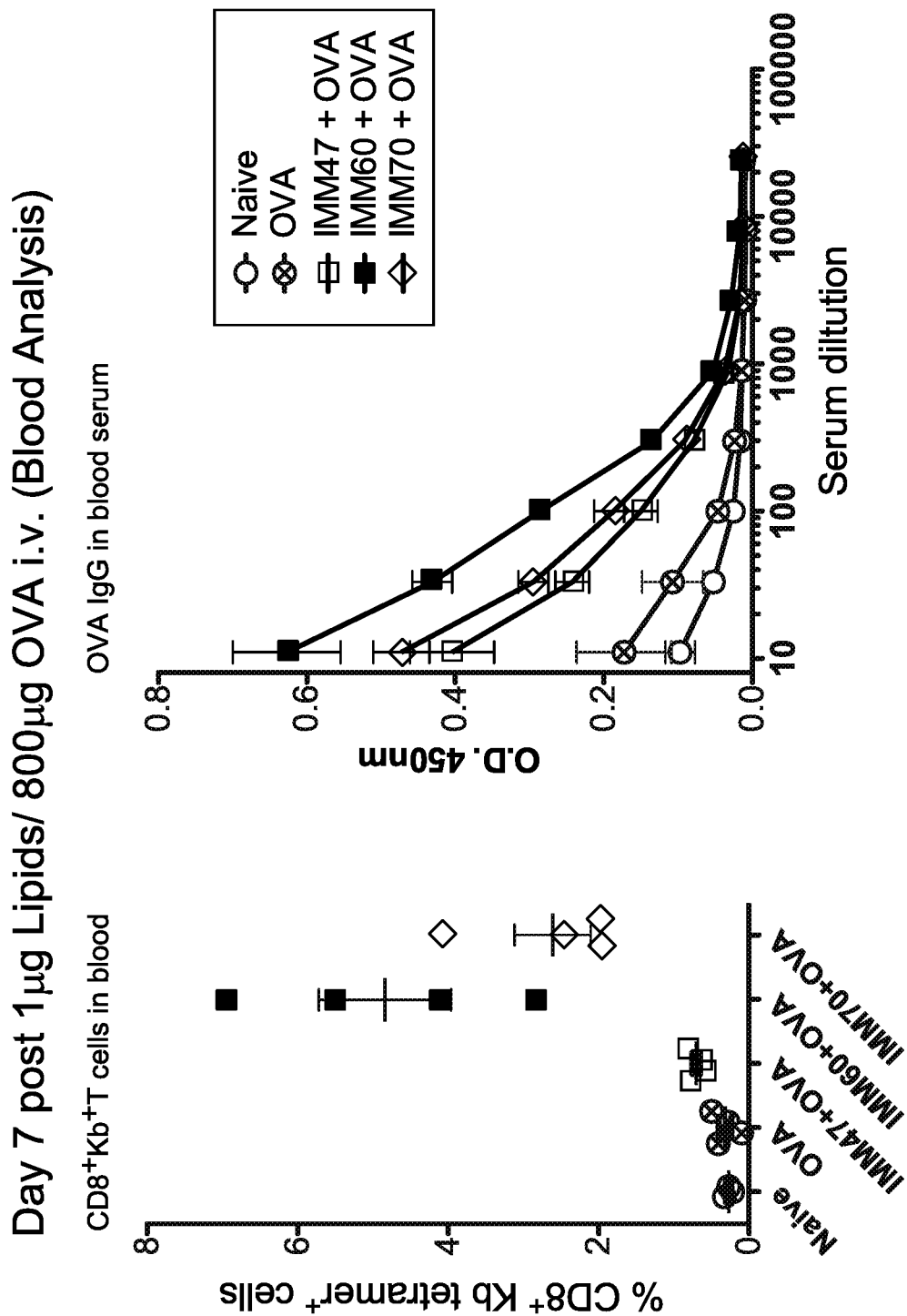
FIG. 11 contains graphs showing T cell (left panel) and B cell (right panel) responses to antigen (OVA) following exposure to various lipids. The data indicate that IMM60 induced stronger T- and B-cell responses compared to IMM47 and IMM70.
Figure 18:
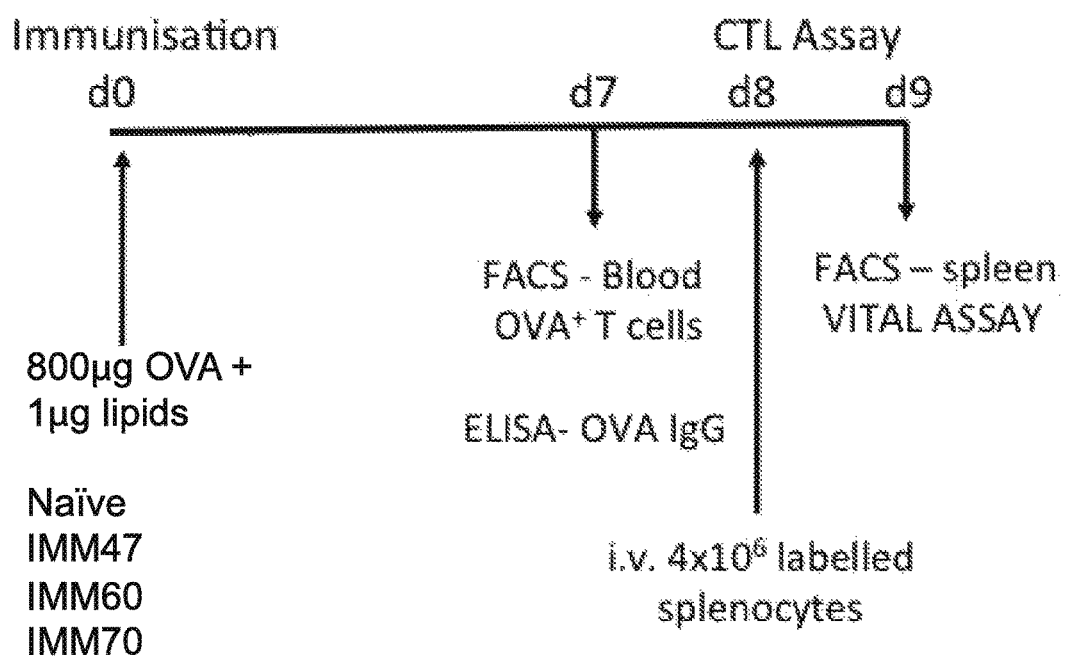
FIG. 18 is a schematic showing the design of experiments performed to analyze the ability of IMM47, IMM60 and IMM70 to induce T- and B-cell responses. (Heading below: Direct T- and B-Cell Priming by IMM47, IMM60 and IMM70.)

Experiments were performed to analyze the ability of IMM47, IMM60 and IMM70 to induce T- and B-cell responses. The experimental design is set forth in FIG. 18. Briefly, ovalbumin plus 1 microgram of one of the lipids were used to immunize mice at day zero, and blood/cells were drawn and analyzed at the indicated times. The data provided in FIG. 11 show that IMM60 induced stronger T- and B-cell responses compared to IMM47 and IMM70, as measured by CD8+ Kb tetramer+ cells and serum OVA IgG levels.

Some Specific Embodiments of the Disclosure:

1. A compound having a structure (I):

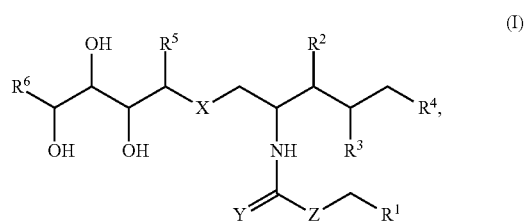

wherein $R^1$ is $C_5$-$C_{25}$ alkyl, $C_5$-$C_{25}$ alkenyl, $C_5$-$C_{25}$ alkynyl, $C_5$-$C_{25}$ heteroalkyl, $C_5$-$C_{25}$ heteroalkenyl, or $C_5$-$C_{25}$ heteroalkynyl;

$R^2$ and $R^3$ are each independently selected from H, OH, SH, amino or substituted amino;

$R^4$ is $C_5$-$C_{20}$ alkyl, $C_5$-$C_{20}$ alkenyl, $C_5$-$C_{20}$ alkynyl, $C_5$-$C_{20}$ heteroalkyl, $C_5$-$C_{20}$ heteroalkenyl, or $C_5$-$C_{20}$ heteroalkynyl;

$R^6$ and $R^5$ are each independently selected from H, alkyl, and alkenyl, or $R^6$ and $R^5$ together form a 6-, 7-, or 8-membered cycloalkyl or cycloalkenyl ring;

X is O, S, $SO_2$, SO(NH), SO(N(alkyl)), NH, N(alkyl), or $CH_2$;

Y is O, NH, N(alkyl), or S;

Z is O, S, NH, N(alkyl), or $CH_2$;

with the proviso that when Y and X are each O and $R^5$ and $R^6$ are each H, Z is not $CH_2$; and when Y is O, $R^6$ and $R^5$ together form a 6-membered cycloalkyl ring, and Z is $CH_2$, the cycloalkyl ring is not substituted with —$CH_2OH$, —OH, —$CH_3$, or —$CH_2OCH_3$, or a salt, ester, solvate, or hydrate thereof.

2. The compound, salt, ester, solvate, or hydrate of paragraph 1 having a structure (IA), (IB), (IC), or (ID):

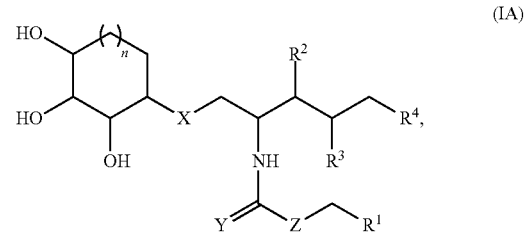

-continued

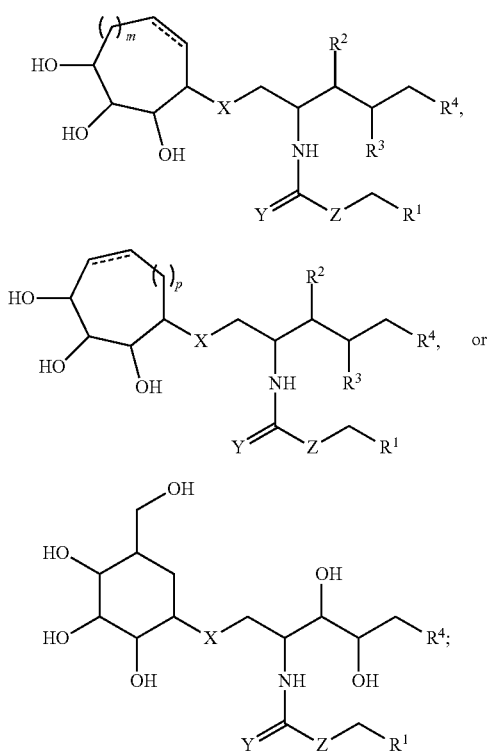

wherein
n is 1, 2, or 3;
m is 0, 1, or 2;
p is 1 or 2; and
the dashed line is an optional double bond.

3. The compound, salt, ester, solvate, or hydrate of paragraph 1, wherein $R^6$ is H.

4. The compound, salt, ester, solvate, or hydrate of paragraph 1, wherein $R^6$ is alkyl.

5. The compound, salt, ester, solvate, or hydrate of paragraph 1, wherein $R^6$ is alkenyl.

6. The compound, salt, ester, solvate, or hydrate of any one of paragraphs 1 and 3 to 5, wherein $R^5$ is H.

7. The compound, salt, ester, solvate, or hydrate of any one of paragraphs 1 and 3 to 5, wherein $R^5$ is alkyl.

8. The compound, salt, ester, solvate, or hydrate of any one of paragraphs 1 and 3 to 5, wherein $R^5$ is alkenyl.

9. The compound, salt, ester, solvate, or hydrate of any one of paragraphs 1 to 8, wherein Z is $CH_2$.

10. The compound, salt, ester, solvate, or hydrate of any one of paragraphs 1 to 8, wherein Z is O.

11. The compound, salt, ester, solvate, or hydrate of any one of paragraphs 1 to 8, wherein Z is S.

12. The compound, salt, ester, solvate, or hydrate of any one of paragraphs 1 to 8, wherein Z is NH.

13. The compound, salt, ester, solvate, or hydrate of any one of paragraphs 1 to 8, wherein Z is N(alkyl).

14. The compound, salt, ester, solvate, or hydrate of any one of paragraphs 1 to 8, wherein Z is $CH_2$.

15. The compound, salt, ester, solvate, or hydrate of any one of paragraphs 1 to 14, wherein X is O.

16. The compound, salt, ester, solvate, or hydrate of any one of paragraphs 1 to 14, wherein X is S.

17. The compound, salt, ester, solvate, or hydrate of any one of paragraphs 1 to 14, wherein X is $SO_2$.

18. The compound, salt, ester, solvate, or hydrate of any one of paragraphs 1 to 14, wherein X is SO(NH).

19. The compound, salt, ester, solvate, or hydrate of any one of paragraphs 1 to 14, wherein X is SO(N(alkyl)).

20. The compound, salt, ester, solvate, or hydrate of any one of paragraphs 1 to 14, wherein X is NH.

21. The compound, salt, ester, solvate, or hydrate of any one of paragraphs 1 to 14, wherein X is N(alkyl).

22. The compound, salt, ester, solvate, or hydrate of any one of paragraphs 1 to 14, wherein X is $CH_2$.

23. The compound, salt, ester, solvate, or hydrate of any one of paragraphs 1 to 22, wherein Y is O.

24. The compound, salt, ester, solvate, or hydrate of any one of paragraphs 1 to 22, wherein Y is NH.

25. The compound, salt, ester, solvate, or hydrate of any one of paragraphs 1 to 22, wherein Y is N(alkyl).

26. The compound, salt, ester, solvate, or hydrate of any one of paragraphs 1 to 22, wherein Y is S.

27. The compound, salt, ester, solvate, or hydrate of any one of paragraphs 1 to 26, wherein $R^2$ is H.

28. The compound, salt, ester, solvate, or hydrate of any one of paragraphs 1 to 26, wherein $R^2$ is SH.

29. The compound, salt, ester, solvate, or hydrate of any one of paragraphs 1 to 26, wherein $R^2$ is amino or substituted amino.

30. The compound, salt, ester, solvate, or hydrate of any one of paragraphs 1 to 26, wherein $R^2$ is OH.

31. The compound, salt, ester, solvate, or hydrate of any one of paragraphs 1 to 30, wherein $R^3$ is H.

32. The compound, salt, ester, solvate, or hydrate of any one of paragraphs 1 to 30, wherein $R^3$ is SH.

33. The compound, salt, ester, solvate, or hydrate of any one of paragraphs 1 to 30, wherein $R^3$ is amino or substituted amino.

34. The compound, salt, ester, solvate, or hydrate of any one of paragraphs 1 to 30, wherein $R^3$ is OH.

35. The compound, salt, ester, solvate, or hydrate of any one of paragraphs 1 to 34, wherein at least one of $R^2$ and $R^3$ is OH.

36. The compound, salt, ester, solvate, or hydrate of paragraph 35, wherein $R^2$ and $R^3$ are each OH.

37. The compound, salt, ester, solvate, or hydrate of any one of paragraphs 1 to 36, wherein $R^1$ is $C_{15}$-$C_{25}$ alkyl.

38. The compound, salt, ester, solvate, or hydrate of paragraph 37, wherein $R^1$ is $C_{23}$alkyl or $C_{24}$alkyl.

39. The compound, salt, ester, solvate, or hydrate of any one of paragraphs 1 to 36, wherein $R^1$ is $C_{15}$-$C_{25}$ heteroalkyl.

40. The compound, salt, ester, solvate, or hydrate of any one of paragraphs 1 to 36, wherein $R^1$ is $C_{15}$-$C_{25}$ alkenyl.

41. The compound, salt, ester, solvate, or hydrate of paragraph 40, wherein $R^1$ is $C_{23}$alkenyl or $C_{24}$alkenyl.

42. The compound, salt, ester, solvate, or hydrate of any one of paragraphs 1 to 36, wherein $R^1$ is $C_{15}$-$C_{25}$ heteroalkenyl.

43. The compound, salt, ester, solvate, or hydrate of any one of paragraphs 1 to 36, wherein $R^1$ is $C_{15}$-$C_{25}$ alkynyl.

44. The compound, salt, ester, solvate, or hydrate of paragraph 43, wherein $R^1$ is $C_{23}$alkynyl or $C_{24}$alkynyl.

45. The compound, salt, ester, solvate, or hydrate of any one of paragraphs 1 to 36, wherein $R^1$ is $C_{15}$-$C_{25}$ heteroalkynyl.

46. The compound, salt, ester, solvate, or hydrate of any one of paragraphs 1 to 45, wherein $R^4$ is $C_{10}$-$C_{20}$ alkyl.

47. The compound, salt, ester, solvate, or hydrate of paragraph 46, wherein $R^4$ is $C_{13}$alkyl.

48. The compound, salt, ester, solvate, or hydrate of any one of paragraphs 1 to 45, wherein $R^4$ is $C_{10}$-$C_{20}$ heteroalkyl.

49. The compound, salt, ester, solvate, or hydrate of any one of paragraphs 1 to 45, wherein $R^4$ is $C_{10}$-$C_{20}$ alkenyl.

50. The compound, salt, ester, solvate, or hydrate of paragraph 49, wherein $R^4$ is $C_{13}$ alkenyl.

51. The compound, salt, ester, solvate, or hydrate of any one of paragraphs 1 to 45, wherein $R^4$ is $C_{10}$-$C_{20}$ heteroalkenyl.

52. The compound, salt, ester, solvate, or hydrate of any one of paragraphs 1 to 45, wherein $R^4$ is $C_{10}$-$C_{20}$ alkynyl.

53. The compound, salt, ester, solvate, or hydrate of paragraph 52, wherein $R^4$ is $C_{13}$ alkynyl.

54. The compound, salt, ester, solvate, or hydrate of any one of paragraphs 1 to 45, wherein $R^4$ is $C_{10}$-$C_{20}$ heteroalkynyl.

55. The compound, salt, ester, solvate, or hydrate of paragraph 1 having a structure selected from the group consisting of:

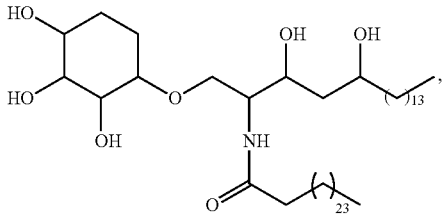

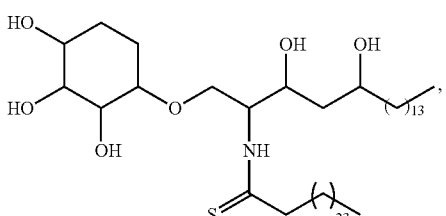

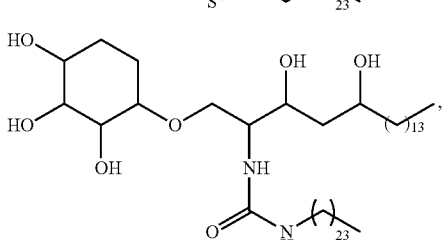

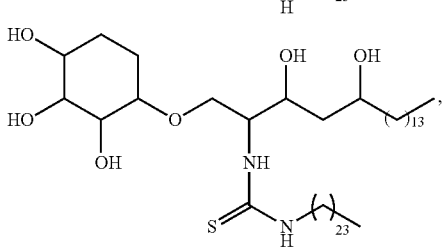

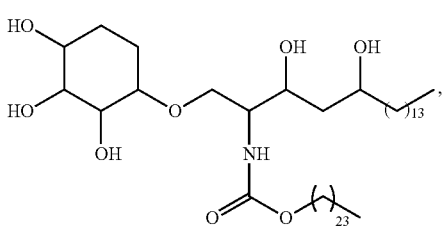

-continued

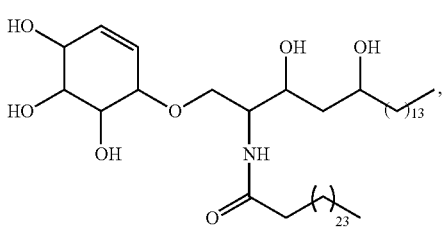

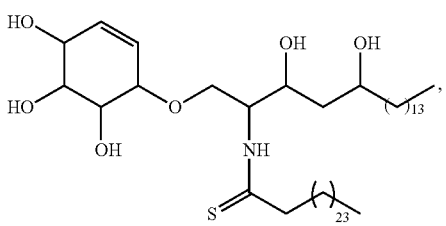

85
-continued
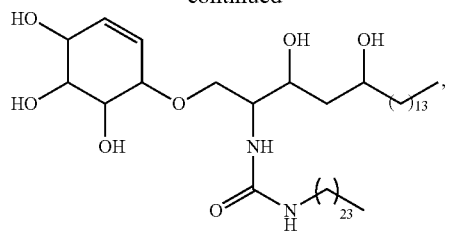
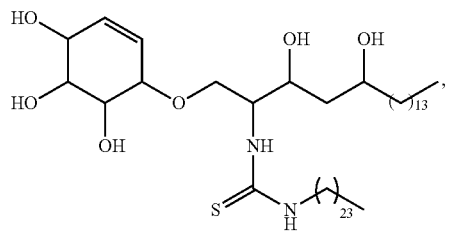
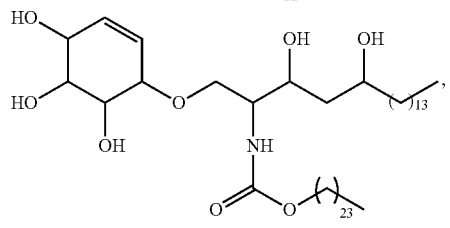
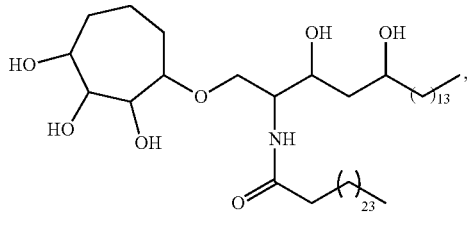
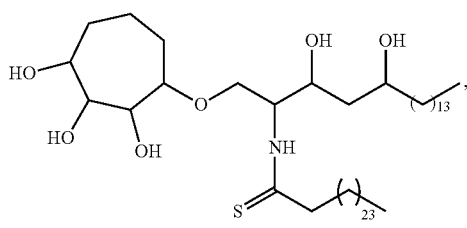
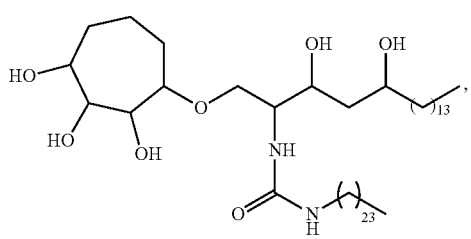
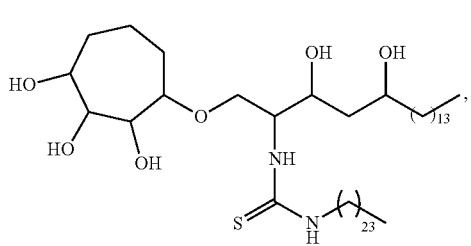
86
-continued
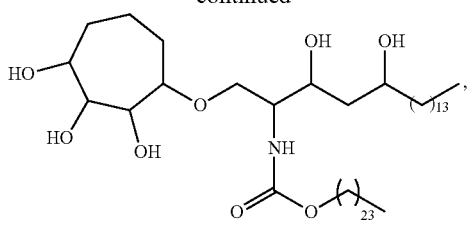
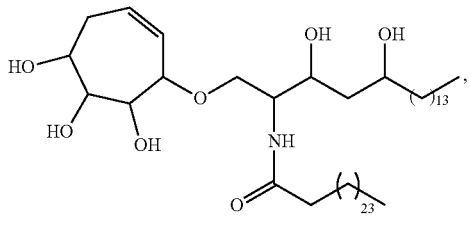
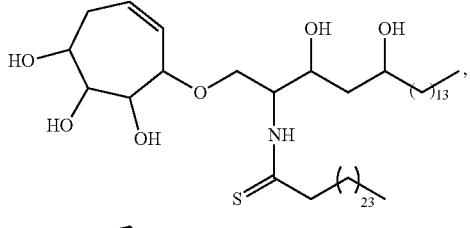
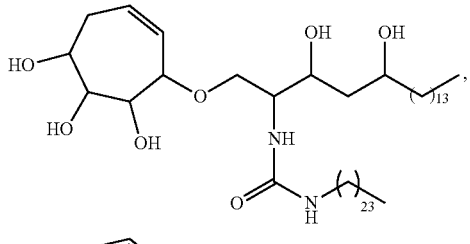
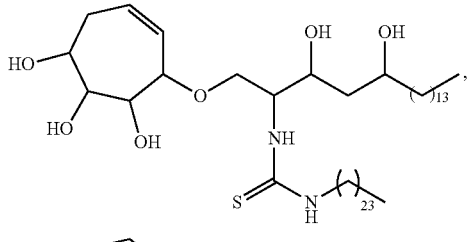
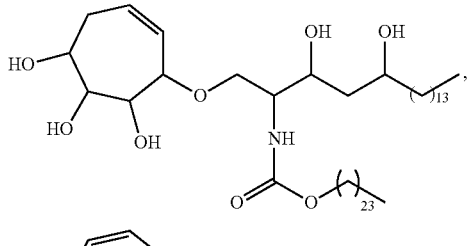
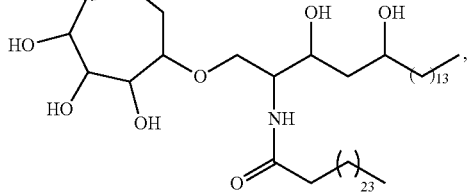

| 87 -continued | 88 -continued |
|---|---|
| 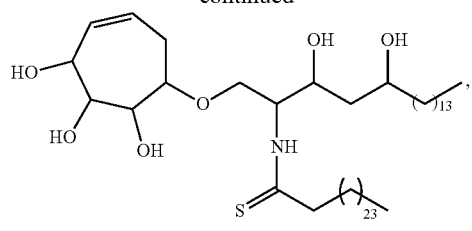 | 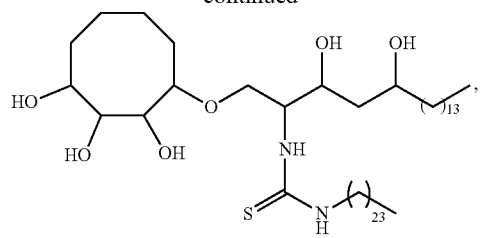 |
| | 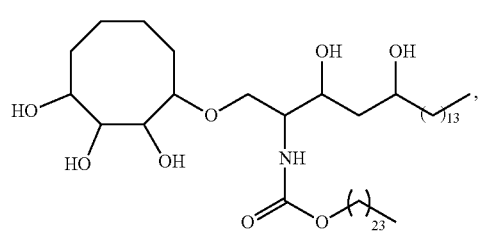 |
| | 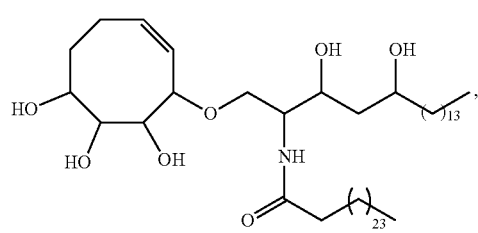 |
| | 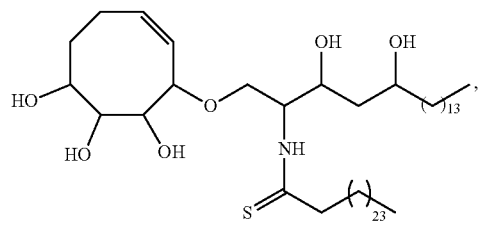 |
| | 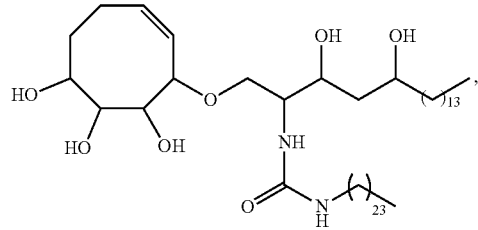 |
| | 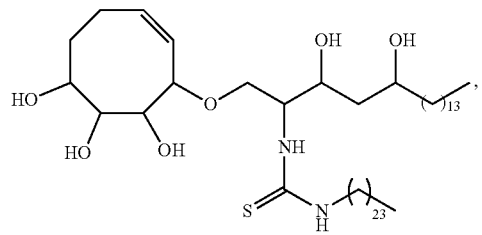 |
| | 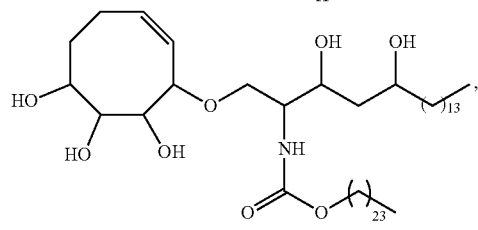 |

89
-continued
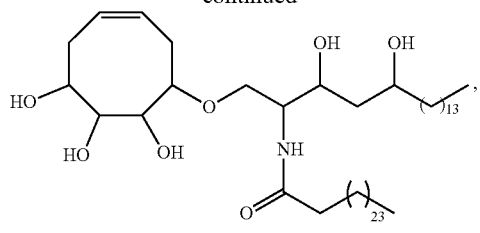
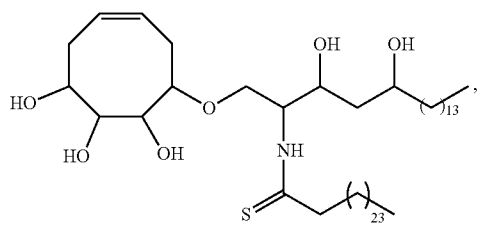
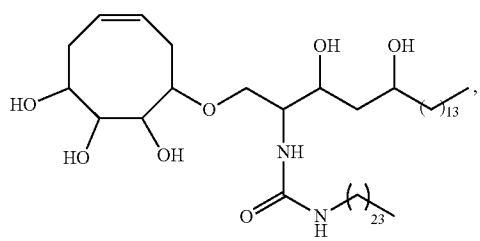
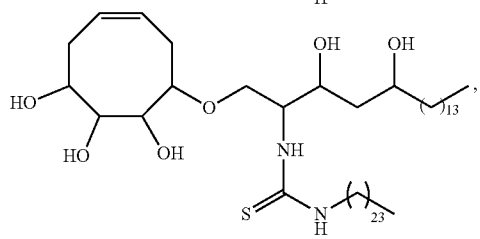
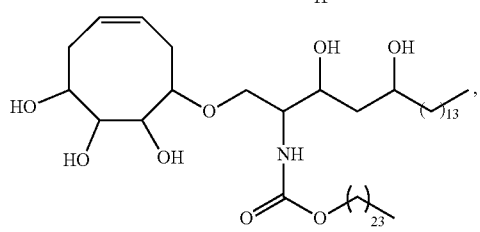
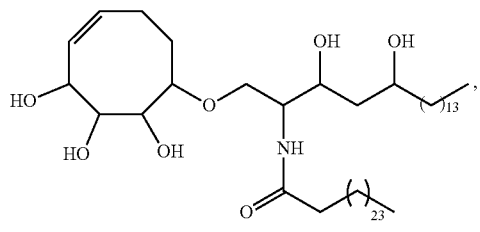
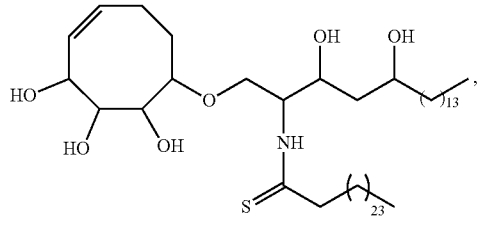
90
-continued
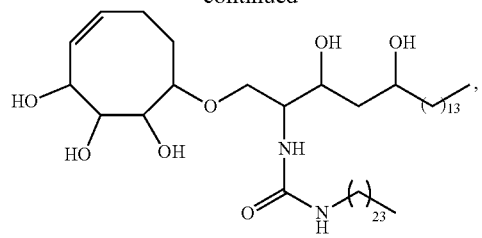
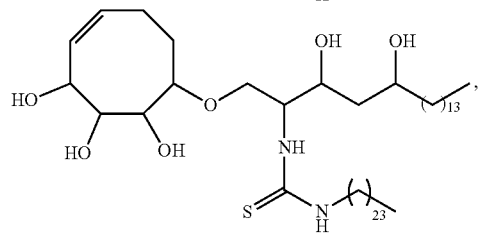
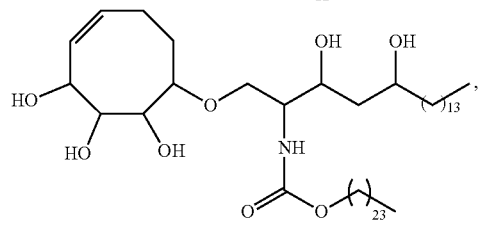
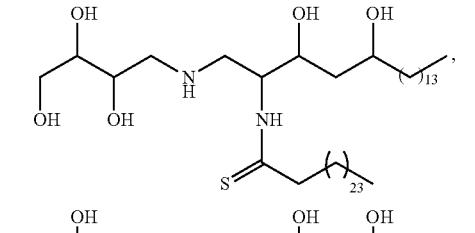
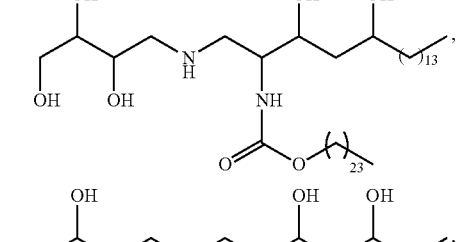
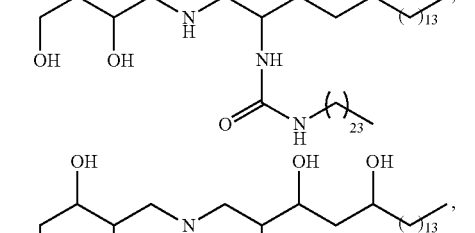
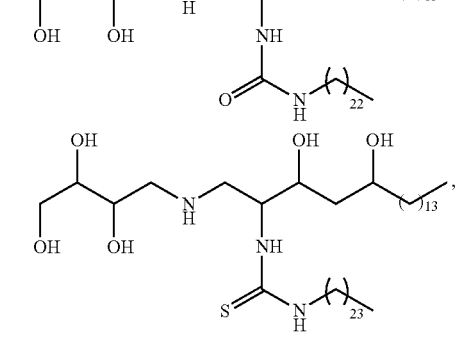

91
-continued
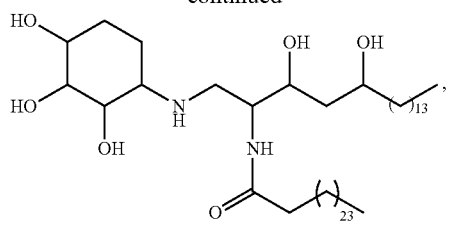
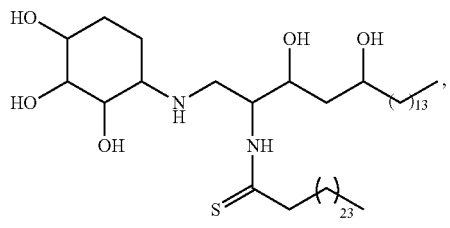
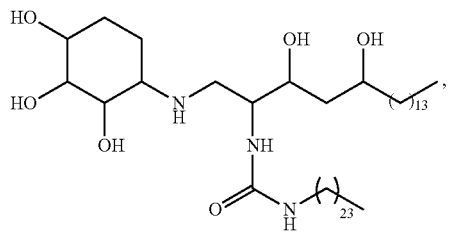
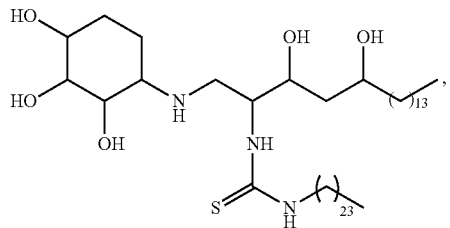
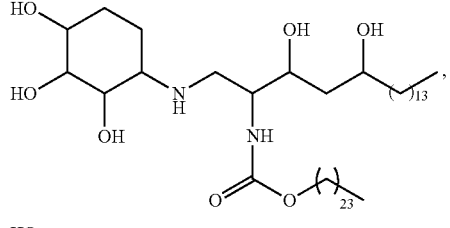
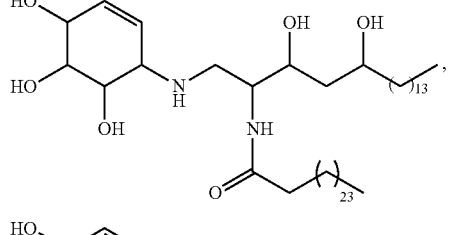
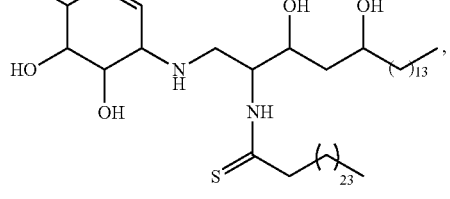
92
-continued
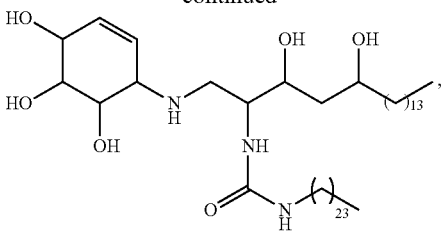
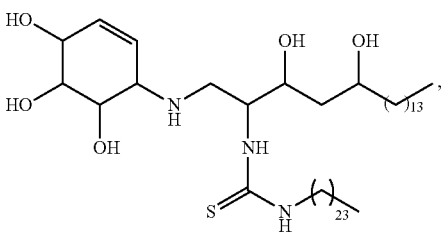
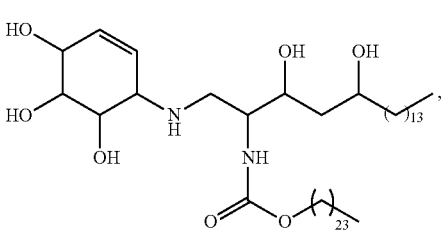
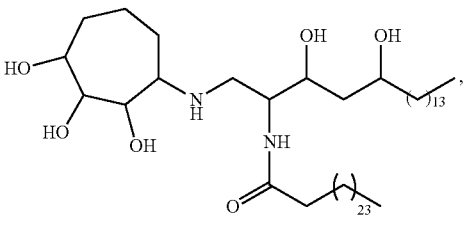
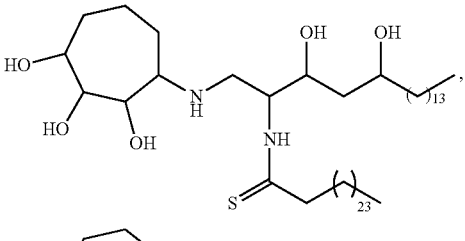
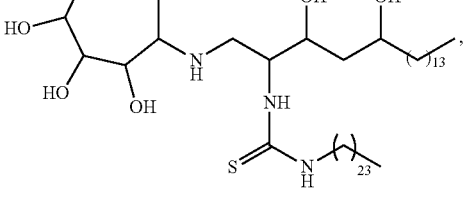

93
-continued
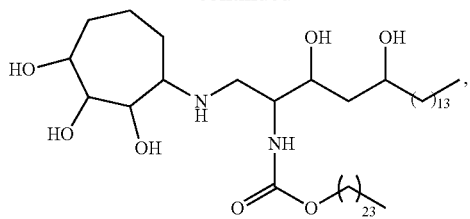
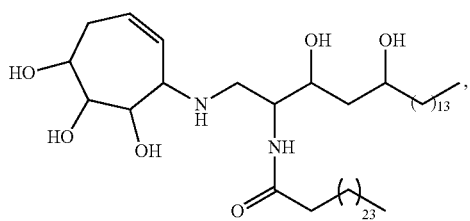
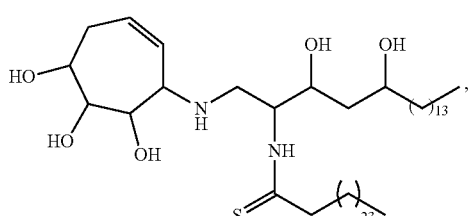
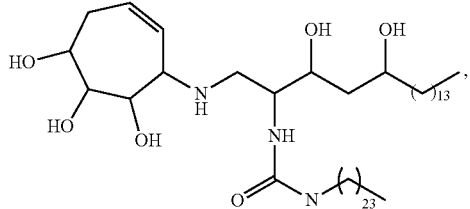
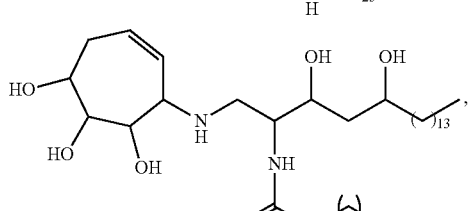
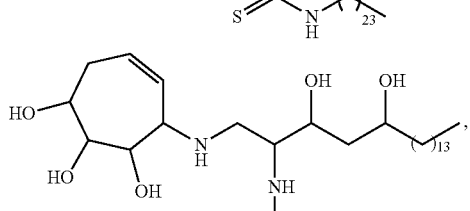
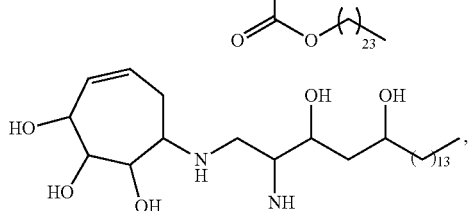
94
-continued
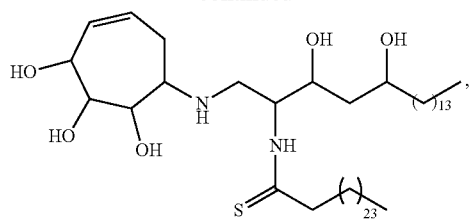
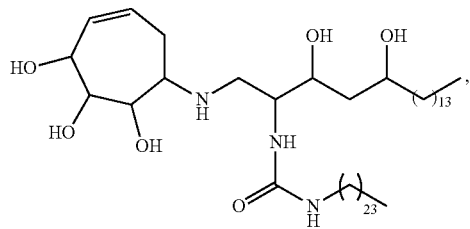
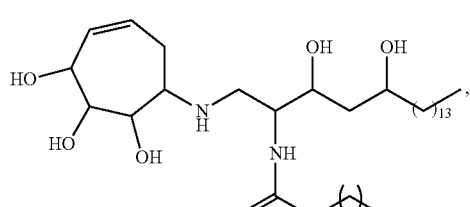
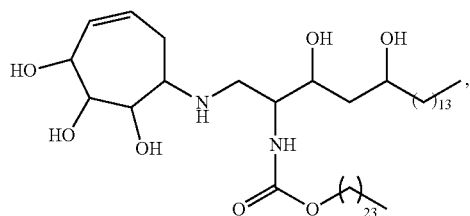
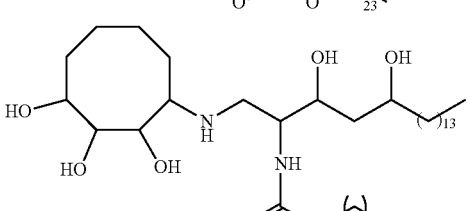
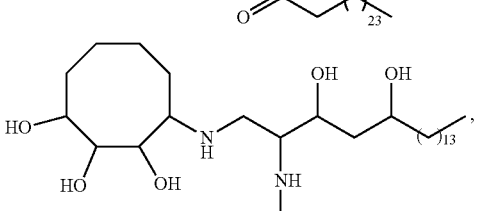
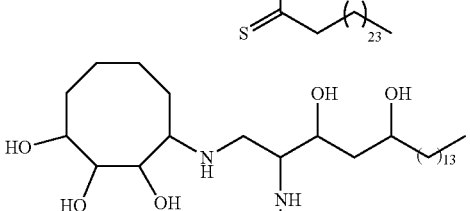

95 -continued

96 -continued

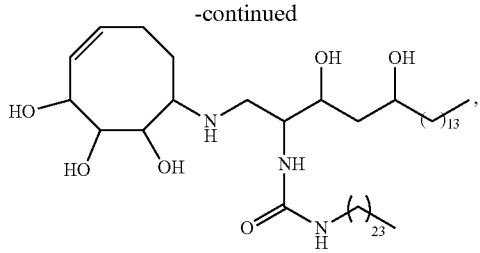
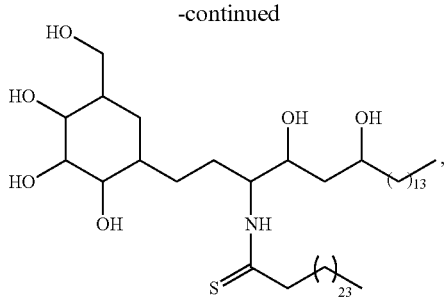
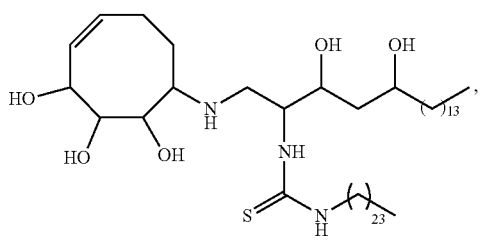
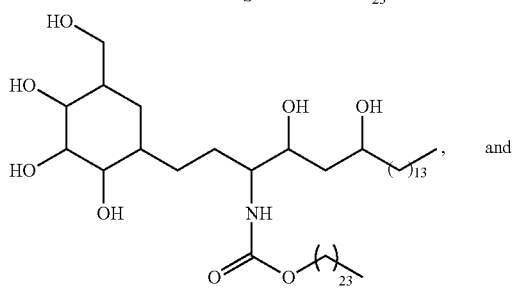
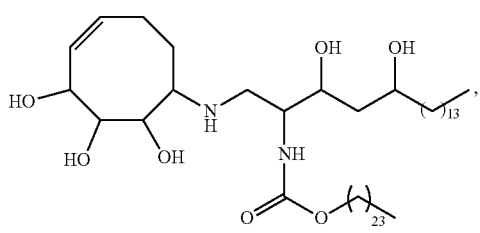
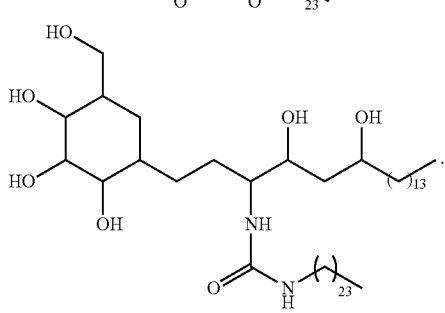
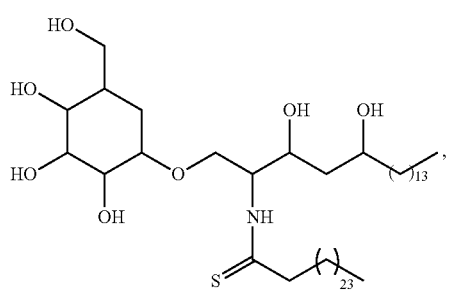
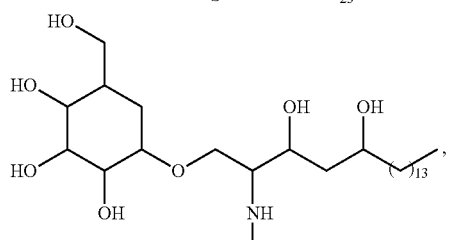
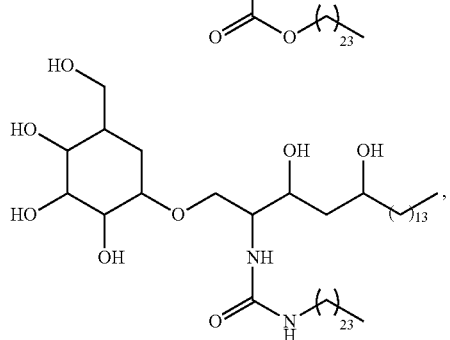

56. The compound, salt, ester, solvate, or hydrate of any one of paragraphs 1 to 55, having a structure of (IE):

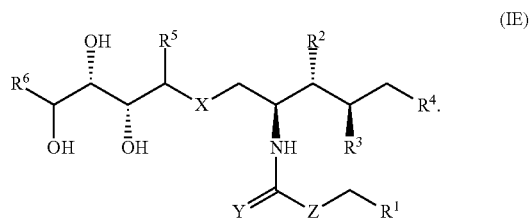

(IE)

57. The compound, salt, ester, solvate, or hydrate of any one of paragraphs 1 to 56 that is purified and isolated.

58. A composition comprising the compound, salt, ester, solvate, or hydrate of any one of paragraphs 1 to 57 and a pharmaceutically acceptable excipient.

59. A method of activating an NKT cell comprising contacting the cell with the compound, salt, ester, solvate, or hydrate of any one of paragraphs 1 to 57 or the composition of paragraph 58 in an amount effective to activate the NKT cell.

60. The method of paragraph 59, wherein activating the NKT cell comprises one or more of inducing secretion of a cytokine from the NKT cell, stimulating proliferation of the NKT cell, and upregulating expression of a cell surface marker on the NKT cell.

61. The method of paragraph 60, wherein the activating comprises inducing secretion of a cytokine and the cytokine is one or more of IL-1, IL-2, IL-4, IL-5, IL-6, IL-10, IL-13, IL-15, TNF-α, TNF-β, and IFN-γ.

62. The method of paragraph 60, wherein the activating comprises upregulating at least one cell surface marker selected from CD69, CD25, an IL-12 receptor and CD40L.

63. The method of any one of paragraph 59 to 62, wherein the contacting comprises administering the compound, salt, ester, solvate, or hydrate of any one of paragraphs 1 to 57 to a subject in need of NKT cell activation.

64. The method of paragraph 63, wherein the subject suffers from cancer.

65. The method of paragraph 64, wherein the subject suffer from a cancer selected from basal cell carcinoma, breast cancer, leukemia, Burkitt's Lymphoma, colon cancer, esophageal cancer, bladder cancer, gastric cancer, head and neck cancer, hepatocellular cancer, Hodgkin's Lymphoma, hairy cell leukemia, Wilms' Tumor, thyroid cancer, thymoma, thymic carcinoma, testicular cancer, T-cell lymphoma, prostate cancer, non-small cell lung cancer, liver cancer, renal cell cancer, and melanoma.

66. The method of any one of paragraphs 63 to 65, further comprising administering a second therapeutic to the subject.

67. The method of paragraph 66, wherein the second therapeutic is a chemotherapeutic or an immunotherapeutic agent.

68. The method of paragraph 67, wherein the immunotherapeutic is a cancer vaccine.

69. The method of paragraph 67, wherein the immunotherapeutic is a cancer antigen.

70. The method of paragraph 69, wherein the cancer antigen is selected from MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (AGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1, CT-7, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RARα fusion protein, PTPRK, K-ras, N-ras, Triosephosphate isomeras, GnTV, Herv-K-mel, Lage-1, Mage-C2, NA-88, /Lage-2, SP17, and TRP2-Int2, (MART-I), gp100 (Pmel 17), TRP-1, TRP-2, MAGE-1, MAGE-3, p15(58), CEA, NY-ESO (LAGE), SCP-1, Hom/Mel-40, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, .beta.-Catenin, CDK4, Mum-1, p16, TAGE, PSMA, PSCA, CT7, telomerase, 43-9F, 5T4, 791Tgp72, α-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (Ep-CAM), HTgp-175, M344, MA-50, MG7-Ag, MOV18, NB\170K, NY-CO-1, RCAS1, SDCCAG16, TA-90 (Mac-2 binding protein\cyclophilin C-associated protein), TAAL6, TAG72, TLP, and TPS.

71. The method of paragraph 67, wherein the immunotherapeutic is a polynucleotide encoding a cancer antigen.

72. The method of paragraph 71, wherein the polynucleotide is in a vector.

73. The method of paragraph 66, wherein the second therapeutic is selected from aspirin, sulindac, curcumin, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; non-steroidal antiandrogens such as flutamide; kinase inhibitors, histone deacetylase inhibitors, methylation inhibitors, proteasome inhibitors, monoclonal antibodies, oxidants, anti-oxidants, telomerase inhibitors, BH3 mimetics, ubiquitin ligase inhibitors, stat inhibitors, herceptin, alemtuzumab, gemtuzumab, rituximab, ibritumomab tiuxetan, imatinib, erlotinib, cyclophosphamide, infliximab, adalimmumab, basiliximab, anti CD40/CD40L antibody, anti-CTLA-4 blocking antibody, soluble LAG3 based immune modulator, MPL, CpG, single-stranded RNA, nucleotides, nucleotide analogue, CL087, loxoribine, polyinosine-polycytidylic acid, flagellin, resiquimod, immiquimod, gardiquimod, NOD ligands, muramyl dipeptide, murabutide, peptidoglycan, muramyldipeptide, oseltamivir phosphate, Amphotericin B, and palivizumab.

74. The method of any one of paragraphs 66 to 73, wherein the second therapeutic and the compound, salt, ester, solvate, or hydrate is administered simultaneously.

75. The method of paragraph 74, wherein the second therapeutic and the compound, salt, ester, solvate, or hydrate are co-formulated.

76. The method of any one of paragraphs 66 to 73, wherein the second therapeutic and the compound, salt, ester, solvate, or hydrate are administered sequentially.

77. The method of paragraph 76, wherein the second therapeutic is administered before the compound, salt, ester, solvate, or hydrate.

78. The method of paragraph 76, wherein the second therapeutic is administered after the compound, salt, ester, solvate, or hydrate.

79. A method of treating a subject suffering from cancer comprising administering to the subject a compound, salt, ester, solvate or hydrate of any one of paragraphs 1 to 57 in an amount effective to treat the cancer.

80. The method of paragraph 79, wherein the subject is human.

81. The method of paragraph 79 or 80, wherein the cancer is selected from basal cell carcinoma, breast cancer, leukemia, Burkitt's Lymphoma, colon cancer, esophageal cancer, bladder cancer, gastric cancer, head and neck cancer, hepatocellular cancer, Hodgkin's Lymphoma, hairy cell leukemia, Wilms' Tumor, thyroid cancer, thymoma, thymic carcinoma, testicular cancer, T-cell lymphoma, prostate cancer, non-small cell lung cancer, liver cancer, renal cell cancer, and melanoma.

82. The compound, salt, ester, solvate or hydrate of any one of paragraphs 1 to 57 for treating cancer.

83. Use of the compound, salt, ester, solvate or hydrate of any one of paragraphs 1 to 57 in the manufacture of a medicament for treating cancer.

What is claimed is:
1. A composition comprising:
a compound having a structure:

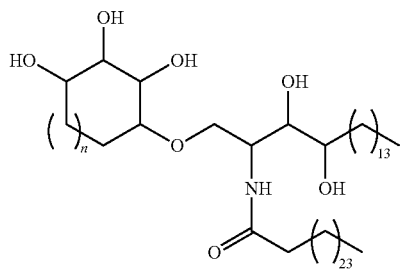

wherein n is 1, 2, or 3;
or a salt, ester, solvate, or hydrate thereof; and
a therapeutic selected from the group consisting of a chemotherapeutic agent, a biological response modifying agent, and an immunotherapeutic agent.

2. The composition of claim 1, wherein the compound has a structure:

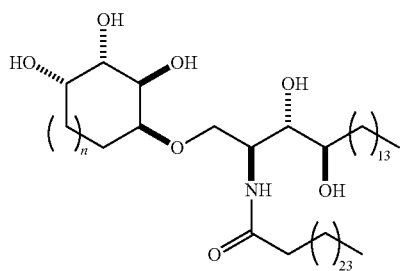

wherein n is 1, 2, or 3;
or a salt, ester, solvate, or hydrate thereof.

3. The composition of claim 2, wherein n is 1, and wherein the composition further comprises a pharmaceutically acceptable carrier.

4. The composition of claim 3, wherein the therapeutic comprises an immunotherapeutic that comprises a cancer vaccine, a cancer antigen, or a polynucleotide that comprises a nucleotide sequence that encodes a cancer antigen.

5. The composition of claim 4, wherein the therapeutic comprises a cancer antigen that comprises at least one member selected from one or more of (a) MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (AGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1, CT-7, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RARa fusion protein, PTPRK, K-ras, N-ras, Triosephosphate isomerase, GnTV, Herv-K-mel, Lage-1, NA-88, /Lage-2, SP17, and TRP2-Int2, (MART-1), gplOO (Pmel 17), TRP-1, TRP-2, MAGE-1, MAGE-3, pl5(58), CEA, NY-ESO (LAGE), SCP-1, Hom/Mel-40, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, pl85erbB2, p180erbB-3, c-met, nm-23H1, PSA, TAG-72-4, CA 19-9, CA 72-4, CAM 17.1, NuMa, K-ras, CDK4, Mum-1, p16, TAGE, PSMA, PSCA, CT7, telomerase, 43-9F, 5T4, 791Tgp72, a-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (Ep-CAM), HTgp-175, M344, MA-50, MG7-Ag, MOV18, NBM70K, NY-CO-1, RCAS1, SDCCAG16, TA-90 (Mac-2 binding protein\cyclophilin C-associated protein), TAAL6, TAG72, TLP, and TPS; and (b) immunogenic fragments that comprise an epitope of any of the foregoing antigens.

6. A method of activating a natural killer T (NKT) cell comprising contacting the cell with the composition of claim 1 in an amount effective to activate the NKT cell.

7. The method of claim 6, wherein the contacting comprises administering the composition to a subject in need of NKT cell activation.

8. The method of claim 7, wherein the subject suffers from cancer,
wherein the cancer is selected from the group consisting of basal cell carcinoma, breast cancer, leukemia, Burkitt's Lymphoma, colon cancer, esophageal cancer, bladder cancer, gastric cancer, head and neck cancer, hepatocellular cancer, Hodgkin's Lymphoma, hairy cell leukemia, Wilms' Tumor, thyroid cancer, thymoma, thymic carcinoma, testicular cancer, T-cell lymphoma, prostate cancer, non-small cell lung cancer, liver cancer, renal cell cancer and melanoma.

9. A method of treatment comprising administering, to a subject with cancer,
(a) a first composition that comprises a compound that has a structure:

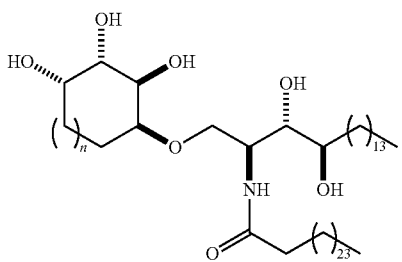

wherein n is 1, 2, or 3;
or a salt, ester, solvate, or hydrate thereof; and
(b) a second composition that comprises a therapeutic selected from the group consisting of a chemotherapeutic agent, a biological response modifying agent, and an immunotherapeutic agent,
wherein the cancer is selected from the group consisting of basal cell carcinoma, breast cancer, leukemia, Burkitt's Lymphoma, colon cancer, esophageal cancer, bladder cancer, gastric cancer, head and neck cancer, hepatocellular cancer, Hodgkin's Lymphoma, hairy cell leukemia, Wilms' Tumor, thyroid cancer, thymoma, thymic carcinoma, testicular cancer, T-cell lymphoma, prostate cancer, non-small cell lung cancer, liver cancer, renal cell cancer and melanoma.

10. The method of claim 9, wherein the therapeutic comprises an immunotherapeutic that comprises a cancer vaccine, a cancer antigen, or a polynucleotide comprising a nucleotide sequence that encodes a cancer antigen.

11. The method of claim 9, wherein the therapeutic comprises a cancer antigen that comprises at least one member selected from one or more of (a) MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (AGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1, CT-7, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RARa fusion protein, PTPRK, K-ras, N-ras, Triosephosphate isomerase, GnTV, Herv-K-mel, Lage-1, NA-88, /Lage-2, SP17, and TRP2-Int2, (MART-1), gplOO (Pmel 17), TRP-1, TRP-2, MAGE-1, MAGE-3, p15(58), CEA, NY-ESO (LAGE), SCP-1, Hom/Mel-40, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, CDK4, Mum-1, p16, TAGE, PSMA, PSCA, CT7, telomerase, 43-9F, 5T4, 791Tgp72, a-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NBM70K, NY-CO-1, RCAS1, SDCCAG16, TA-90 (Mac-2 binding protein\cyclophilin C-associated protein), TAAL6, TAG72, TLP, and TPS; and (b) immunogenic fragments that comprise an epitope of any of the foregoing antigens.

12. The method of claim 9, further comprising administering an immunotherapeutic agent that comprises at least one antibody selected from the group consisting of an anti-Her2/neu receptor antibody, an anti-CD52 antibody, an anti-CD33 antibody, an anti-CD20 antibody, an anti-TNFa antibody, an anti-CD25 IL-2 receptor antibody, an anti-CD40/CD40L antibody, an anti-CTLA-4 antibody, an anti-PD-1 (anti-CD279) antibody, an anti-PDL-1 antibody, an anti-GITR antibody, and an anti-OX-40 (anti-CD 134) antibody, wherein the antibody is a monoclonal antibody, a humanized antibody, a human antibody or a chimeric antibody.

13. The method of claim 8, further comprising administering to the subject an immunotherapeutic agent that comprises at least one antibody selected from the group consisting of an anti-Her2/neu receptor antibody, an anti-CD52 antibody, an anti-CD33 antibody, an anti-CD20 antibody, an anti-TNFa antibody, an anti-CD25 IL-2 receptor antibody, an anti-CD40/CD40L antibody, an anti-CTLA-4 antibody, an anti-PD-1 (anti-CD279) antibody, an anti-PDL-1 antibody, an anti-GITR antibody, and an anti-OX-40 (anti-CD 134) antibody, wherein the antibody comprises a monoclonal antibody, a human antibody, a humanized antibody or a chimeric antibody.

14. A kit comprising
(a) a first composition that comprises a compound that has a structure:

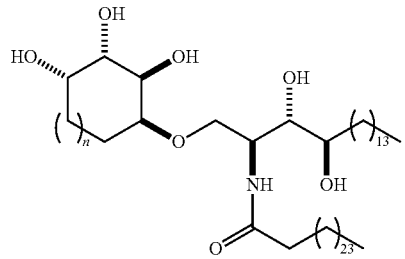

wherein n is 1, 2, or 3;
or a salt, ester, solvate, or hydrate thereof; and
(b) a cancer antigen that comprises at least one member selected from one or more of (i) MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (AGE-B4), tyrosinase, brain glycogen phosphorylase, Melan-A, MAGE-C1, MAGE-C2, NY-ESO-1, LAGE-1, SSX-1, SSX-2 (HOM-MEL-40), SSX-1, SSX-4, SSX-5, SCP-1, CT-7, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RARa fusion protein, PTPRK, K-ras, N-ras, Triosephosphate isomerase, GnTV, Herv-K-mel, Lage-1, NA-88, /Lage-2, SP17, and TRP2-Int2, (MART-1), gplOO (Pmel 17), TRP-1, TRP-2, MAGE-1, MAGE-3, p15(58), CEA, NY-ESO (LAGE), SCP-1, Hom/Mel-40, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, CDK4, Mum-1, p16, TAGE, PSMA, PSCA, CT7, telomerase, 43-9F, 5T4, 791Tgp72, a-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NBM70K, NY-CO-1, RCAS1, SDC-CAG16, TA-90 (Mac-2 binding protein\cyclophilin C-associated protein), TAAL6, TAG72, TLP, and TPS; and (ii) immunogenic fragments that comprise an epitope of any of the foregoing antigens, wherein (a) and (b) are packaged together but not in admixture.

15. A lipid-based formulation comprising the compound and the therapeutic agent of claim 1.

16. The composition of claim 4, wherein the therapeutic comprises a cancer antigen that comprises at least one member selected from one or more of (a) MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, MAGE-Xp2 (MAGE-B2), MAGE-Xp3 (MAGE-B3), MAGE-Xp4 (AGE-B4), MAGE-C1, MAGE-C2, MAGE-1, MAGE-3, MAGE-4, MAGE-5, and MAGE-6; and (b) immunogenic fragments that comprise an epitope of any of the foregoing antigens.

17. The method of claim 10, wherein the therapeutic comprises a cancer antigen that comprises at least one member selected from one or more of (a) MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, and MAGE-A13, MAGE-Xp2 (MAGE-B2), MAGE-Xp3 (MAGE-B3), MAGE-Xp4 (AGE-B4), MAGE-C1, MAGE-C2, MAGE-1, MAGE-3, MAGE-4, MAGE-5, and MAGE-6; and (b) immunogenic fragments that comprise an epitope of any of the foregoing antigens.

18. The kit of claim 14, wherein the cancer antigen comprises at least one member selected from one or more of (a) MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, MAGE-Xp2 (MAGE-B2), MAGE-Xp3 (MAGE-B3), MAGE-Xp4 (AGE-B4), MAGE-C1, MAGE-C2, MAGE-1, MAGE-3, MAGE-4, MAGE-5, and MAGE-6; and (b) immunogenic fragments that comprise an epitope of any of the foregoing antigens.

19. The method of claim 11, wherein n is 1.

20. The kit of claim 14, wherein n is 1.

21. A method of activating a natural killer T (NKT) cell comprising contacting the cell with (a) a compound having a structure:

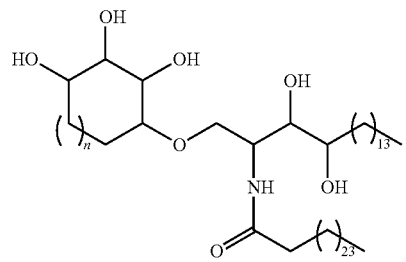

wherein n is 1, 2, or 3;
or a salt, ester, solvate, or hydrate thereof; and
(b) a therapeutic selected from the group consisting of a chemotherapeutic agent, a biological response modifying agent, and an immunotherapeutic agent,
in amounts effective to activate the NKT cell.

22. The method of claim 21, wherein the therapeutic comprises an immunotherapeutic that comprises a cancer vaccine, a cancer antigen, or a polynucleotide that comprises a nucleotide sequence that encodes a cancer antigen.

23. The method of claim 21, wherein the therapeutic comprises a cancer antigen that comprises at least one member selected from one or more of (a) MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (AGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1, CT-7, alpha-actinin-4, Bcr-Abl fusion protein, Casp-8, beta-catenin, cdc27, cdk4, cdkn2a, coa-1, dek-can fusion protein, EF2, ETV6-AML1 fusion protein, LDLR-fucosyltransferaseAS fusion protein, HLA-A2, HLA-A11, hsp70-2, KIAAO205, Mart2, Mum-2, and 3, neo-PAP, myosin class I, OS-9, pml-RARa fusion protein, PTPRK, K-ras, N-ras, Triosephosphate isomerase, GnTV, Herv-K-mel, Lage-1, NA-88, /Lage-2, SP17, and TRP2-Int2, (MART-1), gplOO (Pmel 17), TRP-1, TRP-2, MAGE-1, MAGE-3, p15(58), CEA, NY-ESO (LAGE), SCP-1, Hom/Mel-40, p53, H-Ras, HER-2/neu, BCR-ABL, E2A-PRL, H4-RET, IGH-IGK, MYL-RAR, Epstein Barr virus antigens, EBNA, human papillomavirus (HPV) antigens E6 and E7, TSP-180, MAGE-4, MAGE-5, MAGE-6, p185erbB2, p180erbB-3, c-met, nm-23H1, PSA, TAG-72-4, CA 19-9, CA 72-4, CAM 17.1, NuMa, K-ras, CDK4, Mum-1, p16, TAGE, PSMA, PSCA, CT7, telomerase, 43-9F, 5T4, 791Tgp72, a-fetoprotein, 13HCG, BCA225, BTAA, CA 125, CA 15-3 (CA 27.29\BCAA), CA 195, CA 242, CA-50, CAM43, CD68\KP1, CO-029, FGF-5, G250, Ga733 (EpCAM), HTgp-175, M344, MA-50, MG7-Ag, MOV18, NBM70K, NY-CO-1, RCAS1, SDCCAG16, TA-90 (Mac-2 binding protein\cyclophilin C-associated protein), TAAL6, TAG72, TLP, and TPS; and (b) immunogenic fragments that comprise an epitope of any of the foregoing antigens.

24. The method of claim 21, wherein the contacting comprises administering the compound and the therapeutic agent to a subject in need of NKT cell activation.

25. The method of claim 24, wherein the subject suffers from cancer, wherein the cancer is selected from the group consisting of basal cell carcinoma, breast cancer, leukemia, Burkitt's Lymphoma, colon cancer, esophageal cancer, bladder cancer, gastric cancer, head and neck cancer, hepatocellular cancer, Hodgkin's Lymphoma, hairy cell leukemia, Wilms' Tumor, thyroid cancer, thymoma, thymic carcinoma, testicular cancer, T-cell lymphoma, prostate cancer, non-small cell lung cancer, liver cancer, renal cell cancer and melanoma.

26. The method of claim 21, further comprising administering an immunotherapeutic agent that comprises at least one antibody selected from the group consisting of an anti-Her2/neu receptor antibody, an anti-CD52 antibody, an anti-CD33 antibody, an anti-CD20 antibody, an anti-TNFa antibody, an anti-CD25 IL-2 receptor antibody, an anti-CD40/CD40L antibody, an anti-CTLA-4 antibody, an anti-PD-1 (anti-CD279) antibody, an anti-PDL-1 antibody, an anti-GITR antibody, and an anti-OX-40 (anti-CD 134) antibody, wherein the antibody is a monoclonal antibody, a humanized antibody, a human antibody or a chimeric antibody.

* * * * *

UNITED STATES PATENT AND TRADEMARK OFFICE
CERTIFICATE OF CORRECTION

Page 1 of 1

PATENT NO.        : 10,314,796 B2
APPLICATION NO.   : 15/616672
DATED             : June 11, 2019
INVENTOR(S)       : Vincenzo Cerundolo et al.

It is certified that error appears in the above-identified patent and that said Letters Patent is hereby corrected as shown below:

In the Specification

Column 57, Line 63, "(AGE-B4)," should read -- (MAGE-B4), --.

Column 99, Line 37, "(AGE-B4)," should read -- (MAGE-B4), --.

In the Claims

Column 102, Line 18, "(AGE-B4)," should read -- (MAGE-B4), --.

Column 103, Line 42, "(AGE-B4)," should read -- (MAGE-B4), --.

Column 104, Line 55, "(AGE-B4)," should read -- (MAGE-B4), --.

Column 105, Line 35, "(AGE-B4)," should read -- (MAGE-B4), --.

Column 105, Line 47, "(AGE-B4)," should read -- (MAGE-B4), --.

Column 105, Line 59, "(AGE-B4)," should read -- (MAGE-B4), --.

Column 106, Line 34, "(AGE-B4)," should read -- (MAGE-B4), --.

Signed and Sealed this
Seventeenth Day of March, 2020

Andrei Iancu
*Director of the United States Patent and Trademark Office*